US009347961B2

(12) United States Patent
Karlsen et al.

(10) Patent No.: US 9,347,961 B2
(45) Date of Patent: May 24, 2016

(54) TEST KIT FOR THE QUANTITATIVE DETERMINATION OF NARCOTIC DRUGS

(71) Applicant: CHIRON AS, Trondheim (NO)

(72) Inventors: Morten Salihi Karlsen, Trondheim (NO); Huiling Liu, Trondheim (NO); Jon Eigill Johansen, Tiller (NO)

(73) Assignee: CHIRON AS, Trondheim (NO)

( * ) Notice: Subject to any disclaimer, the term of this patent is extended or adjusted under 35 U.S.C. 154(b) by 0 days.

(21) Appl. No.: 14/414,146

(22) PCT Filed: Jul. 19, 2013

(86) PCT No.: PCT/EP2013/065323
§ 371 (c)(1),
(2) Date: Jan. 12, 2015

(87) PCT Pub. No.: WO2014/013063
PCT Pub. Date: Jan. 23, 2014

(65) Prior Publication Data
US 2015/0204893 A1 Jul. 23, 2015

(30) Foreign Application Priority Data
Jul. 19, 2012 (EP) .................................... 12177125

(51) Int. Cl.
*H01J 49/00* (2006.01)
*G01N 33/94* (2006.01)
*G01N 30/72* (2006.01)

(52) U.S. Cl.
CPC ................ *G01N 33/94* (2013.01); *G01N 30/72* (2013.01); *G01N 33/946* (2013.01)

(58) Field of Classification Search
None
See application file for complete search history.

(56) References Cited

U.S. PATENT DOCUMENTS

| | | | | |
|---|---|---|---|---|
| 8,455,619 B2* | 6/2013 | Latham | ..................... | C07K 1/02 530/333 |
| 8,703,099 B2* | 4/2014 | Reis | ..................... | C07D 243/24 424/9.1 |
| 8,796,267 B2* | 8/2014 | Tung | ............................ | 514/231.2 |
| 2006/0281776 A1* | 12/2006 | Giribone | ............ | A61K 51/0455 514/283 |
| 2007/0037815 A1* | 2/2007 | Tung | ..................... | C07D 317/54 514/249 |
| 2007/0066657 A1* | 3/2007 | Tung | ..................... | C07D 401/12 514/326 |
| 2007/0116643 A1* | 5/2007 | Tung | ..................... | C07B 59/002 423/647.7 |
| 2007/0191432 A1* | 8/2007 | Tung | ..................... | C07D 317/64 514/320 |
| 2007/0276001 A1* | 11/2007 | Tung | ..................... | C07D 401/12 514/326 |
| 2008/0058351 A1* | 3/2008 | Tung | ..................... | C07B 59/002 514/259.3 |
| 2008/0287495 A1* | 11/2008 | Tung | ..................... | C07D 317/64 514/321 |
| 2009/0068706 A1* | 3/2009 | Freudenschuss | ......... | C12P 1/02 435/71.3 |
| 2009/0093422 A1* | 4/2009 | Tung | ..................... | C07D 413/10 514/36 |
| 2009/0208413 A1* | 8/2009 | Reis | ..................... | C07D 243/24 424/1.81 |
| 2009/0291152 A1* | 11/2009 | Tung | ..................... | C07D 417/12 424/722 |
| 2010/0130723 A1* | 5/2010 | Latham | ..................... | C07K 1/10 530/342 |
| 2012/0156139 A1* | 6/2012 | Katz-Brull | ........... | A61K 31/136 424/9.3 |
| 2014/0227792 A1* | 8/2014 | Johansen | ............. | A61K 31/137 436/8 |

FOREIGN PATENT DOCUMENTS

| | | | |
|---|---|---|---|
| EP | 2551675 A1 | | 1/2013 |
| JP | 2008266149 A | * | 11/2008 |
| WO | 2004056398 A1 | | 7/2004 |
| WO | 2006091885 A2 | | 8/2006 |
| WO | 2011024156 A1 | | 3/2011 |

OTHER PUBLICATIONS

Thomas Berg et al: "C labelled internal standardsA solution to minimize ion suppression effects in liquid chromatographytandem mass spectrometry analyses of drugs in biological samples?", Journal of Chromatography, Elsevier Science Publishers B.V, NL, vol. 1218, No. 52, Oct. 26, 2011, pp. 9366-9374.

Marie Kjaergaard Bjork et al: "Determination of 19 drugs of abuse and metabolites in whole blood by high-performance liquid chromatogarphyâ tandem mass spectrometry", Analytical and Bioanalytical Chemistry, Springer, Berlin, DE, vol. 396, No. 7, Nov. 18, 2009, pp. 2393-2401.

Ceder Gunnel et al: "Concentrations of Unconjugated Morphine, Codeine and 6-Acetylmorphine in Urine Specimens From Suspected Drugged Drivers", Journal of Forensic Sciences, Callaghan and CO, Chicago, IL, US, vol. 47, No. 2, Jan. 1, 2002, pp. 366-368.

Wei-Tun Chang et al: "13C4-Secobarbital as the Internal Standard for the Quantitative Determination of Secobarbital-A Critical Evaluation", J Forensic Sci, vol. 45, No. 3, Jan. 1, 2000, pp. 659-664.

(Continued)

Primary Examiner — Andrew Smyth
(74) Attorney, Agent, or Firm — Abel Law Group, LLP

(57) ABSTRACT

A test kit for the quantitative determination of narcotic drugs comprising (A) series of sealed vessels, each vessel containing a deuterium free isotopologue of a narcotic drug in exactly defined concentrations and quantities, wherein the isotopologue differs from vessel to vessel and—wherein the quantities of the isotopologue differ from vessel to vessel or are the same for all vessels; and/or (B) series of sealed vessels, each vessel containing in exactly defined concentrations and quantities the same isotopologue in quantities which differ from vessel to vessel; wherein the free isotopologues are selected from narcotic drugs; prodrugs, salts, solvates, hydrates and polymorphs and contain at least three stable isotopes selected from the group consisting of $^{13}C$, $^{15}N$ and $^{18}O$ in the molecule with a degree of labeling of at least 95 mol-%; the use of the test kit and a method for quantitatively determining narcotic drugs.

20 Claims, No Drawings

(56) References Cited

OTHER PUBLICATIONS

Ray H. Liu et al: "Peer Reviewed: Isotopically Labeled Analogues for Drug Quantitation", Analytical Chemistry, vol. 74, No. 23, Dec. 1, 2002, pp. 618 A-626 A.

Wei-Tun Chang et al: "Mechanistic Studies on the Use of 2H- and 13C-Analogues as Internal Standards in Selected Ion Monitoring GC-MS Quantitative Determination—Butalbitai Example", Journal of Analytical Toxicology, vol. 25, Jan. 1, 2001, pp. 659-669.

Rodger L. Foltz et al: "GC/MS Assays for Abused Drugs in Body Fluids", NIDA RES MONOGR., vol. 32, Jan. 1, 1980, pp. pp. 1-214.

Singh G et al: "A validated stable isotope dilution liquid chromatography tandem mass spectrometry assay for the trace analysis of cocaine and its major metabolites in plasma", Analytical Chemistry, American Chemical Society, US, vol. 71, No. 10, May 15, 1999, pp. 2021-2027.

Wang S M et al: "Simultaneous determination of amphetamine and methamphetamine enantiomers in urine by simultaneous liquid-liquid extraction and diastereomeric derivatization followed by gas chromatographic-isotope dilution mass spectrometry", Journal of Chromatography B: Biomedical Sciences & Applications, Elsevier, Amsterdam, NL, vol. 816, No. 1-2, Feb. 2005, pp. 131-143.

\* cited by examiner

TEST KIT FOR THE QUANTITATIVE DETERMINATION OF NARCOTIC DRUGS

The present invention relates to a novel test kit for the quantitative determination of narcotic drugs containing at least one deuterium free labeled, in particular $^{13}C$ labeled, isotopologue of a narcotic drug.

Furthermore, the present invention relates to the use of the novel test kits in chemical analysis and metabolic studies.

Additionally, the present invention relates to a novel analytical method for the determination of narcotic drugs.

CITED DOCUMENTS

The documents cited in the present application are incorporated by reference in their entirety.

DESCRIPTION OF THE PRIOR ART

Chemical analysis of pharmaceuticals and legal and illegal drugs and their metabolites and impurities can be performed by any method applying combinations of gas chromatography (GC), liquid chromatography (LC), ultra performance liquid chromatography (UPLC), mass spectrometry (MC), tandem mass spectrometry (MC/MC) and/or nuclear magnetic resonance spectroscopy (NMR), as for example, GC-MS, GC-MS/MS, LC-MS, LC-MS/MS, UPLC-MS, UPLC-MS/MS, UPLC-MS/MS, LC-NMR and UPLC-NMR.

Internal standards are used to determine the level or quantity of each analyte in the sample. Traditionally, such an analysis is performed using deuterium labeling of the analyte. However, disadvantages associated with deuterium labeling are the risk of exchange, i.e. deuterium and hydrogen can be exchanged in the workup procedure, and different elution times, i.e. the deuterium labeled compounds elute differently from the native, unlabeled compounds both in GC and in LC. In addition, the deuterium labeled compounds may have a response factor which is slightly different from the response factor of the native, unlabeled compounds.

The $^{13}C$ isotope labeled internal standards are particularly suitable of minimizing the effects of ion suppression effects in LC-MS/MS analysis, therefore the quantitative analysis in various biological samples are particularly accurate and reproducible.

In a $^{13}C$ labeled compound, there is no risk of exchange, and the labeled compounds elute identically with the unlabeled compounds both in GC and LC. Moreover, they have the same response factor when using mass detection. However, natural matter contains approximately 1.1% $^{13}C$ so that there is a danger of an "overlap" with the natural $^{13}C$ in the native compound. Therefore, the number of labeled atoms must preferably be at least three.

$^{13}C$ labeling has long been used in chemical analysis and in other fields like environmental analysis, in particular in the analysis of trace compounds like dioxins or polychlorinated biphenyls (PCBs). However, no such $^{13}C$ labeled compounds have been reported that can be used as chemical standards in order to obtain all the advantages of a compound with pure $^{13}C$ labeling not in combination with deuterium labeling.

Therefore, it would be highly desirable to have compounds available that are labeled, in particular with $^{13}C$, however, not in combination with deuterium.

In the past years, the abusive use of natural and synthetic psychoactive, narcotic drugs, namely
  stimulants ("uppers"),
  depressants ("downers") and
  hallucinogens, including psychedelics, dissociatives and deliriants
has become a worldwide major concern and has a tremendous negative social, criminal and economical impact in all societies. In particular, the highly addictive 2-phenylethylamine hallucinogens and/or stimulants such as amphetamine, methamphetamine and ecstasy are consumed in ever-growing amounts. Therefore, it would be particularly desirable to have compounds of this type available that are labeled with $^{13}C$ and, optionally, with $^{15}N$ and/or $^{18}O$, however, not in combination with deuterium, in order to have reliable standards for the chemical analysis of such illegal psychotropic, narcotic drugs at hand.

Sigma-Aldrich and Cambridge Isotope Laboratories offer $[^{13}C_9{}^{15}N]$-phenylalanine, Cambridge Isotope Laboratories offers $[^{13}C_9]$-phenylalanine and $[^{13}C_6]$-, $[^{13}C_9]$- and $[^{13}C_9{}^{15}N]$-tyrosine and Sigma-Aldrich offers $[^{13}C_6]$-ritalinic acid. The compounds are used for tandem MS standards. However, the compounds are not narcotic drugs, and, therefore, cannot serve as standards for their analysis.

In the article of I. A. Low, R. H. Liu, M. G. Legendre, E. G. Piotrowski and R. L. Furner in Biomedical & Environmental Mass Spectrometry (1986), 13 (10), 531-534, the use of a methamphetamine containing only one $^{13}C$-carbon atom is described in the mass spectrometry analysis.

The article of R. S. Hsi and L. S. Stelzer, Synthesis of Adinazolam multiply labeled with Carbon-13 and Deuterium, in Journal of Labelled Compounds in Radiopharmaceuticals, Volume XXVII, No. 3, 287-295, 1989, describes the synthesis and the spectroscopic properties of $[^{13}C_6]$-adinazolam. However, no test kits are disclosed.

Berg et al. (J. Chrom. Vol. 1218, no. 52, 9366) describes the use of $[^{13}C_6]$-methamphetamine as internal standard.

The Japanese patent application JP 2008-266149 A discloses estradiol with a $[^{13}C_6]$-benzene ring and various $[^{13}C_6]$-precursors such as $[^{13}C_6]$-benzene, -nitrobenzene, -iodonitrobenzene, -iodoaniline, -iodophenol and -iodoanisol. However, $[^{13}C_6]$-estradiol is no narcotic drug and, therefore, it cannot serve as a standard for the chemical analysis of narcotic drugs.

The article by A. Weis and S. P. Markey "Synthesis of D/L-Norepinephrine-U-$^{13}C$)" in Journal of Labelled Compounds and Radiopharmaceuticals, volume XXV, No. 1, pages 103 to 109 describe the synthesis of the said compound. However, norepinephrine is not a narcotic drug but a hormone and a neurotransmitter and, therefore, cannot serve as a standard for the chemical analysis of narcotic drugs.

The international patent application WO 2004/056398 A1 discloses isotope labeled camptothecine derivatives as internal standards for analytical methods. However, camptothecine and similar compounds are quinoline alkaloids having cytotoxic properties and no narcotic drugs.

The American patent application US 2007/0116643 A1 discloses deuterium labeled aryloxypropanamines wherein at least one carbon atom of the structure can be replaced by a $^{13}C$ isotope. A diagnostic kit for and a method of determining the concentration of aryloxypropanamines in biological samples is cursorily mentioned. The method uses deuterium labeled aryloxypropanamines wherein at least one carbon atom of the structure and can be replaced by a $^{13}C$ isotope. However, the aryloxypropanamines are no narcotic drugs, but known pharmaceuticals for treating depression and diabetes neuropathy pain.

The American patent application US 2009/0068706 A1 discloses highly isotopically labeled secondary microbial metabolic products of fungi and bacteria selected from the group consisting of mycotoxins;
trichothecenes, such as nivalenol, deoxynivalenol, 3-acetyl-deoxynivalenol, and 15-acetyl-deoxynivalenol;
fusarenon X;
T-2 toxin and HT-2 toxin;
fumonisins, such as fumonisin B1, B2 or B3;
ochratoxins, such as ochratoxin A, B, C or D;
zealarenones;
moniliformin;
aflatoxins, such as aflatoxin B1, B2, G1 or G2;
antibiotics formed of actinomycetes, such as tetracyclines, streptomycins or aminoglycosides;
antibiotics formed of *Bazillus* sp., such as bacitracin or polymyxin;
antibiotics formed of *Penicillium*, such as penicillin or griseofulvin; and
cephalosporins formed of cephalosporium.

Preferably, all the carbon atoms of the structures are substituted by $^{13}C$ isotopes. The labeled compounds are used as internal standards in analytics, for metabolic studies in animal feeding tests, for metabolic studies for clarifying metabolic cycles, degradation paths and/or degradation periods as well as intercalations in a liquid synthetic culture medium. However, the said label compounds are no isotopologues of narcotic drugs, and, therefore, cannot be used as internal standards for the latter.

The international patent application WO 2011/024156 A1 discloses isotopically labeled neurochemical agents containing at least one $^{13}C$-carbon atom directly bonded to at least one deuterium atom and their use for diagnosing conditions and disorders in medicine.

The article of Chotima Poeaknapo, "Evaluation of the mass spectrometric fragmentation of codeine and morphine after $^{13}C$-isotope biosynthetic labeling", published in Phytochemistry 65 (2004) 1413-1420 describes the biosynthetic preparation of the said label compounds by germinating and subsequently growing poppy seeds in solutions containing [ring-$^{13}C_6$]-L-tyrosine or [ring-$^{13}C_6$]-tyramine. The labeling degree of codeine was calculated based on LC-MS full scan data as follows: [ring-$^{13}C_6$]-L-tyrosine into codeine: 30%; and [ring-$^{13}C_6$]-tyramine into codeine: 38%. Consequently, the isotopically enrichment is far below 95%. Moreover, no test kits are disclosed.

The international patent application WO 2006/091885 A2 discloses isotopically labeled benzodiazepines wherein at least two of the atoms of the structure are present as deuterium, $^{13}C$, $^{15}N$ or $^{18}O$ isotopes. Specifically disclosed are
double $^{13}C$ isotope labeled lorazepam;
$^{13}C_2$ and single $^{15}N$ isotope labeled lorazepam
$^{13}C_2$ and single $^{15}N$ isotope labeled oxazepam; and
$^{13}C_2$ and $^{15}N$ isotope labeled clonazepam;

Moreover, isotope labeled opiates are disclosed wherein at least one of the atoms on the structure is present as a deuterium, $^{13}C$, $^{15}N$ or $^{18}O$ isotope. Specifically disclosed are
single and double deuterium isotope labeled codeine; and
double deuterium isotope labeled oxycodone;
double deuterium and single $^{18}O$ isotope labeled oxycodone;
single $^{18}O$ isotope labeled oxycodone;
single, double and triple deuterium labeled hydrocodone;
single and double and deuterium labeled morphine; and
single, double and triple deuterium labeled hydromorphone.

Moreover, isotope labeled methadone is disclosed wherein at least one of the atoms of the structure is present as a deuterium, $^{13}C$, $^{15}N$ or $^{18}O$ isotope. Specifically disclosed are
single 13C isotope labeled methadone and
triple deuterium isotope labeled methadone.

Moreover, isotope labeled fentanyl, a partially synthetic opioid analgesic, is disclosed wherein at least two atoms of the structure are present as deuterium, $^{13}C$, $^{15}N$ or $^{18}O$ isotopes. No specific examples are disclosed.

Additionally, isotope labeled zolpidem, a soporific, is disclosed wherein at least one of the atoms of the structure is present as a deuterium, $^{13}C$, $^{15}N$ or $^{13}O$ isotope. Specifically disclosed are
$^2H_6$ isotope labeled zolpidem and
single $^{13}C$ and single $^{15}N$ isotope labeled zolpidem.

Furthermore, isotope labeled buprenorphine is disclosed wherein at least one of the atoms of the structure is present as a deuterium, $^{13}C$ or $^{15}N$ isotope. Specifically disclosed is
double deuterium labeled buprenorphine.

Furthermore, isotope labeled tramadol, an analgesic, is disclosed wherein at least one of the atoms of the structure is present as a deuterium, $^{13}C$ or $^{15}N$ isotope. Specifically disclosed are
single $^{13}C$ isotope labeled tramadol;
double $^{13}C$ isotope labeled tramadol;
triple deuterium isotope labeled tramadol; and
single deuterium and double $^{13}C$ isotope labeled tramadol.

Moreover, isotope labeled amphetamines, wherein at least one of the atoms are present as deuterium, $^{13}C$ or $^{15}N$ are described. Specifically, $^{13}C$-amphetamine, $^{13}C$-methamphetamine, $^{15}N$-amphetamine, $^{15}N$-methamphetamine, $^{13}C$-$^{15}N$-amphetamine and $^{13}C$-$^{15}N$-methamphetamine are disclosed.

Last but not least, [$^{13}C_6$]-methylphenidate (Ritalin™) and its [$^{13}C_6$]-precursors are disclosed. However, these compounds are not hallucinogens or narcotics.

The compounds are used for a registry method and control system for DEA schedule II-V medicines. No test kits are described.

Example 5, page 10, paragraph [0080] of the American patent application US 2010/0130723 A1 discloses [$^{13}C_6$]-amphetamine and its use in metabolic studies. however, no test kits are described.

The article of Simon Beuk et al, "Structure characterisation of urinary metabolites of the cannabimimetic JWH-018 using chemically synthesised reference material for the support of LC-MS/MS-based drug testing", published in Analytical and Bioanalytical Chemistry (2011) 401:493-505 discloses the $^{13}C_8$-$^{15}N$ isotopically labeled metabolite of JWH-018 (naphthalene-1-yl-(1-pentylindol-3-yl)methanone) wherein the pentyl group is converted to a pentanoic acid methyl ester group. The metabolite is synthesized from a [$^{13}C_8$-$^{15}N$]-indole (96-99% isotopic enrichment) as the educt. However, no test kit is disclosed.

The prior European patent application No. 11175719.1-1216 filed on Jul. 28, 2011 describes deuterium free, stable isotope labeled hallucinogens and/or stimulants containing a 2-phenylethylamine-based structural unit and containing at least three stable isotopes selected from the group consisting of a $^{13}C$, $^{15}N$ and $^{15}O$ as free bases and as their salts. The compounds can be used as analytical standards for the corresponding non-labeled isotopologues. However, no test kits are described.

OBJECTS OF THE INVENTION

It was the object of the invention to provide novel test kits for the quantitative determination of narcotic drugs.

The novel test kits should allow for the highly precise, exactly reproducible and convenient quantitative analysis and determination of narcotic drugs. The novel test kits should therefore allow for the precise dosage of internal and external standards, i.e., deuterium free, $^{13}C$ labeled isotopologues of narcotic drugs without the risk of loss of valuable material, in particular liquid and/or volatile material which loss would be an additional error source.

Of course, error sources have to be avoided or at least minimized since these internal and external standards are to be used in the field of medicine and forensic science. Consequently, the internal and external standards and test methods involved do not only have a natural science dimension but also, quite obviously so, human and legal dimensions. Thus, the crucial question whether there was a criminal act or not could depend on such tests.

Moreover, the novel test kits should increase the safety of the handling and transport of the highly intoxicating isotopologues of the narcotic drugs. Additionally, they should allow for a better control of stocks and ease the identification of the various materials.

Additionally, it was the object of the invention to provide novel methods for the chemical analysis and metabolic studies, in particular in the forensic analysis.

Last but not least, it was the object of the invention to provide novel methods of synthesizing deuterium free, $^{13}C$ labeled isotopologues of narcotic drugs in high yields and high purity.

SUMMARY OF THE INVENTION

Accordingly, a test kit for the quantitative determination of narcotic drugs has been found the said test kit containing A test kit for the quantitative determination of narcotic drugs comprising
(A) at least one series of sealed vessels, each vessel containing at least one and deuterium free isotopologue of a narcotic drug in exactly defined and certified concentrations, purities, and quantities,
  wherein at least one deuterium free isotopologue differs from vessel to vessel and
  wherein the quantities of at least one deuterium free isotopologue differ from vessel to vessel or are the same for all vessels; and/or
(B) at least one series of at least two sealed vessels, each vessel containing in exactly defined concentrations and quantities at least one of the same deuterium free isotopologue in quantities which differ from vessel to vessel;
wherein the at least one deuterium free isotopologue is selected from the group consisting of
  narcotic drugs;
  prodrugs, salts, solvates, hydrates and polymorphs of said narcotic drugs;
  salts, solvates, hydrates and polymorphs of the said prodrugs;
  metabolites of the said narcotic drugs and their prodrugs, salts, solvates, hydrates and polymorphs; especially metabolites of said drugs and/or prodrugs with increased hydrophilicity, preferably glucuronides of said drugs and/or prodrugs;
  metabolites of the said, salts, solvates, hydrates and polymorphs of the said prodrugs; and
  salts, solvates, hydrates and polymorphs of said metabolites; and
  contains at least three stable isotopes selected from the group consisting of $^{13}C$, $^{15}N$ and $^{18}O$ in the molecule with a degree of labeling of at least 95 mol-%.

Hereinafter, the novel test kit for the quantitative determination of narcotic drugs is referred to as the "test kit of the invention".

Additionally, the novel use of the test kit of the invention in chemical analysis and metabolic studies and for calibrating analytical methods used for the quantitative determination of narcotic drugs has been found.

Hereinafter, the novel use of the test kit of the invention is referred to the "use of the invention".

Moreover, the novel method for the quantitative determination of narcotic drugs in analytical samples has been found, the method comprising the steps of
(1) identifying the narcotic drug to be quantitatively determined in an analytical sample;
(2) selecting the sealed vessel or vessels containing the corresponding deuterium free isotopologue of the narcotic drug from the test kit of the invention;
(3) adding the isotopologue to the analytical sample as a standard, preferably internal standard, or adding an amount, preferably the same amount of the biological specimen, e.g. body fluid to each vessel of the test kit; and
(4) quantitatively determining the narcotic drug in the analytical sample with a suitable analytical method.

Hereinafter, the novel method for the quantitative determination of narcotic drugs is referred to as the "method of the invention".

ADVANTAGES OF THE INVENTION

In view of the prior art, it was surprising and could not be expected by the skilled artisan that the objects underlying the present invention could be solved by the test kit of the invention, the use of the invention and the method of the invention.

The test kit, the use and the method of the invention allowed for the highly precise, exactly reproducible and convenient quantitative analysis and determination of narcotic drugs. The test kit of the invention allowed for the precise dosage of internal and external standards, i.e., the deuterium free isotopologues of narcotic drugs without the risk of loss of valuable material, in particular liquid and/or volatile material which loss would be an additional error source.

Such error sources could be avoided or at least significantly minimized, which is highly important since these isotopologues of narcotic drugs were used as internal and external standards in the field of medicine and forensic science. Consequently, the test kits, the use and the analytical method of the invention not only have a natural science dimension but also, quite obviously so, human and legal dimensions. Thus, the crucial question whether there was a criminal act or not could depend on such tests. However, the test kit, the use and the method of the invention excellently fulfilled the strictest requirements of the art also in this regard.

Moreover, the test kit, the use in the method of the invention increased the safety of the handling and transport of the highly intoxicating isotopologues of the narcotic drugs. Additionally, they allowed for a better control of stocks and ease the identification of the various materials.

Additionally the use of the test kit of the invention with (isotopologues as) internal standard assures precision and accuracy in handling and execution of the analysis as well as in the result. This is especially due to a successful correction of ion suppression which occurs in LC-MS.

Further, by using internal standards, the loss of an amount of the analytic sample during analysis does not adulterate the result, because the ratio between the biological specimen and the internal standard remains constant.

The test kit of the invention puts validated and standard-compliant analysis reagents with long shelf-life at disposal, covering a complete range of parameters or with standards for application-oriented measuring ranges.

The kit is easier to transport and storage.

The use of the test kit assures secure, reproducible and reliable results with improved accuracy, because with exception of the transfer of the biological specimen into the vessel of the kit, all other pipetting step are eliminated.

DETAILED DESCRIPTION OF THE INVENTION

In its broadest aspect, the present invention is directed to a test kit for the quantitative determination of narcotic drugs.

In the context of the present invention, a test kit is a commercially packaged system of the principal key components of an analytical method used to determine the presence of a specific analyte or specific analytes in a given matrix or in given matrices. Test kits include directions for their use and are of a self contained, complete analytical systems, which may or may not require supporting supplies and equipment.

In an alternative the test kit of the invention is a commercially prepared reagent sets, where appropriate with accessory devices, containing all of the major components and literature necessary to perform one or more designated diagnostic tests or procedures.

Therefore, the deuterium free isotopologues of the test kit of the invention are packaged in sealed vessels. Preferably, the sealed vessels are selected from the group consisting of glass or plastic vials, blister packages, plastic bags, containers which dissolve in suitable solvents and release the compounds, glass, metal and plastic screw cap containers and containers closed by rubber or silicone diaphragms or septums.

The sealed vessels may be accompanied by syringes and/or measuring pipettes for removing liquid compounds or dissolved or dispersed compounds from the containers and metering them in exactly known quantities to analytes. The sealed vessels may also be especially adapted for placing them into measuring pipettes such as plunger-operated pipetters or other metering systems which are capable of metering the deuterium free isotopologues in exactly known quantities to the analytes.

The sealed vessels may be standardized and adapted for analytical robot applications.

Furthermore, the test kit of the invention is either of the type A or the type B. Additionally, the test kit of the invention can comprise a combination of both type A or type B test kits.

The type A test kit of the invention comprises at least one series of sealed vessels, each vessel containing at least one deuterium free isotopologue of a narcotic drug in exactly defined concentrations and quantities, wherein at least one deuterium free isotopologue differs from vessel to vessel and
  wherein the quantities of at least one deuterium free isotopologue differ from vessel to vessel or are the same for all vessels.

Preferably, the type A test kit of the invention comprises at least 3 sealed vessels.

The type type B test kit of the invention comprises at least one series of at least two, preferably at least 3, sealed vessels, each vessel containing in exactly defined concentrations and quantities at least one of the same deuterium free isotopologue in quantities which differ from vessel to vessel.

Preferably, the quantities of the at least one deuterium free isotopologue in each vessel are such that they suffice for at least one analysis of the corresponding narcotic drug in an analytical sample.

Therefore, the quantities can vary broadly and can be adapted most advantageously to the requirements of the chosen to analytical method. Preferably, the quantity of a deuterium free isotopologue in a sealed vessel is in the range of from $10^{-7}$-1000 µM, more preferably $10^{-5}$-1000 µM and most preferably $10^{-4}$-1000 µM.

In one embodiment the quantity of a deuterium free isotopologue in a sealed vessel is 0.05; 0.1; 0.25; 0.4; 0.5; 1.0; 2.0; 2.5; 5.0; 10.0; 20.0; 40.0; 50.0; 100.0; 200.0; 250.0; 400.0; 500.0; 600.0; 750.0; 800.0 and/or 1000.0 µM.

In one embodiment the quantity of a deuterium free isotopologue as preferably internal standard in an analytical sample is 0.1; 0.25; 0.4; 0.5; 1.0; 2.0; 2.5; 5.0; 10.0; 20.0; 40.0; 50.0; 100.0; 200.0; 250.0; 400.0; 500.0; 600.0; 750.0; 800.0 and/or 1000.0 µM.

In one embodiment of the invention the series of sealed vessels as components of the test kit comprises each of them at least one deuterium free isotopologue, preferably as internal standard for analysis with different procedures and/or detection instruments based on the same analytical methodology. In one alternative, all probes are analyzed with the same procedures and/or detection instruments.

The test kit of intervention can contain at least one additional component. Preferably, the additional component has an auxiliary function thus supporting the use of the method of the invention. Examples for suitable auxiliary components of the test kit of the invention are buffers, solvents, dispersing agents, porous or non-porous solid absorptive supports or microcapsules, preferably solvents. The auxiliary components can be contained in the sealed vessels together with the deuterium free isotopologues and/or can be stored in separate standardized containers until further use.

Moreover, the test kit of the invention can contain sealed vessels containing the corresponding non-labeled narcotic drugs in known quantities, e.g. for purposes of calibrating analytical methods.

Additionally, the test kit of the invention may also comprise visible, electronic and/or barcode labeling, both coded or non-coded; descriptions, handbooks and teaching material in paper or on CD-ROM; and/or crash and break proof carrying cases with or without mechanical, electrical and/or digital safety devices of which guard the test kit of the invention, in particular, the narcotic drugs and their deuterium free isotopologues, against illicit misuse.

The deuterium free isotopologues of the test kit of the invention are selected from the group consisting of narcotic drugs;
  prodrugs, salts, solvates, hydrates and polymorphs of said narcotic drugs;
  salts, solvates, hydrates and polymorphs of the said prodrugs;
  metabolites of the said narcotic drugs and their prodrugs, salts, solvates, hydrates and polymorphs; especially metabolites of said drugs and/or prodrugs with increased hydrophilicity, preferably glucuronides of said drugs and/or prodrugs;
  metabolites of the said salts, solvates, hydrates and polymorphs of the said prodrugs; and
  salts, solvates, hydrates and polymorphs of said metabolites; and and contain at least three, preferably at least four, more preferably at least five and most preferably at least six stable isotopes selected from the group consisting of $^{13}O$, $^{15}N$ and $^{18}O$, most preferably $^{13}C$, in the molecule with a degree of labeling of at least 95 mol-%, preferably at least 98 mol-%, more preferably at least 99 mol-% and, most preferably at least 99.5 mol-%.

Most preferably, the isotopologues are in the dissolved state.

The term "isotopologue" refers to a species that differs from one of the above-mentioned compounds only in the isotopic composition of its molecular structure.

In the context of the present invention, the term "deuterium free" means that the isotopologue only contains deuterium in the naturally occurring quantities.

In in the context of the present invention, narcotic drugs are natural or synthetic products which are capable of generating intoxication by stimulating, dampening or paralyzing the central nervous system (CNS). After enteral or parenteral supplying, the narcotic drugs effect a distorted or warped perception of the environment and of the own personality. The intoxication induced by the stimulation or the palsy of the CNS are accompanied by psychic disinhibition, disturbances of the mental equilibrium, distortion of sensorial perceptions, the triggering of hallucinations, euphoria, changes in mood, analgesia etc. The intensity and the type of the symptoms depend on the type of the narcotic drug.

Since the narcotic drugs not only could use psychedelic effects but also affect the structure of personality, some of them are categorized as psychodysleptica or psycholytica.

The perilousness of the narcotic drugs is based in first place on the fact that they feign (for a short time) a "problem solving" or an "expansion of the consciousness" although there is only a flight from reality or a disturbance in neurophysiology. From these flow the personality destructive effects of the narcotic drugs and the psychological addiction, which happens with all the narcotic drugs. Secondly, some of the narcotic drugs lead to a physiological addiction caused by the permanent damage of particular physiological and neurophysiological equilibria.

Seen from the vantage point of the motives for their use or the "artificial paradise" that they feign, the narcotic drugs can be divided into four groups.

1. The Morphine Type

The morphine type narcotic drugs abduct the consumer into deceptive dream world, they sedate and at the same time, induce dreamlike hallucinations.

2. The Cocaine Type

The cocaine type narcotic drugs lead to an overreaching appraisal of the own personality or to a short and intensive brightening of the mood. Most of them activate the sympathetic and the dopaminergic system. Some designer drugs are also designate it as entactogenes which means that they "create a feeling inside". They subjectively facilitate the self-absorption in the sense of a pre-stage of a real trance or ecstasy.

3. The Ethanol Type

The ethanol type narcotic drugs cause a flight from reality into spiritual phlegm. They dampen the CNS by enhancing the effect of the dampening neurotransmitter GABA (gamma-aminobutyric acid) and/or interfere with dopaminergic system.

4. The LSD Type

The LSD type narcotic drugs seemingly lead to an expanded or deep and perception of the reality. However, they distort the sensory perceptions by interfering with the serotonergic and dopaminergic neurons.

(Cf. also the Römmp Online 2012, Georg Thieme Verlag, Rauschgifte)

In one embodiment of the invention narcotic drugs are defined according to the United Nations Convention against illicit traffic in narcotic drugs and psychotropics substances 1988.

In this context "Narcotic drug" means any of the substances, natural or synthetic, in Schedules I and II of the Single Convention on Narcotic Drugs, 1961, and that Convention as amended by the 1972 Protocol Amending the Single Convention on Narcotic Drugs, 1961.

Narcotic drugs include in one embodiment also any psychotropic substance, which is defined as any substance, natural or synthetic, or any natural material in Schedules I, II, III and IV of the Convention on Psychotropic Substances, 1971.

Hence meanwhile new drugs were developed, the term narcotic drug includes in one embodiment a substance classified as narcotic drug or psychotropic substance by the World Health Organization.

A narcotic drug or psychotropic substance of the invention comprise in one embodiment any substance which has the capacity to produce a state of dependence and a central nervous system stimulation or depression, resulting in hallucinations or disturbances in motor function or thinking or behaviour or perception or mood, or which has similar abuse and similar ill effects as a substance in Schedule I, II, III or IV of the Convention on Psychotropic Substances, 1971.

According to the invention the term "drug" encompasses in one embodiment one or more substances selected from the group comprising: natural and synthetic psychoactive, narcotic drugs, narcotics, stimulants ("uppers"), depressants ("downers"), hallucinogens, psychedelics, dissociatives and deliriants.

In the context of the present invention, a prodrug is a biologically inactive or essentially inactive precursor of the corresponding narcotic drug, which prodrug is converted to the actual narcotic drugs in the human or animal body. Esters of narcotic drugs are frequently used for this purpose. Additional examples for prodrugs are described in the American patent application US 2007/0116643 A1, page 22, paragraphs [0095].

A salt is a salt formed from an acid or a base depending on the chemical nature of the deuterium free isotopologues which form the counterions. In particular, acids are used.

Acids commonly employed to form such salts include inorganic acids such as hydrochloric, hydrobromic, hydroiodic, sulfuric, boric, phosphoric, polyphosphoric and phosphorous acid.

Likewise, organic acids selected from the group consisting of carboxylic acids, sulfonic acids, phosphoric acids, acidic sulfate esters and acidic phosphate esters can also be used.

Most preferably, pharmaceutically acceptable salts are used. Additional examples of such a pharmaceutically acceptable salts are described in the American patent application US 2007/0116643 A1, page 22, In the context of the present invention, the term "hydrate" means one of the above-mentioned compounds which further includes a stoichiometric or non-stoichiometric amount of water bound by non-covalent intermolecular forces.

The term "solvate" means one of the above-mentioned compounds are there which further includes a stoichiometric or non-stoichiometric amount of an organic solvent bound by non-covalent intermolecular forces.

The term "polymorph" means solid crystalline forms of one of the above-mentioned compounds. Different polymorphs of the same compound can exhibit different physical, chemical and/or spectroscopic properties.

For further details, reference is made to page 22, paragraphs [0091]-[0095] and to page 23, paragraph [0097] of the American patent application US 2007/0116643 A1.

The term "metabolite" refers to a compound resulting from the metabolizing of one of the above-mentioned compounds into a biological system, in particular in the human body.

Preferably, the narcotic drug is selected from the group consisting of benzodiazepines, morphines, cocaines, cannabinoids, piperazines, LSD, methadone, naphthoylindoles, naphthylpyrrols, amphetamines and benzazocines.

Therefore, the deuterium free isotopologues of the test kit of the invention preferably contains at least one isotopologue of

- the narcotic drug selected from the group consisting of benzodiazepines, morphines, cocaines, cannabinoids, piperazines, LSD, methadone, naphthoylindoles, naphthylpyrrols, amphetamines and benzazocines;
- the prodrugs, salts, solvates, hydrates and polymorphs of selected narcotic drug;
- the salts, solvates, hydrates and polymorphs of the said prodrugs;
- the metabolites of the selected narcotic drug and its prodrugs, salts, solvates, hydrates and polymorphs; especially metabolites of said drugs and/or prodrugs with increased hydrophilicity, preferably glucuronides of said drugs and/or prodrugs;
- the metabolites of the said, salts, solvates, hydrates and polymorphs of the said prodrugs; and
- the salts, solvates, hydrates and polymorphs of said metabolites.

Subject matter of the present invention is in one embodiment an isotopologue as mentioned below, preferably glucuronides.

In one embodiment the isotopologue contains only $^{13}C$ as isotope, with exception of naturally isotopes being present in the respective substance, like deuterium in a naturally abundance of 0.115, $^{15}N$ in a naturally abundance of 0.368 or $^{18}O$ in a naturally abundance of 0.205 (percent natural abundance data is from the 1997 report of the IUPAC Subcommittee for Isotopic Abundance Measurements by K. J. R. Rosman, P. D. P. Taylor Pure Appl. Chem. 1999, 71, 1593-1607).

In one embodiment glucuronides are preferred.

Hereinafter, suitable examples of narcotic drugs are listed. In the context of the present invention, it is to be understood that these examples also refer to the respective isotopologues of

- the narcotic drugs;
- their prodrugs, salts, solvates, hydrates and polymorphs of said narcotic drugs; their salts, solvates, hydrates and polymorphs of the said prodrugs;
- the metabolites of the narcotic drugs and their prodrugs, salts, solvates, hydrates and polymorphs; especially metabolites of said drugs and/or prodrugs with increased hydrophilicity, preferably glucuronides of said drugs and/or prodrugs;
- their metabolites of the said salts, solvates, hydrates and polymorphs of the said prodrugs; and the salts, solvates, hydrates and polymorphs of the said metabolites.

In one embodiment the test kit of the invention comprises or contains isotopologues of drugs of the morphine type.

In one embodiment the test kit of the invention comprises or contains isotopologues of drugs of the cocaine type.

In one embodiment the test kit of the invention comprises or contains isotopologues of drugs of the ethanol type.

In one embodiment the test kit of the invention comprises or contains isotopologues of drugs of the LSD type.

In one embodiment the test kit of the invention comprises or contains one or more isotopologues according to table A.

TABLE A

| Test Kit No. | Isotopologue (Standard) | Vessel 1 Quantity/ $\mu M^{a)}$ | Vessel 2 Quantity/ $\mu M^{a)}$ | Vessel 3 Quantity/ $\mu M^{a)}$ | Vessel 4 Quantity/ $\mu M^{a}$ |
|---|---|---|---|---|---|
| 1 | [$^{13}C_5$]-Heroine | 0.2 | 1.0 | 5.0 | 20.0 |
| 2 | [$^{13}C_3$]-Ethylmorphine | 0.4 | 2.0 | 10.0 | 40.0 |
| 3 | [$^{13}C_6$]-Amphetamine | 0.4 | 2.0 | 10.0 | 40.0 |
| 4 | [$^{13}C_6$]-Methamphetamine | 0.4 | 2.0 | 10.0 | 40.0 |
| 5 | [$^{13}C_6$]-MDA | 0.4 | 2.0 | 10.0 | 40.0 |
| 6 | [$^{13}C_6$]-MDMA | 0.4 | 2.0 | 10.0 | 40.0 |
| 7 | [$^{13}C_6$]-DMEA | 0.4 | 2.0 | 10.0 | 40.0 |
| 8 | [$^{13}C_6$]-PMA | 0.4 | 2.0 | 10.0 | 40.0 |
| 9 | [$^{13}C_6$]-PMMA | 0.4 | 2.0 | 10.0 | 40.0 |
| 10 | [$^{13}C_6$]-7-Aminonitrazepam | 0.1 | 0.5 | 2.5 | 10.0 |
| 11 | [$^{13}C_6$]-7-Aminoclonazepam | 0.1 | 0.5 | 2.5 | 10.0 |
| 12 | [$^{13}C_6$]-7-Aminoflunitrazepam | 0.1 | 0.5 | 2.5 | 10.0 |
| 13 | [$^{13}C_6$]-Alprazolam | 0.1 | 0.5 | 2.5 | 10.0 |
| 14 | [$^{13}C_6$]-Oxazepam | 0.4 | 2.0 | 10.0 | 40.0 |
| 15 | [$^{13}C_6$]-Temazepam | 0.4 | 2.0 | 10.0 | 40.0 |
| 16 | [$^{13}C_6$]-Desmethyldiazepam | 0.4 | 2.0 | 10.0 | 40.0 |
| 17 | [$^{13}C_6$]-Adinazolam | 0.4 | 2.0 | 10.0 | 40.0 |
| 18 | [$^{13}C_6$]-Benzoylecgonine | 0.4 | 2.0 | 10.0 | 40.0 |
| 19 | [$^{13}C_6$]-Pentazocine | 0.4 | 2.0 | 10.0 | 40.0 |
| 20 | [$^{13}C_6$]-Zolpidem | 0.1 | 0.5 | 2.5 | 10.0 |
| 21 | [$^{13}C_6$]-6-MAM | 0.4 | 2.0 | 10.0 | 40.0 |
| 22 | [$^{13}C_4$]-THC-Acid | 0.05 | 0.25 | 1.25 | 5.0 |

In one embodiment the test kit of the invention comprises or contains at least one isotopologues selected from the group consisting of the below mentioned drugs respectively their isotopologues, preferably:

[$^{13}C_4$]-diacetyl morphine ([$^{13}C_4$]-heroine), [$^{13}C_5$]-diacetylmorphine ([$^{13}C_5$]-heroine), [$^{13}C_5$]-diacetylmorphine ([$^{13}C_5$]-heroine), [$^{13}C_3$]-3-acetylmorphine ([$^{13}C_3$]-3-MAM), [$^{13}C_3$]-6-acetylmorphine ([$^{13}C_3$]-6-MAM), [$^{13}C_3$]-3-ethylmorphine, [$^{13}C_4$]-buprenorphine, [$^{13}C_4$]-buprenorfine, [$^{13}C_6$]-(-)-cocaine, [$^{13}C_6$]-(-)-benzoylecgonine, [$^{13}C_4$]-Δ9-THC, [$^{13}C_6$]-Δ9-THC, [$^{13}C_6$]-(-)-Δ9-THC acid, [$^{13}C_6$]-nitrazepam, [$^{13}C_6$]-7-aminonitrazepam, [$^{13}C_6$]-clonazepam, [$^{13}C_6$]-7-aminoclonazepam, [$^{13}C_6$]-flunitrazepam, [$^{13}C_6$]-flunitrazepam, [$^{13}C_6$]-7-aminoflunitrazepam, [$^{13}C_6$]-desmethyldiazepam, [$^{13}C_6$]-diazepam, [$^{13}C_6$]-alprazolam, [$^{13}C_6$]-oxazepam, [$^{13}C_6$]-temazepam, [$^{13}C_6$]-zolpidem, [$^{13}C_5$]-JWH-073, DL-[$^{13}C_6$]-amphetamine, DL-[$^{13}C_6$]-methamphetamine and its chloride salt, DL-[$^{13}C_6$]-3,4-methylenedioxyamphetamine hydrochloride (MDA HCl), DL-[$^{13}C_6$]-3,4-methylenedioxy-N-methylamphetamine hydrochloride (DL-[$^{13}C_6$]-MDMA HCl), DL-[$^{13}C_6$]-3,4-methylenedioxy-N-ethylamphetamine hydrochloride (DL-[$^{13}C_6$]-MDEA hydrochloride), DL-[$^{13}C_6$]-4-methoxy-amphetamine hydrochloride (DL-[$^{13}C_6$]-PMA HCl), [$^{13}C_6$]-anisole, DL-[$^{13}C_6$]-4-methoxymethamphetamine hydrochloride (DL-[$^{13}C_6$]-PMMA HCl);

the isotopologues according to Table A;

the isotopologues as mentioned below; and/or their salts, solvates, hydrates and polymorphs and/or derivatives with increased hydrophilicity, preferably glucuronides.

In one embodiment the test kit is "ready to use", e.g. no further preparation of the vessels is necessarily.

The isotopologue of the test kit can be directly added to the analytical sample or the biological specimen is added to the vessel of the kit and the sample is analyzed directly, instantaneously.

In one embodiment the test kit of the invention comprises or contains any combination of isotopologues or of the kits mentioned.

Examples of suitable benzodiazepines are the following:
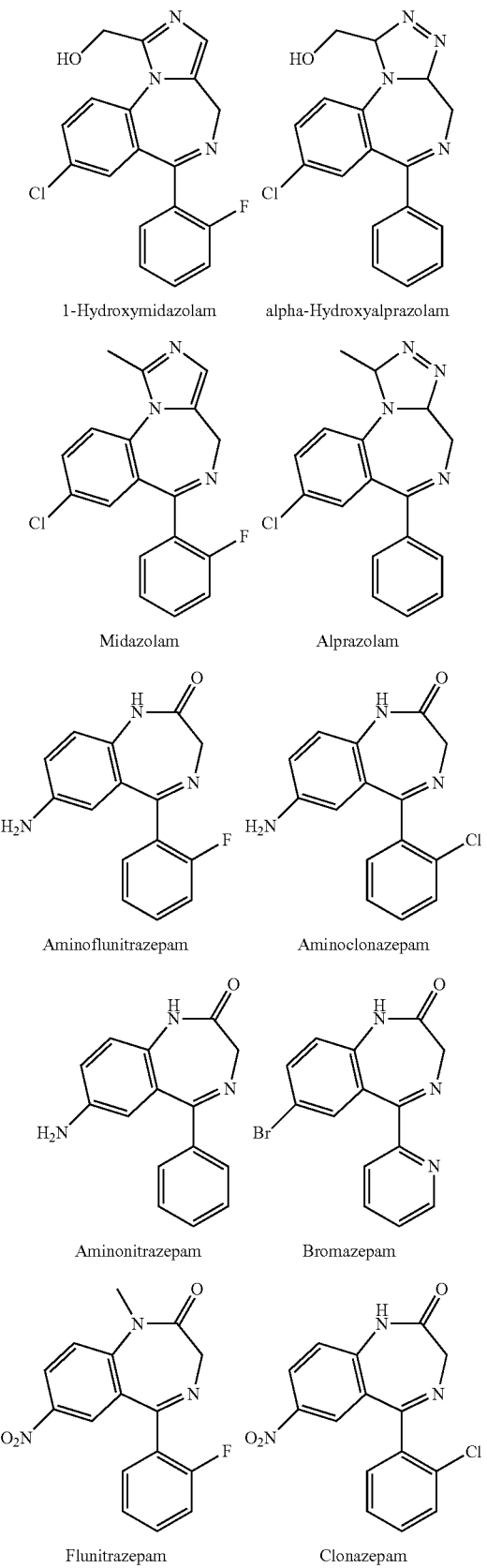
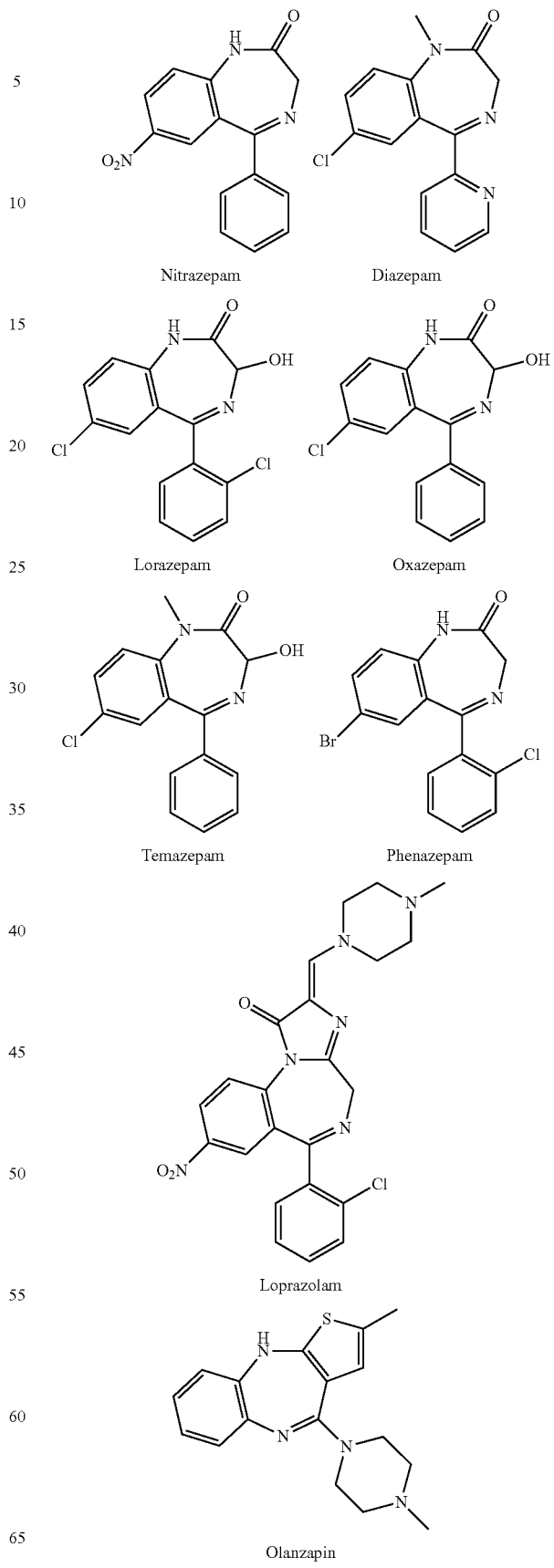

-continued

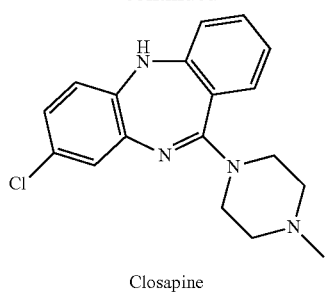

Closapine

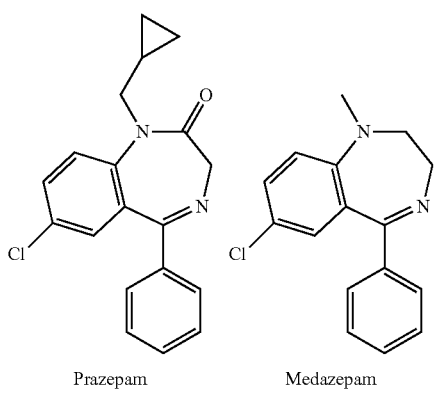

Prazepam        Medazepam

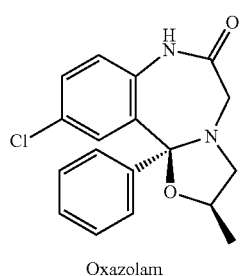

Oxazolam

The isotopologues of the benzodiazepines having at least three, preferably at least four, more preferably at least five and most preferably six $^{13}C$ isotopes can be synthesized by well-known methods of preparing benzodiazepines using suitable educts having at least three, preferably at least four, more preferably at least five and most preferably six $^{13}C$ isotopes.

Preferably, the isotopologues of the benzodiazepines wherein the seven-membered ring is substituted by a substituted or an unsubstituted phenyl group are used. Examples of such preferable benzodiazepines are 1-hydroxymidazolam, adinazolam, alphahydroxyprazolam, alprazolam, aminoclonazepam, aminoflunitrazepam, aminonitrazepam, bromazepam, clonazepam, diazepam, flunitrazepam, loprazolm, lorazepam, medazepam, midazolam, nitrazepam, oxazepam, phenazepam, prazepam and temazepam.

Most preferably, the six $^{13}C$ isotopes are located in an aromatic ring, in particular the substituted or unsubstituted phenyl ring, by which the seven-membered is substituted.

They can be prepared by the following general synthetic methods set out in the Scheme 1 using suitable substituted [ring-$^{13}C_6$]-benzenes.

Scheme 1: General Synthetic Methods for Synthesizing the Isotopologues of Preferred Benzodiazepines Method 1:

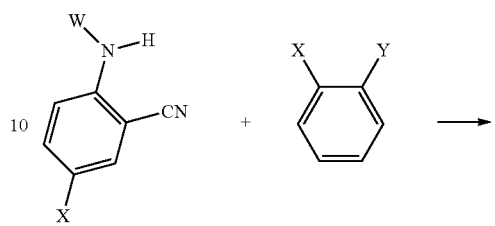

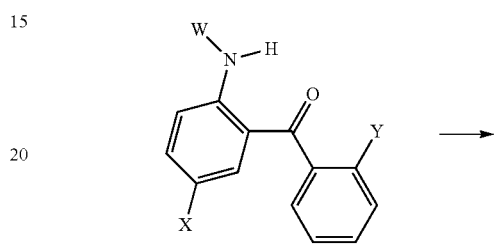

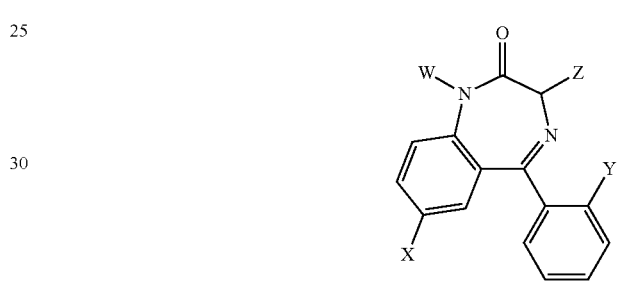

Method 2:

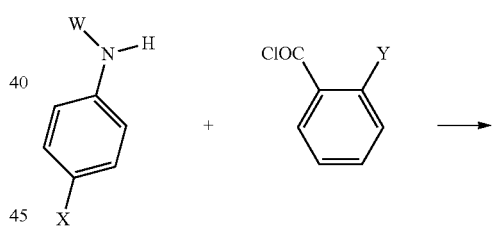

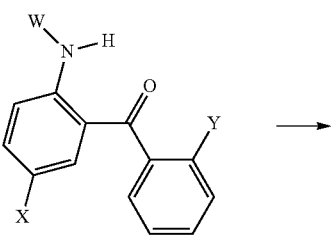

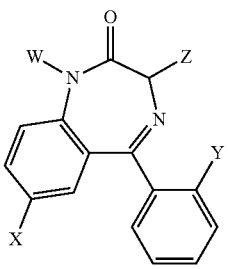

Method 3:

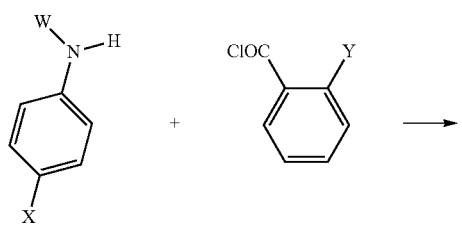

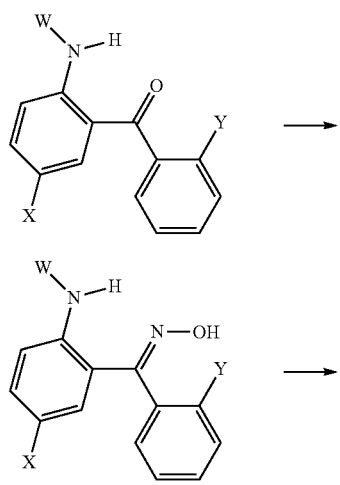

Method 4:

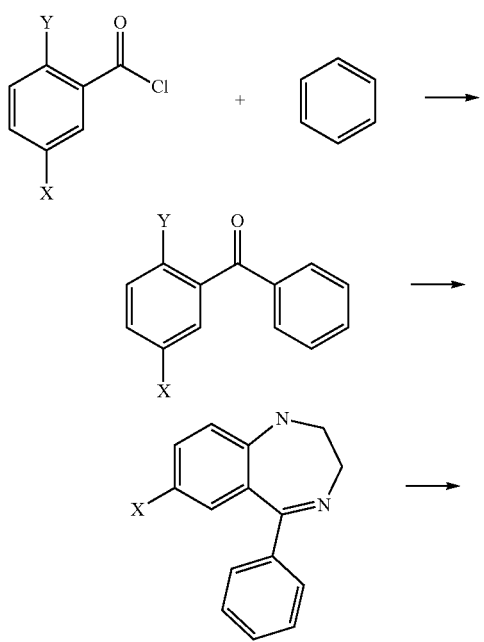

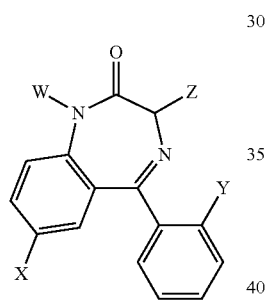

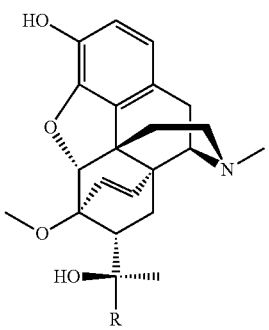

In the Scheme 1, the variables R, X, Y and Z have the following meaning:
W=—H, —CH₃, cyclopropylmethyl, etc.
X=—NO₂, —NH₂, halogen, etc.
Y=—H, halogen, etc.
Z=—H, —OH, etc, Reference is also made to the article of R. S. Hsi and L. S. Stelzer, Synthesis of Adinazolam multiply labeled with Carbon-13 and Deuterium, in Journal of Labelled Compounds in Radiopharmaceuticals, Volume XXVII, No. 3, 287-295, 1989.

Examples of suitable morphines (opiates) are the following:

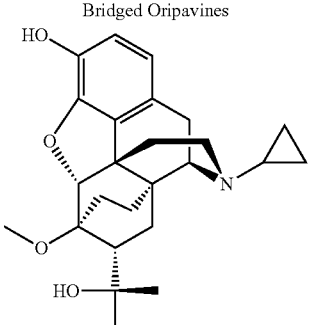

Bridged Oripavines

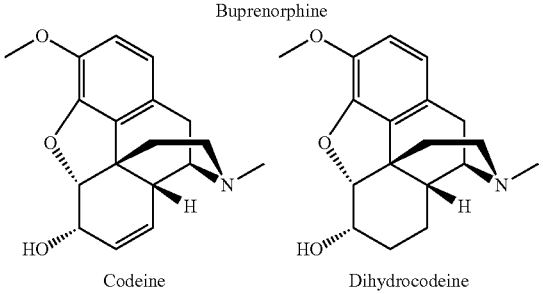

Buprenorphine

Codeine          Dihydrocodeine

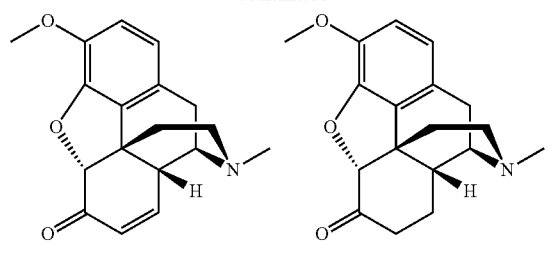
Codeinone  Dihydrocodeinone
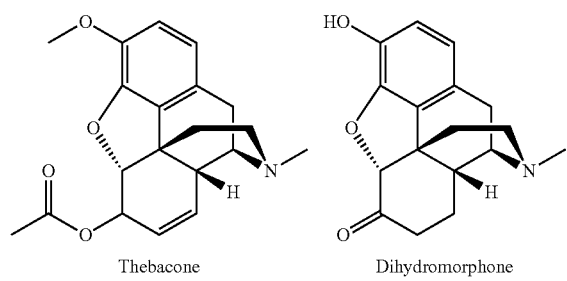
Thebacone  Dihydromorphone
Ethylmorphine
6-Monacetylmorphine
3-monacetylmorphine  Morphinone
Morphine  Nalbuphine
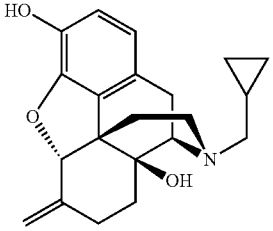
Nalmafene
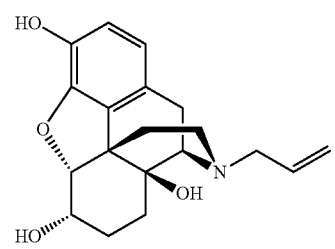
Nalorphine
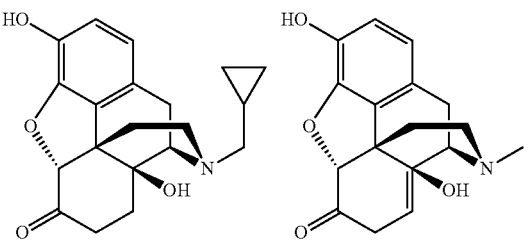
Naltrexone  Neopinone
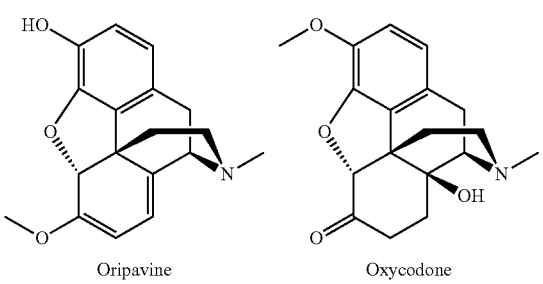
Oripavine  Oxycodone
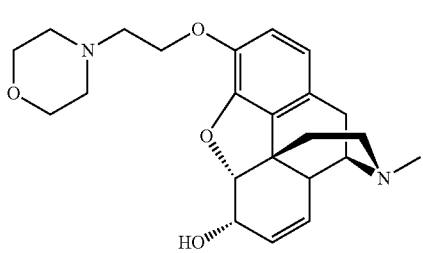
Pholcodine
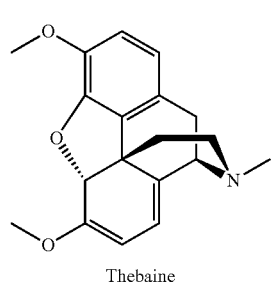
Thebaine

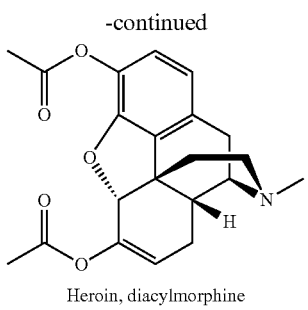

Heroin, diacylmorphine

The isotopologues of the morphines can be synthesized by methods well-known in the art thereby using suitable $^{13}C$ labeled educts such as 1,1',2,2'-[$^{13}C_4$]-acetic anhydride, $^{13}C$-iodomethane, [$^{13}C_2$]-iodoethane, [$^{13}C_4$]-methylvinylketone and/or [$^{13}C_3$]-allyl derivatives.

Examples of suitable piperazines are [$^{13}C_6$]-benzene and [$^{13}C_4$]-piperazine derivatives such as the isotopologues of 1-benzylpiperazine (BZP), 1-methyl-4-benzylpiperazine (MBZP), 1,4-dibenzylpiperazine (DBZP); 3-chlorophenylpiperazine (mCPP), 4-chlorophenylpiperazine (pCPP), methoxyphenylpiperazine MeOPP), 3.trifluoromethylphenylpiperazine (TFMPP), 3,4-methylenedioxy-1-benzylpiperazine (MDBZP), 4-bromo-2,5-dimethoxy-1-benzylpiperazine (2C-B-BZP), and 4-fluorophenylpiperazine (pFPP).

The isotopologues of the piperazines can be synthesized by methods well known in the art, thereby using $^{13}C$ labeled educts, preferably substituted [$^{13}C_6$]-benzene derivatives.

Cannabinoids

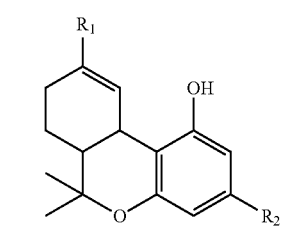

$R_1 = CH_3, R_2 = (CH_2)_4—CH_3: D_9—THC$
$R_1 = CH_2OH, R_2 = (CH_2)_4—CH_3: 11\text{-}OH—D_9—THC$
$R_1 = COOH, R_2 = (CH_2)_4—CH_3: D_9—THC—COOH$
$R_1 = CH_3, R_2 = (CH_2)_2—CH_3: D_9—THCV$
$R_1 = CH_2OH, R_2 = (CH_2)_2—CH_3: 11\text{-}OH—D_9—THCV$
$R_1 = COOH, R_2 = (CH_2)_2—CH_3: D_9—THCV—COOH$

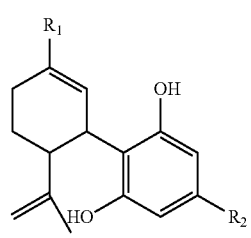

$R_1 = CH_3, R_2 = (CH_2)_4—CH_3$: Cannabidiol, CBN
$R_1 = CH_3, R_2 = (CH_2)_2—CH_3$: Cannabidivarin, CBV

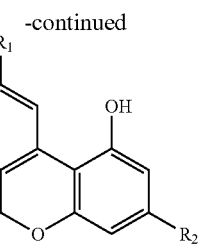

$R_1 = CH_3, R_2 = (CH_2)_4—CH_3$: Cannabinol, CBD
$R_1 = CH_3, R_2 = (CH_2)_2—CH_3$: Cannabivarin, CBDV

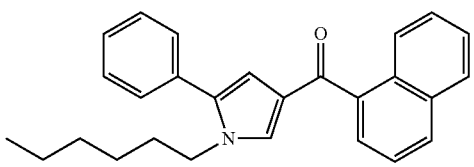

$R_1 = CH_3, R_2 = (CH_2)_4—CH_3: D_8—THC$
$R_1 = CH_2OH, R_2 = (CH_2)_4—CH_3: 11\text{-}OH—D_8—THC$
$R_1 = COOH, R_2 = (CH_2)_4—CH_3: D_8—THC—COOH$
$R_1 = CH_3, R_2 = (CH_2)_2—CH_3: D_8—THCV$
$R_1 = CH_2OH, R_2 = (CH_2)_2—CH_3: 11\text{-}OH—D_8—THCV$
$R_1 = COOH, R_2 = (CH_2)_2—CH_3: D_8—THCV-COOH$ The isotopologues of the cannabinoids can be synthesized methods well-known in the art, thereby using $^{13}C$ labeled educts, in particular [$^{13}C_4$]-butyl bromide, 4-(3,5-dimethoxyphenyl)-1-[$^{13}C4$]-pentane and [$^{13}C_4$]-olivetol.

An example before a suitable naphthoylpyrrol is

JWH-147

The isotopologues of naphthylpyrrols can be synthesized by methods well-known in the art, thereby using $^{13}C$ labeled educts, as for example, $^{13}C$ labeled benzene derivatives and $^{13}C$ labeled alkyl iodides.

Examples of suitable naphthoylindoles (aminonaphthoylindoles; SPICE) are the following:

JWH-193
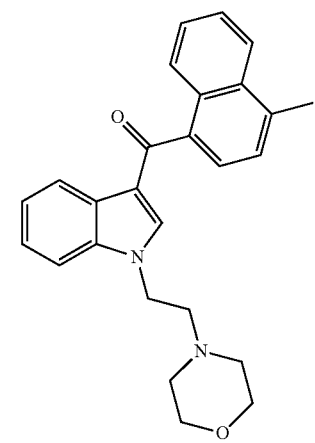
JWH-398
JWH-424
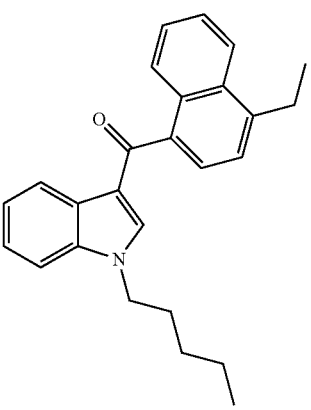
JWH-018
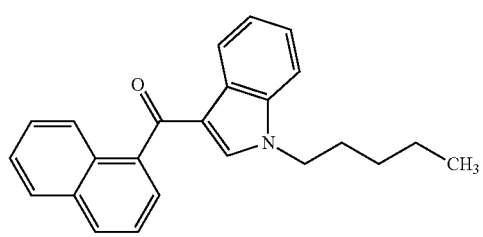
(synthetic cannabis "SPICE")
-continued
AM-2201
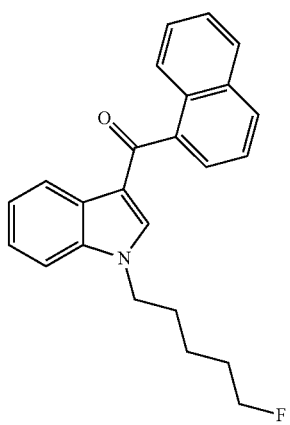
JWH-073
JWH-210
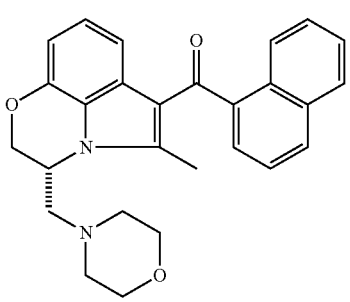
WIN 55,212-2-2D
The isotopologues of the naphthoylindoles can also be prepared by methods well-known in the art, thereby using $^{13}C$ labeled educts such as $[^{13}C_8\text{-}^{15}N]$-indole and $^{13}C$ labeled alkyl iodides.

Examples of suitable SPICE components are

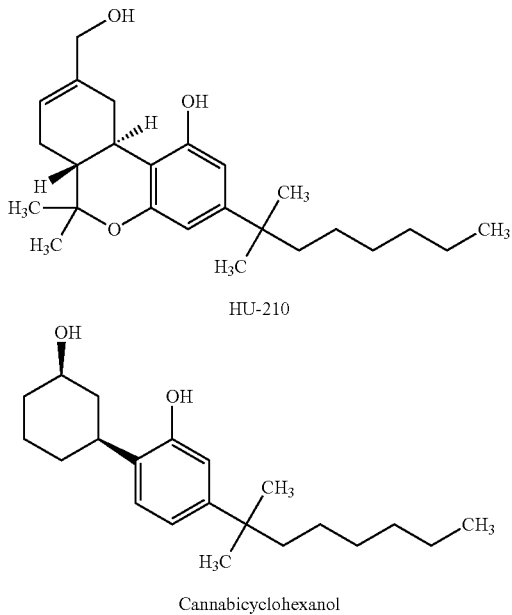

HU-210

Cannabicyclohexanol

For further details reference is made to in the article in the Frontiers of Behavioral Neuroscience September 2011, Volume 5, article 50.

The isotopologues of SPICE components can also be prepared by methods well-known any art, thereby using $^{13}C$ labeled adducts.

Examples for suitable isotopologues of cocaine and its derivatives are $[^{13}C_6]$-cocaine, $[^{13}C_4]$-cocaine, $[^{13}C_6]$-benzoylecgonine and $[^{13}C_4]$-benzoylecgonine. The isotopologues can be synthesized by methods well-known in the art, thereby using labeled educts such as [ring-$^{13}C_6$]-benzoyl chloride, $[^{13}C_4]$-succinic acid anhydride, $[^{13}C_4]$-succinic acid and $[^{13}C_4]$-succinic aldehyde.

Examples of suitable amphetamines are amphetamine, methamphetamine, 3,4-methylenedioxyamphetamine, 3,4-methylenedioxy-N-methylamphetamine, 3,4-methylenedioxy-N-ethylamphetamine, 3-methoxy-4,5-methylenedioxyamphetamine, 2,5-dimethoxy-4-methylamphetamine, macromerine, normacromerine, cathinone, cathine, methcathinone, ethcatinone, mephedrone (2-methylamino-1(4-methylphenyl)propan-1-one), 1-(2-fluorophenyl)-2-methylaminopropan-1-one, 1-(3-fluorophenyl)-2-methylaminopropan-1-one, 1-(4-fluorophenyl)-2-methylaminopropan-1-one, 2-methylamphetamine, 3-methylamphetamine, 4-methylamphetamine, 2-methylmethamphetamine, 3-methylmethamphetamine, 4-methylmethamphetamine, 2-methoxylamphetamine, 3-methoxyamphetamine, 4-methoxyamphetamine, 2-methoxymethamphetamine, 3-methoxymethamphetamine, 4-methoxymethamphetamine, 2-fluoroamphethamine, 3-fluoroamphethamine, 4-fluoroamphethamine, 2-fluoromethamphethamine, 3-fluoromethamphethamine, 4-fluoromethamphethamine, 3,4,5-trimethoxy-2-methylamphetamine, 2,4,5-, 3,4,5-, 2,3,4- 2,3,5-, 2,3,6- and 2,4,6-trimethoxyamphetamine; 2,4,5-, 3,4,5-, 2,3,4- 2,3,5-, 2,3,6- and 2,4,6-trimethoxyphenylethylamine, 2,5-dimethoxy-4-amyl-, 2,5-dimethoxy-4-bromo-, 2,5-dimethoxy-4-butyl-, 2,5-dimethoxy-4-chloro-, 2,5-dimethoxy-4-ethyl-, 2,5-dimethoxy-4-fluoro-, 2,5-dimethoxy-4-(2-fluoroethyl)-2,5-dimethoxy-4-iodo-, 2,5-dimethoxy-4-methyl-, 2,5-dimethoxy-4-nitro-, 2,5-dimethoxy-4-trifluoromethyl-, 2,5-dimethoxy-4-ethoxy-, 2,5-dimethoxy-4-methylthio-, 2,5-dimethoxy-4-ethylthio-, 2,5-dimethoxy-4-isopropylthio-, 2,5-dimethoxy-4-phenylthio- and 2,5-dimethoxy-4-propylthioamphetamine; 2,5-dimethoxy-3,4-dimethyl-, 2,5-dimethoxy-3,4-prop-1,3-ylen-, 2,5-dimethoxy-3,4-but-1,4-yen, 2,5-dimethoxy-3-isopropyoxy-, 2,5-dimethoxy-3-propyl-, 2,5-dimethoxy-methylseleno-, 2,5-dimethoxypropylthio-, 2,5-dimethoxy-3-cyclopropylmethylthio-, 2,5-dimethoxy-3-n-butylthio-, 2,5-dimethoxy-3-(2-methoxyeth-1-yl)thio-, 2,5-dimethoxy-3-cyclopropylthio-, 2,5-dimethoxy-3-(1-methyl-prop-1-yl)thio-, 2,5-dimethoxy-3-(2-fluoroeth-1-yl)thioamphetamine; 2-(4-bromo-2,5-dimethoxyphenyl)ethanamine, 1-(4-chloro-2,5-dimethoxyphenyl)-2-aminoethane, 1-(2,5-dimethoxy-4-methylphenyl)-2-aminoethane, 1-(2,5d-4-ethylphenyl)-2-aminoethane, 2-(4-fluoro-2,5-dimethoxyphenyl)-1-aminoethane, 3,4-dimethyl-2,5-dimethoxyphenethylamine, 5-(2-aminoethyl)-4,7-dimethoxyindane, 1,2,3,4-tetrahydro-5,8-dimethoxy-1,4-methanonaphthalene-6-ethanamine, 1,4-dimethoxy-2-naphthaleneethanamine, 2-(2,5-dimethoxyphenyl)ethanamine, 2,5-dimethoxy-4-iodophenethylamine, 2,5-dimethoxy-4-nitrophenethylamine, 2-(2,4,5-trimethoxyphenyl)ethanamine, 2-(4-isopropoxy-2,5-dimethoxyphenyl)ethanamine, 2-(2,5-dimethoxy-4-propylphenyl)ethanamine, 2-(2,5-dimethoxy-4-(methylthio)phenyl)ethanamine, 2-[4-(ethylthio)-2,5-dimethoxyphenyl]ethanamine, 2-[4-(isopropylthio)-2,5-dimethoxyphenyl]ethanamine, 2-[2,5-dimethoxy-4-(propylthio)phenyl]ethanamine, 2-[4-[(cyclopropylmethyl)thio]-2,5-dimethoxyphenyl]ethanamine, 2-[4-(butylthio)-2,5-dimethoxyphenyl]ethanamine, 2-[4-(methoxyethylthio)-2,5-dimethoxyphenyl]ethanamine, 2-[4-(cyclopropylthio)-2,5-dimethoxyphenyl]ethanamine, 2-[4-(isobutylthio)-2,5-dimethoxyphenyl]ethanamine, 2-[2,5-dimethoxy-4-(2-fluoroethylthio)phenyl]ethanamine, 2,5-dimethoxy-4-(trifluoromethyl)phenethylamine, 1-amino-2-(1,4-naphth-2-yl)amphetamine, 3,6-dimethoxy-5-ethylthioamphetamine, 4-methyl-5-phenyl-2-amino-oxazoline (4-methylaminorex); 5-phenyl-2-amino-oxazoline (aminorex), 2,5-dimethoxy-3, 4-methylenedioxyamphethamine (DMMDA). in particular amphetamine, methamphetamine, 3,4-methylenedioxyamphetamine, and 3,4-methylenedioxy-N-ethylamphetamine (ecstasy).

Examples of suitable isotopologues of amphetamines are $[^{13}C_6]$-amphetamine, -methamphetamine, -3,4-methylenedioxyamphetamine, -3,4-methylenedioxy-N-methylamphetamine, -3,4-methylenedioxy-N-ethylamphetamine, -3-methoxy-4,5-methylenedioxyamphetamine, -2,5-dimethoxy-4-methylamphetamine, -macromerine, -normacromerine, -cathinone, -cathine, -methcathinone, -ethcatinone, mephedrone-(2-methylamino-1(4-methylphenyl)propan-1-one), -1-(2-fluorophenyl)-2-methylaminopropan-1-one, -1-(3-fluorophenyl)-2-methylaminopropan-1-one, -1-(4-fluorophenyl)-2-methylaminopropan-1-one, -2-methylamphetamine, -3-methylamphetamine, -4-methylamphetamine, 2-methylmethamphetamine, -3-methylmethamphetamine, -4-methylmethamphetamine, -2-fluoroamphethamine, -3-fluoroamphethamine, -4-fluoroamphethamine, -2-fluoromethamphethamine, -3-fluoromethamphethamine, -[4-fluoromethamphethamine, -3,4,5-trimethoxy-2-methylamphetamine, -2,4,5-, -3,4,5-, -2,3,4- -2,3,5-, -2,3,6- and -2,4,6-trimethoxyamphetamine; -2,4,5-, -3,4,5-, -2,3,4- -2,3,5-, -2,3,6- and -2,4,6-trimethoxyphenylethylamine, -2,5-dimethoxy-4-amyl-, -2,5-dimethoxy-4-bromo-, -2,5-dimethoxy-4-butyl-, 2,5-dimethoxy-4-chloro-, -2,5- dimethoxy-4-ethyl-, -2,5-dimethoxy-4-fluoro-, -2,5-dimethoxy-4-(2-fluoroethyl)-, -2,5-dimethoxy-4-iodo-, -2,5-dimethoxy-4-methyl-, -2,5-dimethoxy-4-nitro-, -2,5-dimethoxy-4-trifluoromethyl-, -2,5-dimethoxy-4-ethoxy-, -2,5-dimethoxy-4-methylthio-, -2,5-dimethoxy-4-ethylthio-, -2,5-dimethoxy-4-isopropylthio-, -2,5-dimethoxy-4-phenylthio- and -2,5-dimethoxy-4-propylthioamphetamine; -2,5-dimethoxy-3,4-dimethyl-, -2,5-dimethoxy-3,4-prop-1,3-ylen-, -2,5-dimethoxy-3,4-but-1,4-ylen, -2,5-dimethoxy-3-isopropyoxy-, -2,5-dimethoxy-3-propyl-, -2,5-dimethoxy-methylseleno-, -2,5-dimethoxy-propylthio-, -2,5-dimethoxy-3-cyclopropylmethylthio-, -2,5-dimethoxy-3-n-butylthio-, -2,5-dimethoxy-3-(2-methoxyeth-1-yl)thio-, -2,5-dimethoxy-3-cyclopropylthio-, -2,5-dimethoxy-3-(1-methyl-prop-1-yl)thio- and -2,5-dimethoxy-3-(2-fluoroeth-1-yl)thioamphetamine; -1-amino-2-(1,4-naphth-2-yl)ethane, -3,6-dimethoxy-5-ethylthioamphetamine, -2-(4-bromo-2,5-dimethoxyphenyl)ethanamine, -1-(4-Chloro-2,5-dimethoxyphenyl)-2-aminoethane, -1-(2,5-dimethoxy-4-methylphenyl)-2-aminoethane, -1-(2,5-dimethoxy-4-ethylphenyl)-2-aminoethane, -2-(4-fluoro-2,5-dimethoxyphenyl)-1-aminoethane, -3,4-dimethyl-2,5-dimethoxyphenethylamine, -5-(2-aminoethyl)-4,7-dimethoxyindane, -1,2,3,4-tetrahydro-1,9,8-dimethoxy-1,4-methanonaphthalene-6-ethanamine, -1,4-dimethoxy-2-naphthaleneethanamine, -2-(2,5-dimethoxyphenyl)ethanamine, -2,5-dimethoxy-4-iodophenethylamine, 2,5-dimethoxy-4-nitrophenethylamine, -2-(2,4,5-trimethoxyphenyl)ethanamine, -2-(4-Isopropoxy-2,5-dimethoxyphenyl)ethanamine, -2-(2,5-dimethoxy-4-propylphenyl)ethanamine, -2-(2,5-dimethoxy-4-(methylthio)phenyl)ethanamine, -2-[4-(ethylthio)-2,5-dimethoxyphenyl]ethanamine, -2-[4-(isopropylthio)-2,5-dimethoxyphenyl]ethanamine, -2-[2,5-dimethoxy-4-(propylthio)phenyl]ethanamine, -2-[4-[(cyclopropylmethyl)thio]-2,5-dimethoxyphenyl]ethanamine, -2-[4-(butylthio)-2,5-dimethoxyphenyl]ethanamine, -2-[4-(methoxyethylthio)-2,5-dimethoxyphenyl]ethanamine, -2-[4-(cyclopropylthio)-2,5-dimethoxyphenyl]ethanamine, -2-[4-(isobutylthio)-2,5-dimethoxyphenyl]ethanamine, -2-[2,5-dimethoxy-4-(2-fluoroethylthio)phenyl]ethanamine, -2,5-dimethoxy-4-(trifluoromethyl)phenethylamine, -5-phenyl-2-aminooxazoline (-aminorex) and 4-methyl-5-phenyl-2-aminooxazoline (4-methylaminorex), and -2,5-dimethoxy-3,4-methylenedioxyamphethamine (DMMDA); in particular [$^{13}C_6$]-amphetamine, [$^{13}C_6$]-methamphetamine, [$^{13}C_6$]-3,4-methylenedioxyamphethamine, [$^{13}C_6$]-3,4-methylenedioxy-N-ethylamphetamine (ecstasy) and [$^{13}C_6$]-3,4-methylenedioxy-N-methylamphetamine.

The isotopologues of the amphetamines can be prepared by methods well-known in the art, thereby using $^{13}C$ labeled educts such as [$^{13}C_6$]-benzaldehyde or substituted [$^{13}C_6$]-benzaldehyde.

Examples of suitable benzazocines are benzomorphane, 5,9-DEHB (5,9-alpha-diethyl-2'-hydroxybenzomorphane, 8-CAC (8-carboxamidocyclazocine), alazocine, anazocine, bremazocine, butinazocine, carbazocine, cogazocine, cyclazocine, dezocine, eptazocine, etazocine, ethylketocycazocine, fluorophen, gemazocine, ibazocine, ketazocine, metazocine, moxazocine, pentazocine, phenazocine, quadazocine, thiazocine, tonazocine, volazocine and zenazocine.

[$^{13}C_4$]-Heroin, [$^{13}C_5$]-heroin, [$^{13}C_6$]-heroin, [$^{13}C_3$]-3-acetylmorphine, [$^{13}C_3$]-6-acetylmorphine, [$^{13}C_3$]-3-ethylmorphine, [$^{13}C_4$]-buprenorphine (labeling in the tert.-butyl sidechain), [$^{13}C_6$]-(−)-cocaine, [$^{13}C_6$]-(−)-benzoylecgonine, [$^{13}C_4$]-Δ9-THC, [$^{13}C_4$]-(−)-Δ9-THC acid, [$^{13}C_6$]-nitrazepam, [$^{13}C_6$]-7-aminonitrazepam, [$^{13}C_6$]-clonazepam, [$^{13}C_6$]-7-aminoclonazepam, [$^{13}C_6$]-flunitrazepam, [$^{13}C_6$]-7-aminoflunitrazepam, [$^{13}C_6$]-desmethyldiazepam, [$^{13}C_6$]-diazepam, [$^{13}C_6$]-alprazolam, [$^{13}C_6$]-oxazepam, [$^{13}C_6$]-adinazolam, [$^{13}C_6$]-temazepam, [$^{13}C_6$]-zolpidem, [$^{13}C_5$]-JWH-073, DL-[$^{13}C_6$]-amphetamine, DL-[$^{13}C_6$]-methamphetamine, DL-[$^{13}C_6$]-3,4-methylenedioxyamphetamine, DL-[$^{13}C_6$]-3,4-methylenedioxy-N-methylamphetamine, DL-[$^{13}C_6$]-3,4-methylenedioxy-N-ethylamphetamine, DL-[$^{13}C_6$]-4-methoxyamphetamine, DL-[$^{13}C_6$]-4-methoxymethamphetamine, and [$^{13}C_6$]-pentazocine are preferably used.

According to the use of the invention, the test kit of the invention is excellently suited for the chemical analysis and metabolic studies of narcotic drugs. In particular, it is excellently suited for the chemical analysis and for the metabolic studies of the non-labeled isotopologues, i.e., the narcotic drugs themselves, which correspond to the deuterium free isotopologues contained in the appropriate test kit of the invention. Most particularly, the $^{13}C$ labeled isotopologues of the test kit of the invention are excellently suited as standards, in particular as internal standards, in the quantitative chemical analysis of their corresponding non-labeled narcotic drugs by LC-MS, GC-MS, LC-tandem MS and GC-tandem MS. Therefore, the test kit and the use of the invention are most excellently suited for the quantitative forensic chemical analysis of biological samples, in particular body fluids and dispersed solid body materials, in particular blood, saliva, bile or urine, especially urine. This way, the illicit use of hallucinogens and/or stimulants can be easily detected quantitatively with a high accuracy and an excellent reproducibility. A The test kit can also be used by anti-doping authorities.

Moreover, the test kit of the invention is excellently suited for the calibration of the analytical methods used.

The method of the invention comprises the steps of
(1) identifying the narcotic drug to be quantitatively determined in an analytical sample;
(2) selecting the sealed vessel or vessels containing the corresponding deuterium free isotopologue of the narcotic drug from the test kit of the invention;
(3) adding the deuterium free isotopologue to the analytical sample as a standard, preferably internal standard, or adding an amount, preferably the same amount of the biological specimen, e.g. body fluid to each vessel of the test kit; and
(4) quantitatively determining the narcotic drug in the analytical sample with a suitable analytical method.

EXAMPLES

Example 1

Synthesis of [$^{13}C_4$]-diacetyl morphine ([$^{13}C_4$]-heroine)

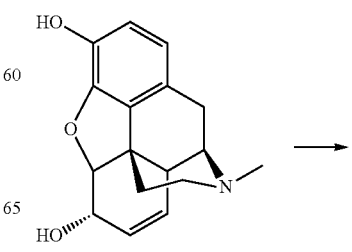

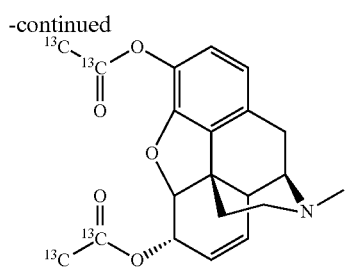

Morphine hydrochloride (0.5 g, 1.56 mmol) was dissolved in a mixture of pyridine (15 mL) and 1,1',2,2'-[$^{13}C_4$]-acetic anhydride (20 mL). The solution was stirred at room temperature for 24 hours, then poured on ice, washed with 10% sodium bicarbonate (50 mL) and extracted with chloroform (3×50 mL). The organic layers were combined, washed with water and dried over MgSO$_4$. The solvent was partially evaporated and diethyl ether was added. After cooling, the white solid was filtered, washed and dried, yielding 431 mg [$^{13}C_4$]-morphine diacetate (97% yield).

Example 2

Synthesis of [$^{13}C_5$]-diacetylmorphine ([$^{13}C_5$]-heroine)

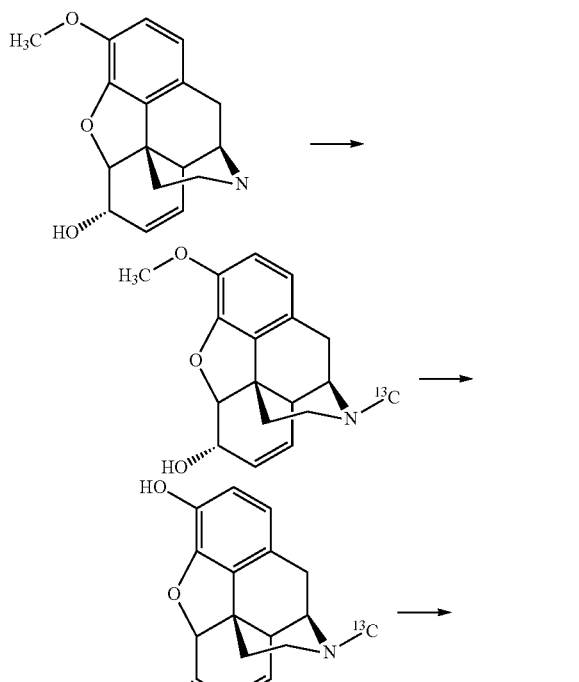

2.1 Synthesis of [$^{13}C_1$]-codeine

Norcodeine (0.76 g, 2.67 mmol), potassium carbonate (1.55 g, 10.6 mmol) and tetra-n-butylammonium bromide (0.86 g, 2.67 mmol) were mixed in dry toluene (50 ml), and the mixture was warmed to 110° C. A solution of iodomethane-$^{13}C_1$ (0.4 g, 2.81 mmol) in 10 ml of toluene was dropped in. The reaction mixture was stirred at 110° C. overnight, and was then cooled to room temperature. The two layers were separated, the water phase was extracted with toluene, and the combined organic phases were washed with water and dried over sodium sulfate. After sodium sulfate and the solvent were removed, the crude [$^{13}C_1$]-codeine was purified by preparative HPLC to give 450.5 mg (55.9% yield) pure product.

2.2 Synthesis of [$^{13}C_1$]-morphine

[$^{13}C_1$]-Codeine (N-methyl $^{13}C$, 400 mg, 1.32 mmol) was heated with pyridine hydrochloride for 5 hours. The reaction mixture was diluted with water. 4N NaOH solution was added until pH 8-9, and the mixture was extracted with chloroform to remove non-phenolic material. The aqueous phase was acidified and extracted twice with chloroform. The combined chloroform extracts were dried over Na$_2$SO$_4$, filtered and evaporated to dryness. Crude [$^{13}C_1$]-morphine was purified by sublimation yielding 226.5 mg (60.2% yield).

2.3 Synthesis of [$^{13}C_5$]-diacetylmorphine ([$^{13}C_5$]-heroine)

[$^{13}C_1$]-Morphine hydrochloride (0.5 g, 5.22 mmol) was dissolved in a mixture of dry pyridine (30 mL) and then flushed with argon. 1,2-[$^{13}C_2$]-acetyl chloride (0.8 g, 9.9 mmol) was added slowly. The reaction temperature was then raised to 80° C. and after one hour a new portion of 1,2-[$^{13}C_2$]-acetyl chloride was added and the reaction was stirred at 80° C. overnight. The mixture was cooled on an icebath and quenched by addition of NaHCO$_3$ (50 mL). The organic phase was separated and the water phase was extracted twice by addition of dichloromethane (2×25 mL). The organic phases were combined, washed with water, and dried over magnesium sulphate. Evaporation of the solvent yielded [$^{13}C_5$]-diacetylmorphine as a clear semisolid (1.5 g). Ether (4 mL) and ethanol (10 mL) were added, and the product was crystallized as fine crystals, washed with diethyl ether, and dried; yield: 1.15 g (59%) free base of [$^{13}C_5$]-diacetylmorphine.

Example 3

Synthesis of [$^{13}C_3$]-3-acetylmorphine ([$^{13}C_3$]-3-MAM)

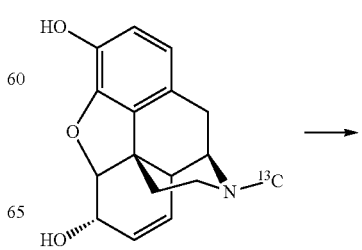

-continued

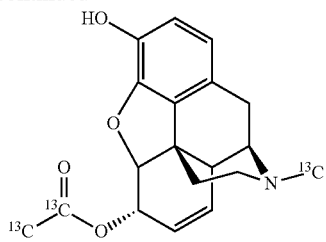

[$^{13}C_1$]-Morphine (0.5 g, 1.75 mmol) was suspended in dry dichloromethane (30 mL). Triethylamine (0.44 g, 4.38 mmol) was added in one portion whereupon the morphine base dissolved. 1,2-[$^{13}C_2$]-acetyl chloride (1.42 mg, 1.77 mmol) in dry dichloromethane (10 mL) was added slowly to the reaction mixture. The reaction was kept at ambient temperature for 30 minutes and the refluxed for another 30 minutes before cooling in an icebath and quenching with a saturated solution of NaHCO$_3$ (50 mL). The organic phase was separated and the water phase extracted with two portions of dichloromethane (2×25 mL). The combined organic phases were washed with water (50 mL) and dried over MgSO$_4$. Evaporation of the solvent yielded the product as a clear oil. Diethyl ether was added and the compound crystallized upon cooling. The product was separated from impurities of diacetylmorphine by filtration; yield 522.9 mg (89%) [$^{13}C_3$]-3-acetylmorphine (3-MAM).

Example 4

Synthesis of [$^{13}C_3$]-6-acetylmorphine ([$^{13}C_3$]-6-MAM)

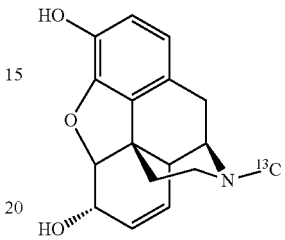

[$^{13}C_5$]-Heroine (150 mg, 0.4 mmol) was dissolved in ethanol (20 mL) and hydroxyammonium chloride (300 mg, 4.32 mmol) was added. The reaction mixture was stirred at room temperature for 20 hours. After evaporation of the solvent, the residue was dissolved in saturated sodium bicarbonate solution and extracted with chloroform (3×50 mL). The combined organic extracts were washed with water, dried over NaSO4, filtered and taken to dryness. The crude product was purified by recrystallization from diethyl ether yielding 148.90 mg [$^{13}C_3$]-6-MAM (99% yield).

Example 5

Synthesis of [$^{13}C_3$]-3-ethylmorphine

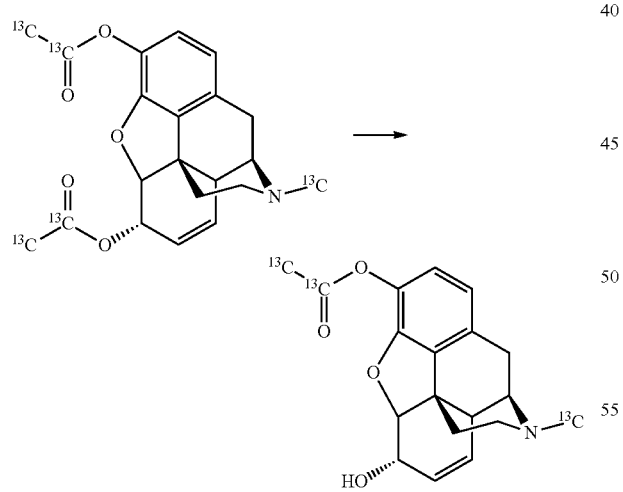

[$^{13}C_1$]-Morphine (N-methyl $^{13}C$), 0.15 g, 0.52 mmol), potassium carbonate (0.29 g, 2.01 mmol), and tetraammonium bromide (0.17 g, 5.26 mmol) were added to toluene (10 ml) and the mixture was heated to 110° C. A solution of [$^{13}C_2$]-iodoethane (one equivalent) in toluene (5 ml) was added dropwise to the mixture. The reaction mixture was refluxed for 2 hrs, cooled to room temperature and quenched by addition of water (10 ml). The two layers were separated and the water layer was extracted with toluene (15 ml). The combined toluene layers were combined and washed with water (10 ml) and dried over sodium sulphate. The mixture was filtered and evaporated yielding crude [$^{13}C_3$]-ethylmorphine (0.26 mg) which was purified by flash chromatography (on silica gel, 30% methanol in dichloromethane as eluted) and crystallized from ethanol; yield: 0.14 g (86.6%) white crystals with a purity of 98% (GC-MS).

Comparative Example 1

Synthesis of [$^{13}C_2$]-codeine

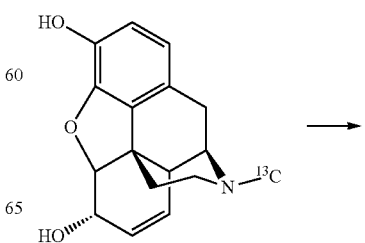

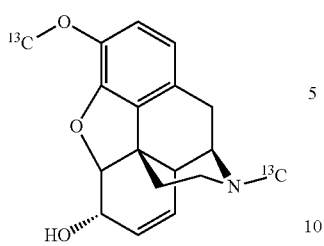

[$^{13}C_1$]-Morphine (N-methyl $^{13}C$, 0.15 g, 0.52 mmol), potassium carbonate (0.29 g, 2.01 mmol), and tetrabutylammonium bromide (0.17 g, 5.26 mmol) were added to toluene (10 ml). The mixture was heated to 110° C. A solution of [$^{13}C_1$]-iodomethane (one equivalent) in toluene (5 mL) was then added dropwise to the mixture. The reaction mixture was refluxed for 2 hours, cooled to room temperature and quenched by addition of water (10 mL). The two layers were separated, and the water layer was extracted with toluene (10 mL). The combined toluene layers were washed with water (15 ml) and dried over sodium sulfate. The mixture was filtered and evaporated yielding crude [$^{13}C_2$]-codeine (0.26 g) which was purified by flash chromatography (silica, 30% methanol in dichloromethane) and recrystallization from ethanol, yield 0.10 g (63.4%) of white crystals with a purity >99% (GC-MS).

Example 6

Synthesis of [$^{13}C_4$]-buprenorphine (Labeling in the Tertbutyl Side Chain)

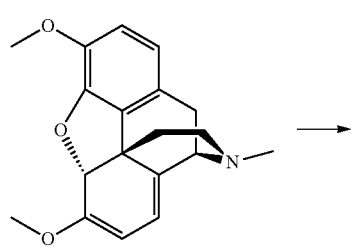

Thebaine

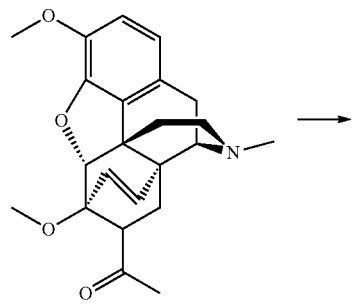

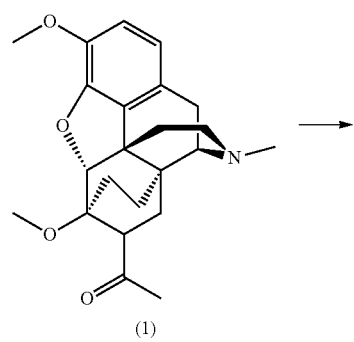

(1)

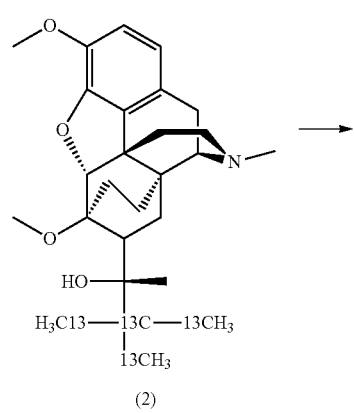

(2)

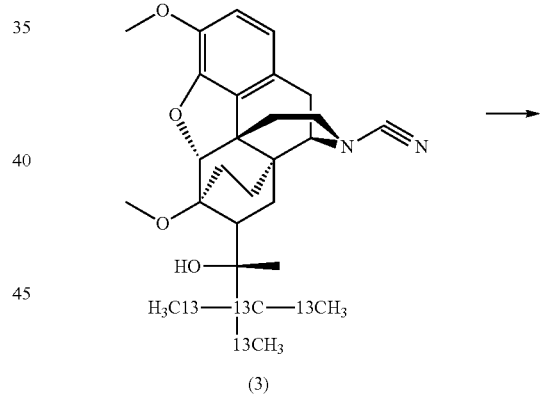

(3)

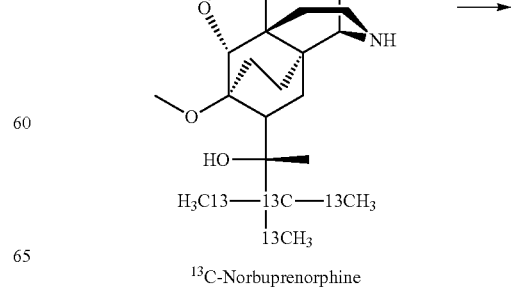

$^{13}C$-Norbuprenorphine

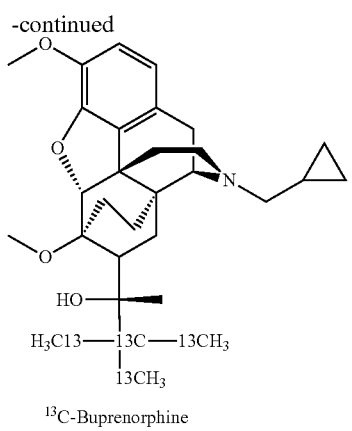

¹³C-Buprenorphine

6.1 Synthesis of 7-acetyl-6,14-endoethenotetrahydrothebaine (1-[(5α,7α)-4,5-Epoxy-3,6-dimethoxy-17-methyl-6,14-ethenomorphinan-7-yl]-ethanone Thebaine (10 g, 32.1 mmol) was boiled under reflux with methyl vinyl ketone (30 mL) for 1 hour. The excess of ketone was removed by diastillation under reduced pressure, and the viscous residue was dissolved in warm methanol (15 mL). The resulting solution was cooled in freezer with stirring. The crystalline solid was filtered, washed with cooled methanol and dried and was recrystallized with methanol to give 9.8 g (25.6 mmol), yield: 79.7%.

6.2 Synthesis of 7-acetyl-6,14-endoethanotetrahydrothebaine (1-[(5α,7α)-4,5-Epoxy-18,19-dihydro-3,6-dimethoxy-17-methyl-6,14-ethenomorphinan-7-yl]-ethanone 7-acetyl-6,14-endoethenotetrahydrothebaine (5 g, 13.0 mol) in ethanol (200 mL) was hydrogenated over 10% palladium on charcoal (0.5 g) at a hydrogen pressure of 4-5 bars and 50° C. for 10 hours. The catalyst was removed by filtration. Evaporation of the filtrate and crystallization of the residue from ethanol gave 3.5 g (9.1 mmol) product, Yield: 70%.

6.3 Synthesis of [¹³C₄]-6,14-endoethano-7-(2-hydroxy-3,3-dimethyl-2-butyl)-tetrahydrothebaine A solution of [¹³C₄]-tertbutyl magnesium chloride was prepared from magnesium (1.6 g) in ether (10 ml) and toluene (10 mL). The mixture was stirred overnight at room temperature. 7-Acetyl-6,14-endoethanotetrahydrothebaine (5.0 g, 13.0 mmol) in toluene (25 mL) was added dropwise. After standing overnight, the mixture was added to a saturated aqueous solution of ammonium chloride (250 ml). The organic phase was separated and the water phase was further extracted with toluene. The combined organic phases were dried with sodium sulfate. After the solvent was removed, the crude product, was recrystallized with methanol to give 1.42 g (3.2 mmol) product; yield: 24.6%.

6.4 Synthesis of [¹³C₄]-N-cyano-6,14-endoethano-7-(2-hydroxy-3,3-dimethyl-2-butyl)-terahydrothebaine

[¹³C₄]-6,14-Endoethano-7-(2-hydroxy-3,3-dimethyl-2-butyl)-tetrahydrothebaine (1.2 g, 2.70 mmol)) and cyanogen bromide (0.51 g, 4.8 mmol) were dissolved in chloroform (20 mL). The reaction mixture was stirred for 20 h at 65° C. The reaction mixture was cooled to ambient temperature and water (20 ml) was added to dissolve all the salt. The organic layer was separated and the water layer was extracted twice with chloroform (2×20 mL) and dried over MgSO₄. The solvent were evaporated under vacuum and the residue recrystallized from methanol (15 mL), yield 1.90 g, 1.4 mmol (87%) of product.

6.5 Synthesis of [¹³C₄]-norbuprenorphine

Potassium hydroxide (2.0 g, 51.3 mmol) was dissolved in diethyleneglycol (14 mL), and the solution was warmed to 180-190° C. [¹³C₄]-N-Cyano-6,14-endoethano-7-(2-hydroxy-3,3-dimethyl-2-butyl)-terahydrothebaine (1.80 g, 3.95 mmol) was added to the mixture, and the resulting reaction mixture was heated at 210-220° C. for 1 hour and then cooled and poured into ice-water (120 ml). The precipitate was collected and washed with water. The crude material was dissolved in dilute acetic acid and treated with charcoal. The base was precipitated with ammonia. The solid was recrystallized from a 1:1 solution of MeOH and acetonitrile (1:1, 20 mL/g), yielding 1.18 g (2.84 mmol, 72%) [¹³C₄]-norbuprenorphine.

6.6 Synthesis of [¹³C₄]-buprenorfine

[¹³C₄]-Norbuprenorphine (1.89 g, 4.53 mmol), KHCO₃ (1.0 g) and KI (1.08 g) were mixed in acetone (25 mL) and water (0.2 mL). The reaction mixture was heated to reflux and a solution of cyclopropylmethyl bromide (0.8 g, 5.92 mmol) in acetone (5 mL) was added slowly. After 8 hours, the reaction mixture was cooled down to room temperature and quenched by addition of water (40 mL). The reaction suspension was filtered, and the solid was washed with water, acetonitrile and dried; yield 1.92 g (4.08 mmol) [¹³C₄]-buprenorphine (90%).

Example 7

Synthesis of [¹³C₆]-(−)-cocaine

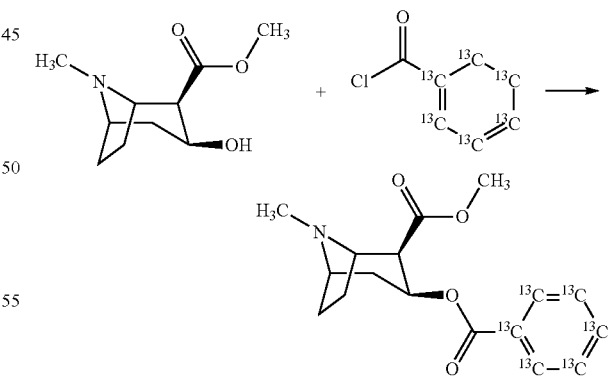

A stirred solution of (−)-methylecgonine hydrochloride (3.74 g, 15.9 mmol) in water (10 mL) was treated with chloroform (30 mL) and ammonium hydroxide (2 mL). The chloroform layer was separated, and the aqueous phase was extracted with additional chloroform (10 mL). The separated chloroform layer and the chloroform extract were combined and dried over sodium carbonate, filtered and treated with triethylamine (4.8 g) and [¹³C₆]-benzoyl chloride (4.46 g, 30.4 mmol). The resulting solution was stirred at ambient temperature for 24 hours and then cooled to 10° C. The cooled solution was mixed with hydrochloric acid (1.5 N, 45 mL) and stirred for 30 min. The upper layer was separated and the organic phase was extracted with water (10 mL). The removed upper aqueous layer was combined with the aqueous extract to form a combined aqueous solution. The combined aqueous solution was washed with chloroform (10 mL). Then, ammonium hydroxide was added until the pH of the combined aqueous solution was 9. After the pH adjustment, the combined aqueous solution was extracted twice with chloroform (2×20 mL). The combined chloroform extract was dried over carbonate, filtered and evaporated to yield a yellow oil. The oil was dissolved in tert-butyl methyl ether (30 mL), stirred with silica gel (0.3 g) and filtered. The filtrate was diluted with heptane (50 mL), concentrated to ca. 50 mL, cooled to 5-10° C. and slowly stirred for 3 hours. The formed crystals were filtered, washed with cold hexane and dried in vacuum to give [$^{13}C_6$]-(−)-cocaine as snow-white crystals. A second crop of crystals was isolated upon concentration of the mother liquor. The total yield was 3.93 g (80%).

Example 8

Synthesis of [$^{13}C_6$]-(−)-benzoylecgonine

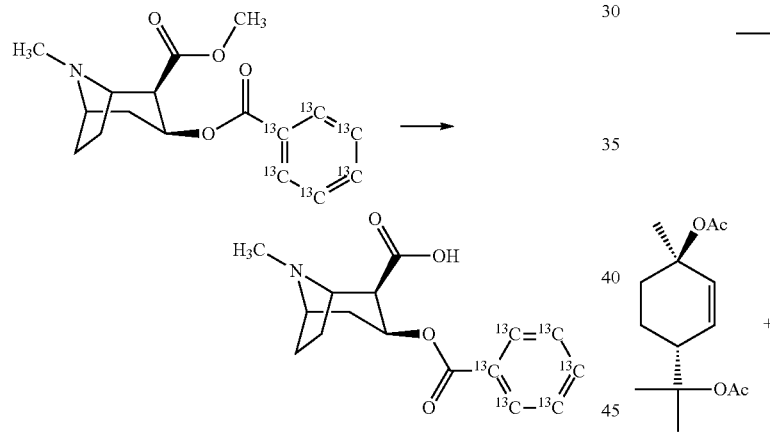

[$^{13}C_6$]-(−)-Cocaine freebase (2.0 g, 6.47 mmol) was dissolved in water (3 mL), and dioxane (3 mL). The resulting mixture was stirred at 60° C. for seven days. The water/dioxin mixture was removed under reduced pressure yielding 1.9 g [$^{13}C_4$]-(−)-benzoylecgonine (99%) as a white solid.

Example 9 a) Synthesis of [$^{13}C_6$]-Δ9-THC

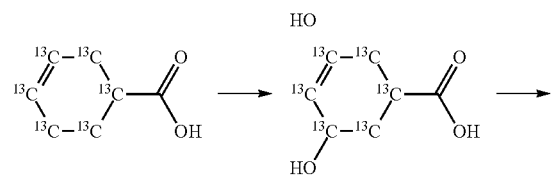

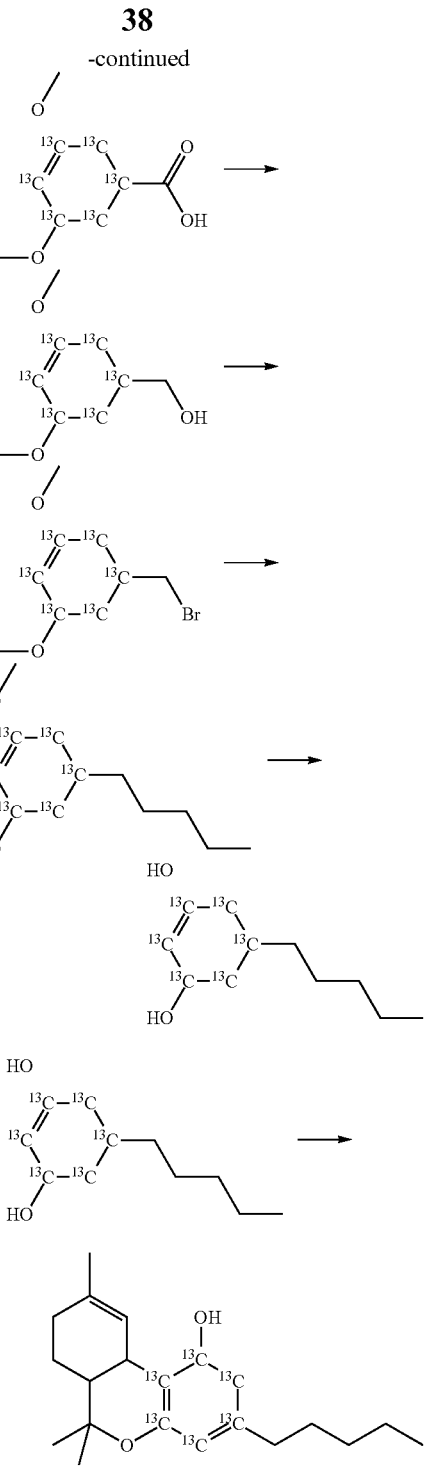

9.1a Synthesis of [$^{13}C_6$]-3,5-dihydroxybenzoic acid

20% fuming $H_2SO_4$ (15 mL) was added to [$^{13}C_6$]-benzoic acid (5.0 g, 39 mmol) in a 50 ml glass pressure reactor. The reaction mixture was heated to 250° C. for 5 hours and then cooled down to room temperature before the whole batch was added to 100 g crushed ice and stirred until everything had melted. Barium hydroxide was added to the water solution until the pH was 7-8. The pasty mass is filtered by suction on a Buchner funnel, and the barium sulfate is washed with portions of water (5×15 mL). The combined filtrates were evaporated to dryness on a rotary evaporator, and the final salt was dried in an oven at 130° C. for 2 hours. The yield of the crude barium salt was 12.7 g.

The dried pulverized barium salt was added in one portion to a melt of 15 g NaOH and 15 g KOH and further warmed to 250° C. The reaction was visible by a slight evolution of gas. The reaction mixture was continuously stirred at 280° C. for 1 hour. The melt was then added carefully to water (150 mL), and the precipitated barium salt was filtered of by suction. The filtrate was acidified with concentrated hydrochloric acid (50 mL). The resulting solution was cooled down and extracted with ether (3×50 mL). The organic phase was dried by addition of $MgSO_4$ and the solvent was evaporated to yield 3.29 g product. This crude product was crystallized with acetic acid (15 ml) as needle like crystals and filtered to yield 2.9 g (49%).

9.2a Synthesis of $[^{13}C_6]$-3,5-dimethoxybenzoic acid $[^{13}C_6]$-3,5-Dihydroxybenzoic acid (1.81 g, 11.7 mmol) was dissolved in water (20 mL). NaOH (1.41 g, 35 mmol) was dissolved in water (10 mL) and slowly added under argon atmosphere. Dimethyl sulfate (2.3 mL, 24.6 mmol) was added slowly to the solution at a temperature of 10° C. The reaction mixture was then gradually heated to 100° C. and stirred at that temperature for 2 hours. Concentrated ammonium solution (1 mL) was added. The temperature was adjusted to room temperature, and then the pH was adjusted to 2 with concentrated hydrochloric acid. The water phase was filtered on a Buchner funnel. The filter cake was dried in an exicator overnight to yield 1.26 g $[^{13}C_6]$-3,5-dimethoxybenzoic acid (58%).

9.3a Synthesis of $[^{13}C_6]$-3,5-dimethoxyphenyl methanol $[^{13}C_6]$-3,5-Dimethoxybenzoic acid (1.26 g, 6.6 mmol) was dissolved in THF (10 ml). This solution was then added slowly to a suspension of $LiAlH_4$ (0.37 g, 9.8 mmol) in THF (30 mL) at room temperature. The reaction mixture was then stirred at room temperature for 30 min before reflux for 4 hours. The reaction mixture was cooled down to 0° C., and NaOH solution (5%, 0.5 mL) and then water (1 mL) were added. The granular suspension was filtered through a plug of celite on a Buchner funnel, and the solids were washed with some extra solvent (2×30 mL). The organic phase was washed with brine (50 mL) and dried over $MgSO_4$. The solvent was evaporated to yield 0.72 g $[^{13}C_6]$-3,5-dimethoxyphenyl methanol (62%).

9.4a Synthesis of $[^{13}C_6]$-3,5-dimethoxybenzyl bromide $[^{13}C_6]$-3,5-dimethoxyphenyl methanol (0.72 g, 4.1 mmol) was dissolved in $CH_2Cl_2$ (20 mL) and the solution was cooled to −10° C. on an ice/salt bath. A solution of phosphorous tribromide (1.1 g, 4.1 mmol) in $CH_2Cl_2$ (2 mL) was added to the solution. The reaction mixture was stirred at room temperature overnight. Water was added to the reaction mixture (50 mL), and the product was extracted with $CH_2Cl_2$ (2×40 mL). The organic phase was washed with saturated $NaHCO_3$ solution, dried over $MgSO_4$ and evaporated to yield 0.74 g $[^{13}C_6]$-3,5-dimethoxybenzyl bromide (76%).

b) Synthesis of $[^{13}C_4]$-Δ9-THC 9.1b Synthesis of $[^{13}C_4]$-3,5-dimethoxyphenyl-1-pentane

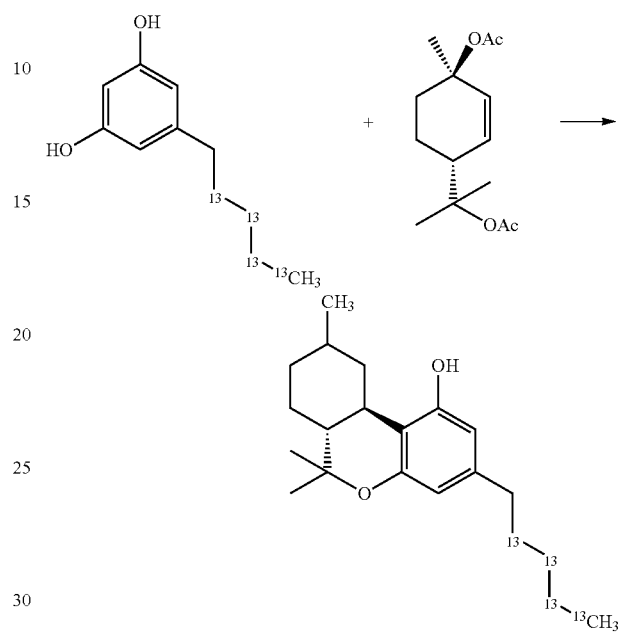

A cooled solution of $[^{13}C_4]$-butyl magnesium bromide (3.5 mmol) generated from $[^{13}C_4]$-butyl bromide and magnesium in ether (3.5 mL, 1 M) was added dropwise to a mixture of 3,5-dimethoxybenzyl bromide (0.71 g, 3.0 mmol) in diethyl ether (20 mL) and $Li_2CuCl_4$ (0.1 mL, 0.1 M in THF). The reaction was allowed to warm to room temperature and then stirred for 30 h. The reaction mixture was quenched by addition of saturated ammonium chloride solution (5 mL) followed by water (25 mL). The organic layer was separated and the aqueous layer was extracted with ether (20 mL). The resulting emulsion was passed through glass wool and the organic layers were combined and dried over $MgSO_4$. The product was purified on silica gel using 10% ethylacetate in heptane as eluent, yielding 0.51 g (80%) pure $[^{13}C_4]$-3,5-dimethoxyphenyl-1-pentane 9.2b Synthesis of $[^{13}C_4]$-olivetol The labelled dimethyl ether (0.51 g, 2.37 mmol) was dissolved in chloroform (30 mL) and treated with trimethylsilyl iodide (1.4 g, 7.2 mmol). The mixture was heated to 40° C. until no more starting material was detected by TLC (48 h). The reaction mixture was cooled, poured on methanol (20 mL) and evaporated in vacuum. Ether (20 mL) was added and the solution was washed with aqueous sodium bisulfate, $NaHCO_3$ and NaCl, and dried over $MgSO_4$. The product was purified on silica gel using toluene as eluent yielding 0.34 g (75%) of $[^{13}C_4]$-olivetol.

9.3b Synthesis of $[^{13}C_4]$-Δ9-THC

A 25 mL round bottom flask was dried in the oven, fitted with a septum and cooled. The atmosphere was thoroughly flushed with Ar. (+)-p-Menth-2-ene-1,8-diacetate (0.46 g, 1.82 mmol) and [$^{13}C_4$]-olivetol (0.34 g, 1.80 mmol) were added. Anhydrous $CH_2Cl_2$ (15 mL) was added and stirred under Ar atmosphere. The solution was cooled to −5° C. and $BF_3(OEt)_2$ (243 μl, 1 eq) was added. The solution gradually darkened to red. After 15-20 min, the reaction was quenched with 10% $Na_2CO_3$. The layers were separated and the organic layer was washed with 10% $Na_2CO_3$ (20 mL). The combined aqueous phases were extracted once with $CH_2Cl_2$ (20 mL). The organic solutions were combined and washed with water and saturated NaCl solution and then dried over $MgSO_4$. The yield was 1.32 g of a brown oil which was purified further on preparative HPLC to yield 0.36 g (63%) [$^{13}C_4$]-Δ9-THC.

Example 10 a) Synthesis of [$^{13}C_6$]-(−)-Δ9-THC acid

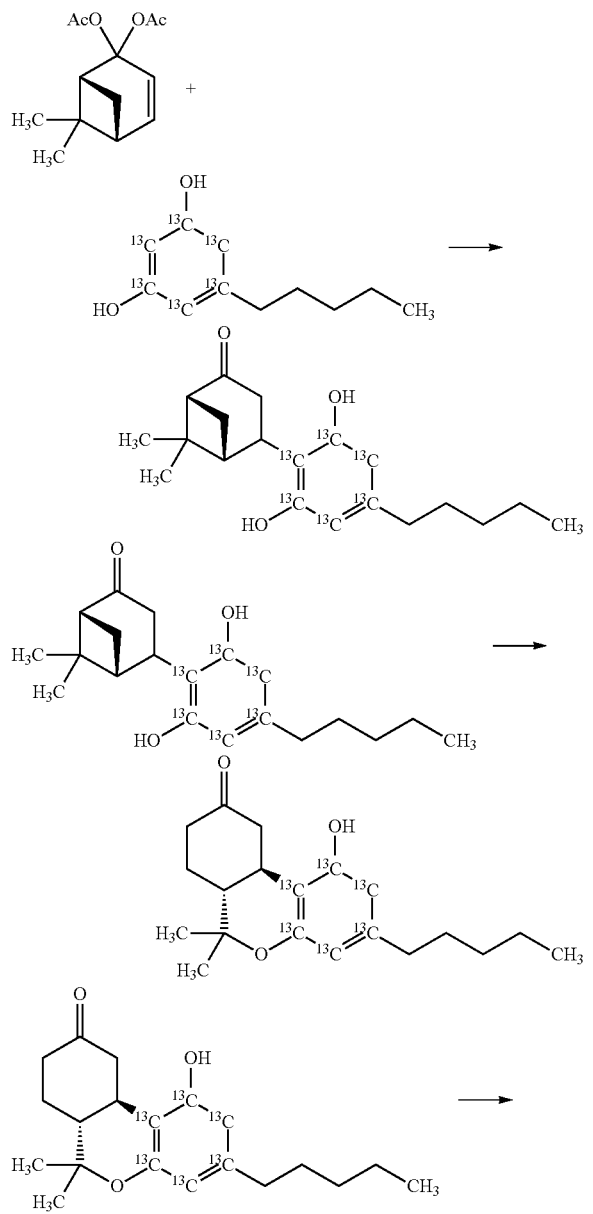

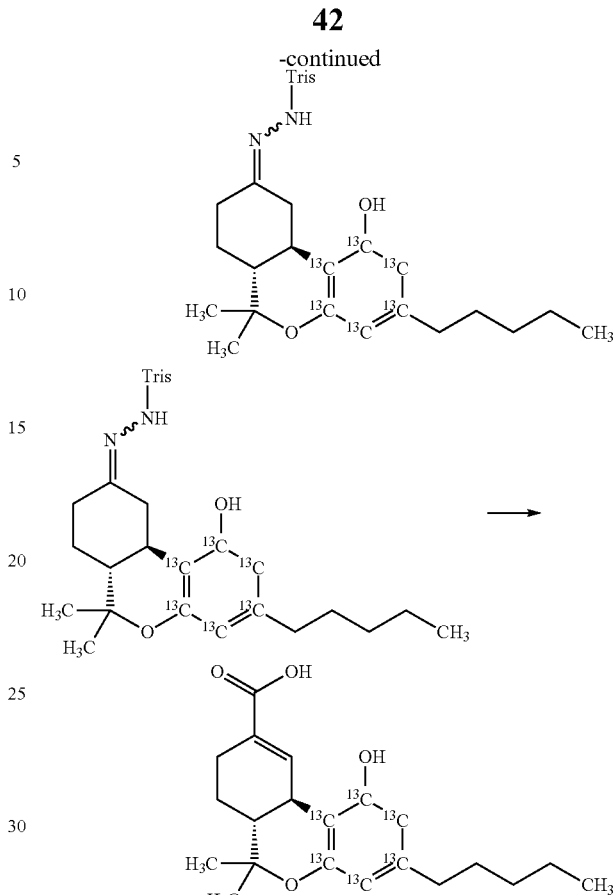

10.1a Synthesis of [$^{13}C_6$]-(4R)-4-(4-Pentyl-2,6-dihydroxy-$^{13}C_6$-phenyl)-6,6-di-methyl-2-norpinanone p-Toluenesulfonic acid monohydrate (3.90 g, 20.50 mmol) was added to a degassed solution of $^{13}C_6$-Olivetol (2.79 g, 15 mmol) and (+)-6,6-dimethyl-2,2-diacetoxy-3-norpinene, (5.61 g, 20.5 mmol) in $CHCl_3$ (150 mL) at 0° C. under an argon atmosphere. The reaction mixture was warmed to room temperature and stirred for 3 days to ensure complete formation of the product. The mixture was diluted with diethyl ether and washed sequentially with water, saturated aqueous NaHCO3, and brine. The organic phase was dried over MgSO4 and the solvent was removed under reduced pressure. The residue obtained was dry flashed on silica gel in a Buchner funnel with 45% diethyl ether in heptane). The fractions containing almost pure product (TLC) were combined and evaporated. Further purification by flash column chromatography on silica gel (30% acetone in heptane) gave (4R)-4-(4-pentyl-2,6-dihydroxy-$^{13}C_6$-phenyl)-6,6-di-methyl-2-norpinanone as a white crystalline solid (1.69 g, 35% yield).

10.2a Synthesis of [$^{13}C_6$]-(6aR,10aR)-6,6a,7,8,10,10a-Hexahydro-1-hydroxy-6,6-dimethyl-3-pentyl-9H-dibenzo[b,d]pyran-9-one Trimethylsilyl trifluoromethanesulfonate (3.81 mL, 0.3 M solution in $CH_3NO_2$, 1.14 mmol) was added to a solution of (4R)-4-(4-Pentyl-2,6-dihydroxy-$^{13}C_6$-phenyl)-6,6-di-methyl-2-norpinanone (1.69 g, 5.25 mmol) in anhydrous $CH_2Cl_2/CH_3NO_2$ (3:1, 90 mL) at 0° C. under an argon atmosphere. The reaction mixture was stirred for 6 h. The reaction was quenched with saturated aqueous NaHCO$_3$/brine (1:1). Diethyl ether was added. The organic phase was separated, and the aqueous phase was extracted with diethyl ether. The organic phase was washed with brine, and dried over MgSO4. Solvent evaporation and purification by flash column chromatography on silica gel (50% diethyl ether in hexane) afforded 1.17 g (69% yield) of [$^{13}C_6$]-(6aR,10aR)-6,6a,7,8,10,10a-hexahydro-1-hydroxy-6,6-dimethyl-3-pentyl-9H-dibenzo[b,d]pyran-9-one as a white foam.

10.3a Synthesis of [$^{13}C_6$]-(−)-Δ9-THC acid

6aR,10aR)-6,6a,7,8,10,10a-Hexahydro-1-hydroxy-6,6-dimethyl-3-pentyl-9H-dibenzo[b,d]pyran-9-one (1.17 g, 3.62 mmol) and 2,4,6-triisopropylbenzenesulfonylhydrazide (1.08 g, 3.62 mmol) were mixed in anhydrous toluene (120 mL) and the solvent was evaporated under reduced pressure after 1 hour reaction time at 22° C. to give benzenesulfonic acid, 2,4,6-tris(1-methylethyl)-2-[(6aR,10aR)-6,6a,7,8,10,10a-hexahydro-1-hydroxy-6,6-dimethyl-3-pentyl-9H-dibenzo[b,d]pyran-9-ylidene]hydrazide as a foam. This material (1.21 g, 3.62 mmol) was dissolved in dry hexane/TMEDA (80 mL, 1:1 ratio) under an argon atmosphere at 78° C. n-BuLi (3.32 mL, 8.31 mmol, using a 2.5 M solution in hexane) was added to this solution. The reaction mixture was stirred for 20 min at 78° C. and then it was warmed to 5° C. over a 10 min period and stirred at that temperature for an additional 20 min. The reaction mixture was cooled to 78° C. and a second portion of n-BuLi (3.32 mL, 8.31 mmol) was added. Following the addition, the mixture was stirred for 10 min at 78° C. and then allowed to warm to 0° C. over a 10 min period. Stirring was continued for 20 min at 0° C., and then dry CO$_2$ was bubbled into the reaction mixture for 30 min. The pH was adjusted to 2 by the addition of 5% aqueous HCl solution at 0° C., and the mixture was warmed to room temperature and extracted with diethyl ether. The ethereal solution was washed with brine, dried (MgSO4), and the solvent was evaporated under reduced pressure. The residue obtained was purified by flash column chromatography (20% ethyl acetate in heptane) on silica gel and washed with pentane (10 mL) to give [$^{13}C_6$]-(−)-Δ9-THC acid as a white solid material 101 mg, 8% yield.

b) Synthesis of [$^{13}C_4$]-(−)-Δ9-THC Acid

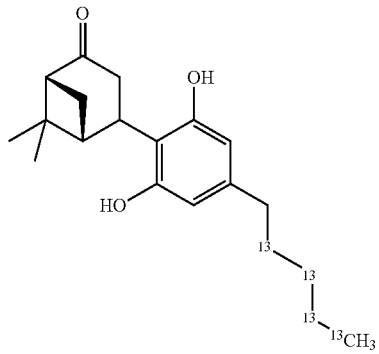

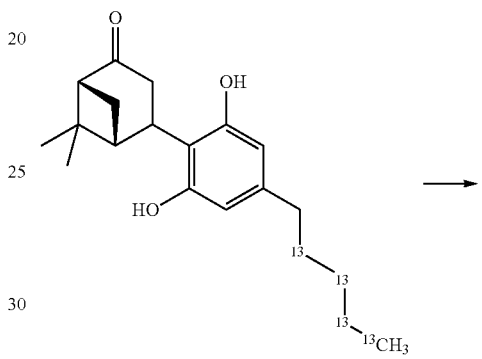

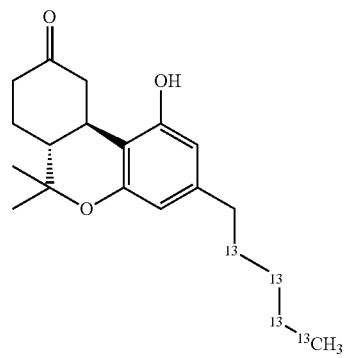

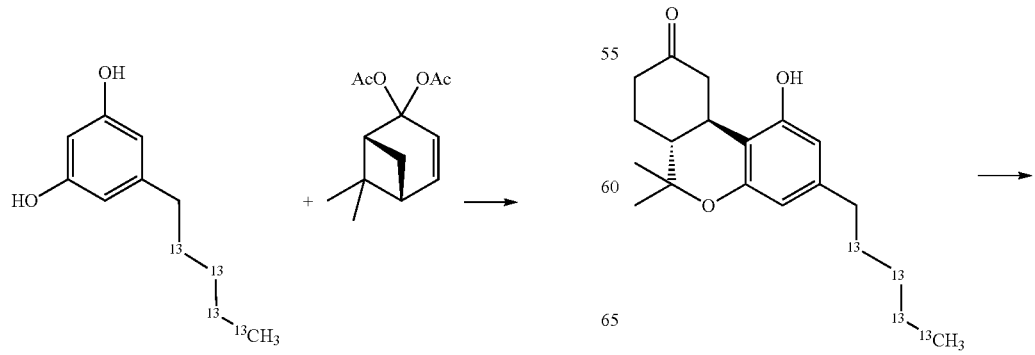

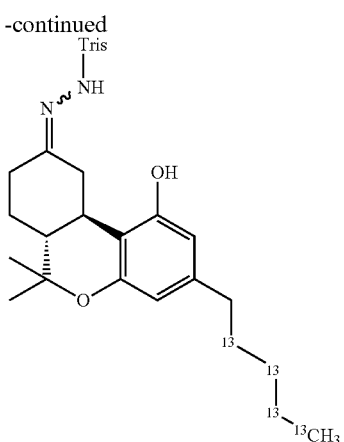

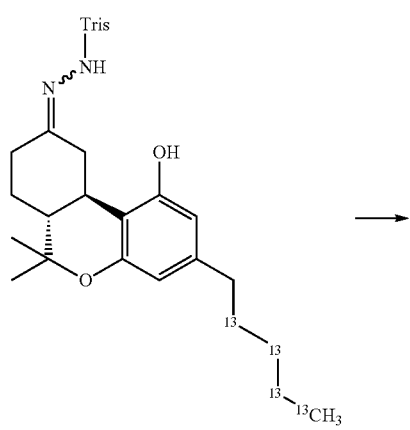

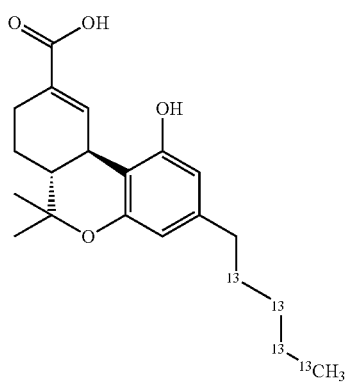

10.1b Synthesis of [$^{13}C_4$]-(4R) (4-Pentyl-2,6-dihydroxy-$^{13}C_6$-phenyl)-6,6-di-methyl-2-norpinanone p-Toluenesulfonic acid monohydrate (3.90 g, 20.50 mmol) was added to a degassed solution of [$^{13}C_4$]-Olivetol (2.79 g, 14.83 mmol) and (+)-6,6-dimethyl-2,2-diacetoxy-3-norpinene, (5.61 g, 20.5 mmol) in CHCl$_3$ (150 mL) at 0° C. under an argon atmosphere. The reaction mixture was warmed to room temperature and stirred for 3 days to ensure complete formation of the product. The mixture was diluted with diethyl ether and washed sequentially with water, saturated aqueous NaHCO3, and brine. The organic phase was dried over MgSO4 and the solvent was removed under reduced pressure. The residue obtained was dry flashed on silica gel in a Buchner funnel with 45% diethyl ether in heptane). The fractions containing almost pure product (TLC) were combined and evaporated. Further purification by flash column chromatography on silica gel (30% acetone in heptane) gave (4R)-4-(4-$^{13}C_4$-pentyl-2,6-dihydroxy-phenyl)-6,6-dimethyl-2-norpinanone as a white crystalline solid (3.5 g, 88% yield).

10.2b Synthesis of [$^{13}C_4$]-(6aR,10aR)-6,6a,7,8,10,10a-Hexahydro-1-hydroxy-6,6-dimethyl-3-pentyl-9H-dibenzo[b,d]pyran-9-one Trimethylsilyl trifluoromethanesulfonate (3.81 mL, 0.3 M solution in CH$_3$NO$_2$, 1.14 mmol) was added to a solution of (4R)-4-(4-$^{13}C_4$-Pentyl-2,6-dihydroxy-phenyl)-6,6-di-methyl-2-norpinanone (1.69 g, 5.27 mmol) in anhydrous CH$_2$Cl$_2$/CH$_3$NO$_2$ (3:1, 90 mL) at 0° C. under an argon atmosphere. The reaction mixture was stirred for 6 h. The reaction was quenched with saturated aqueous NaHCO$_3$/brine (1:1). Diethyl ether was added. The organic phase was separated, and the aqueous phase was extracted with diethyl ether. The organic phase was washed with brine, and dried over MgSO4. Solvent evaporation and purification by flash column chromatography on silica gel (50% diethyl ether in hexane) afforded 1.39 g (82% yield) of [$^{13}C_4$]-(6aR,10aR)-6,6a,7,8,10,10a-hexahydro-1-hydroxy-6,6-dimethyl-3-pentyl-9H-dibenzo[b,d]pyran-9-one as a white foam.

10.3b Synthesis of [$^{13}C_4$]-(−)-Δ9-THC Acid

[$^{13}C_4$]-(6aR,10aR)-6,6a,7,8,10,10a-Hexahydro-1-hydroxy-6,6-dimethyl-3-pentyl-9H-dibenzo[b,d]pyran-9-one (212.3 mg, 0.67 mmol) and 2,4,6-triisopropylbenzenesulfonylhydrazide (200.46 mg, 0.67 mmol) were mixed in anhydrous toluene (10 mL) and the solvent was evaporated under reduced pressure after 1 hour reaction time at 22° C. to give benzenesulfonic acid, 2,4,6-tris(1-methylethyl)-2-[(6aR,10aR)-6,6a,7,8,10,10a-hexahydro-1-hydroxy-6,6-dimethyl-3-pentyl-9H-dibenzo[b,d]pyran-9-ylidene]hydrazide as a foam. This material was dissolved in dry hexane/TMEDA (4 mL, 1:1 ratio) under an argon atmosphere at −78° C. n-BuLi (610 µL, 1.53 mmol, using a 2.5 M solution in hexane) was added to this solution. The reaction mixture was stirred for 20 min at −78° C. and then it was warmed to 5° C. over a 10 min period and stirred at that temperature for an additional 20 min. The reaction mixture was cooled to −78° C. and a second portion of n-BuLi (610 µL, 1.53 mmol) was added. Following the addition, the mixture was stirred for 10 min at −78° C. and then allowed to warm to 0° C. over a 10 min period. Stirring was continued for 20 min at 0° C., and then dry CO$_2$ was bubbled into the reaction mixture for 30 min. The pH was adjusted to 2 by the addition of 5% aqueous HCl solution at 0° C., and the mixture was warmed to room temperature and extracted with diethyl ether. The ethereal solution was washed with brine, dried (MgSO4), and the solvent was evaporated under reduced pressure. The residue obtained was purified by flash column chromatography (20% ethyl acetate in heptane) on silica gel and washed with pentane (10 mL) to give [$^{13}C_4$]-(−)-Δ9-THC acid as a white solid material 41 mg, 18% yield.

Example 11

Synthesis of [$^{13}C_6$]-nitrazepam

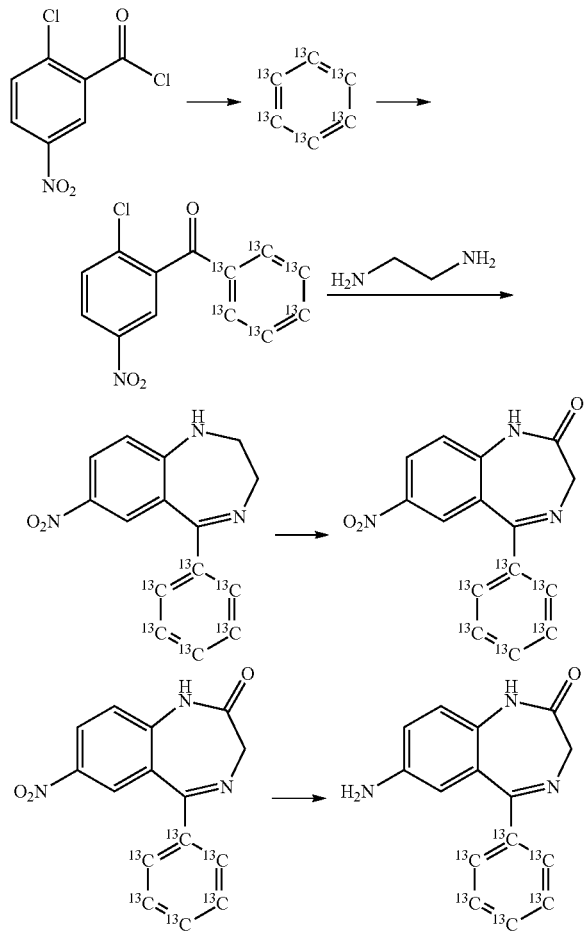

11.1 Synthesis of [$^{13}C_6$]-2-chloro-5-nitrobenzophenone

[$^{13}C_6$]-Benzene (0.6 g, 7.1 mmol) was added to a solution of 2-chloro-5-nitrobenzoic acid chloride (3.13 g, 14.3 mmol) in 50 mL of dichloromethane. The mixture was cooled to 0-5° C. before AlCl$_3$ (2.29 g, 17.2 mmol) was added in slowly. Upon completion of the addition, the mixture was allowed to reach room temperature, and stirring was continued for 24 h. The deep-red solution was treated with HCl and ice, and the resulting aqueous phase was extracted with ether. The combined organic extracts were washed with 2% aqueous NaOH and then water and dried over sodium sulphate. The solvent was removed in vacuo to give crude benzophenone, which was recrystallized from toluene/isopropyl ether to yield 1.52 g (80%) of pure [$^{13}C_6$]-2-chloro-5-nitrobenzophenone.

11.2 Synthesis of [$^{13}C_6$]-2,3-dihydro-7-nitro-5-phenyl-1H-1,4-benzodiazepine Ethylenediamine (4.61 g, 5.2 mL, 76.9 mmol) was charged into a flask equipped with stirrer and heated to 70° C., after which the heater was switched off and [$^{13}C_6$]-2-chloro-5-nitrobenzophenone (1.5 g, 5.62 mmol) was added gradually so that the temperature didn't exceed 70-75° C. When all [$^{13}C_6$]-2-chloro-5-nitrobenzophenone was introduced, the mixture was kept at 78-80° C. for 3 h and was then diluted with 5 ml of water at the same temperature, kept at the temperature for 1 h, and cooled to 10-15° C. The precipitated product was separated by filtration, washed with water and dried. The yield of [$^{13}C_6$]-2,3-dihydro-7-nitro-5-phenyl-1H-1,4-benzodiazepine was 1.45 g, 5.34 mmol (95%).

11.3 Synthesis of [$^{13}C_5$]-1,3-dihydro-7-nitro-5-phenyl-1H-1,4-benzodiazepin-2-one ([$^{13}C_6$]-nitrazepam)

Concentrated sulfuric acid (1.7 mL, 31.8 mmol) was added to acetone (20 mL) with stirring and cooling. [$^{13}C_6$]-2,3-Dihydro-7-nitro-5-phenyl-1H-1,4-benzodiazepine (1.0 g, 31.8 mmol) was added slowly to the mixture, followed by a saturated sodium bichromate solution prepared from Na$_2$Cr$_2$O$_7$ (1 g, 3.8 mmol) and water (0.6 mL). The temperature of the mixture was kept all the time below 20° C. When all components were introduced, the mixture was stirred for 1 h at a temperature below 20°. The precipitate was separated by filtration and mixed with water (20 mL). The mixture was neutralized by adding an aqueous alkali solution. The precipitate was separated, washed with water and dried. The yield of [$^{13}C_6$]-nitrazepam was 0.98 g (93%).

Example 12

Synthesis of [$^{13}C_6$]-7-aminonitrazepam

[$^{13}C_6$]-Nitrazepam (1.0 g, 3.48 mmol) was dissolved in acetic acid (20 mL). The solution was added slowly to a suspension of iron (8.0 g) in acetic acid (60 mL) at 75° C. The reaction mixture was stirred for 60 min and water was added (150 mL). Excess iron was separated by a magnet and the solution was decanted off. The iron and the water solution was extracted with chloroform (2×50 mL) before the combined organic phases were washed with saturated NaHCO$_3$ solution (50 mL). The organic phase was dried over MgSO$_4$ and the solvent was evaporated on a rotary evaporator. The crude product was purified by flash chromatography over silica with 7% methanol in chloroform containing 1% added ammonia (28% in water). The yield of [$^{13}C_6$]-aminonitrazepam was 393 mg (44%).

Example 13

Synthesis of [$^{13}C_6$]-clonazepam

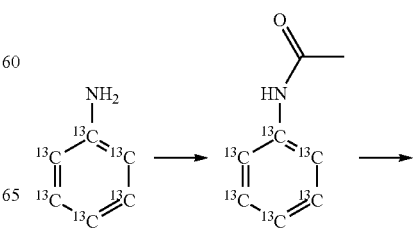

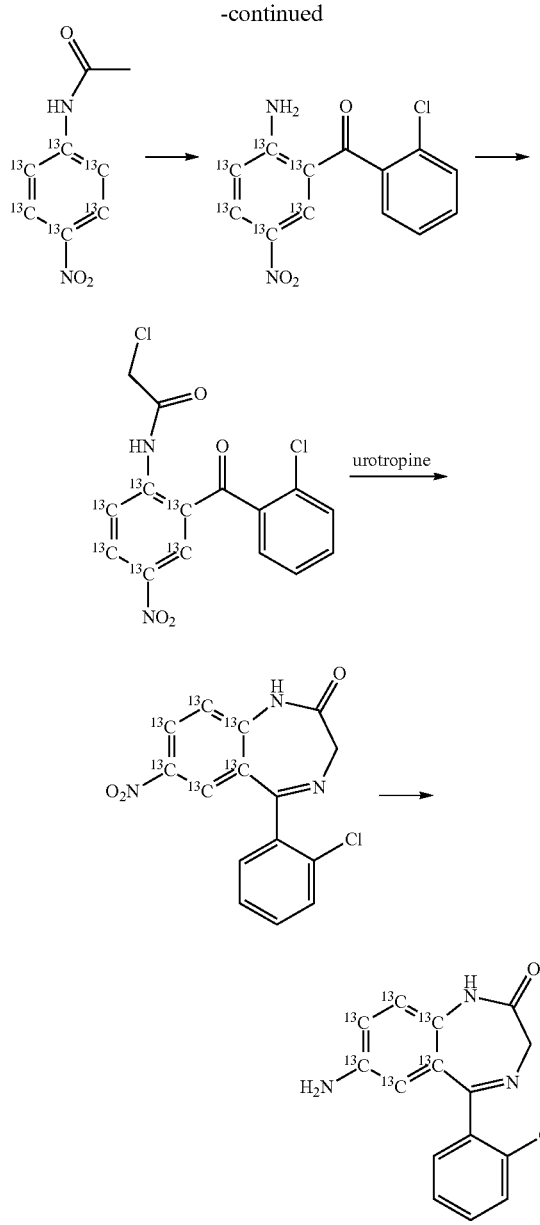

13.1 Synthesis of 4-nitro-[$^{13}C_6$]-acetanilide

[$^{13}C_6$]-Aniline (4.95 g, 50.0 mmol) was introduced from a dropping funnel to acetic anhydride (30 mL). After the aniline was added, the warm mixture was cooled to 10-15° C. with ice-water bath. 70% nitric acid (6.5 mL, 0.1 mmol) was dropped in at a rate which maintained the temperature within 10-12° C. After the addition was complete, the solution was poured into 150 mL of ice water, 4-nitro [$^{13}C_6$]-acetanilide precipitated as a white solid which was collected and washed with ice-water and dried. Yield: 7.91 g (42.5 mmol, 85.0%).

13.2 Synthesis of [$^{13}C_6$]-2-amino-5-nitro-2'-chlorobenzophenone

4-Nitro-[$^{13}C_6$]-acetanilide (1.86 g, 10.0 mmol) was added to a solution of 2-chlorobenzoyl chloride (1.5 mL, 11.5 mmol) and zinc chloride (2.0 g, 14.6 mmol) at 130° C., and the mixture was heated to 200° C. The solution was allowed to return to 160° C., whereafter 4.5 mL of acetic acid were added. When the temperature went down to 120° C., water (3 mL) was introduced to the mixture, followed by concentrated sulphuric acid (5.5 mL). The mixture was then warmed at 130° C. for 2 hours, and then was cooled to 70° C. by adding toluene (25 mL) and water (25 mL). The mixture was stirred until everything was dissolved. The organic phase was separated, washed with NaOH aqueous solution and water until it was neutral and dried over sodium sulphate. After the sodium sulphate and the solvent were removed, the residue was treated with petroleum ether, and the precipitated brown crystalline was filtered and dried. The yield was 1.81 g (6.4 mmol), 64%.

13.3 Synthesis of [$^{13}C_6$]-2-(2-chloroacetamido)-5-nitro-2'-chlorobenzophenone A solution of [$^{13}C_6$]-2-amino-5-nitro-2'-chlorobenzophenone (0.50 g, 1.78 mmol) in cyclohexane (10 ml) was warmed to reflux, and chloroacetyl chloride (0.5 mL) was added dropwise. The mixture was refluxed for 3.5 hours, cooled to room temperature, washed with water until neutral, and dried over sodium sulfate. Crude [$^{13}C_6$]-2-(2-chloroacetamido)-5-nitro-2'-chlorobenzophenone 0.61 g (1.71 mmol) (98% yield) was obtained after removal of the sodium sulfate and of the solvent.

13.4 Synthesis of [$^{13}C_6$]-clonazepam

[$^{13}C_6$]-2-(2-Chloroacetamido)-5-nitro-2'-chlorobenzophenone (0.50 g, 1.40 mmol) and urotropine (1.0 g, 7.1 mmol) were mixed with ethanol (15 mL) and hydrochloride acid (0.5 mL). The mixture was refluxed for 18 hours. 40-60% of the ethanol was removed from the reaction mixture before it was cooled down to room temperature. The solid precipitate was filtered off, washed with water and dried. The crude product was recrystallized from ethanol to give 0.16 g (38.7% yield) of [$^{13}C_6$]-clonazepam.

Example 14

Synthesis of [$^{13}C_6$]-7-aminoclonazepam

[$^{13}C_6$]-Clonazepam (0.10 g, 0.31 mmol) was dissolved in acetic acid (5 mL). The solution was added slowly to a suspension of iron (1.0 g) in acetic acid (20 mL) at 75° C. The reaction mixture was stirred for 60 min, and water was added (80 mL). Excess iron was separated by a magnet and the solution was decanted off. The iron and the water solution were extracted with chloroform (2×30 mL) before the combined organic phases were washed with saturated NaHCO$_3$ solution (30 mL). The organic phase was dried over MgSO$_4$ and the solvent was evaporated on a rotary evaporator. The crude product was purified by flash chromatography over silica with 5% methanol in chloroform added 1% ammonia (28% in water). The yield of [$^{13}C_6$]-7-aminoclonazepam was 54 mg (60%).

Example 15

Synthesis of [$^{13}C_6$]-flunitrazepam

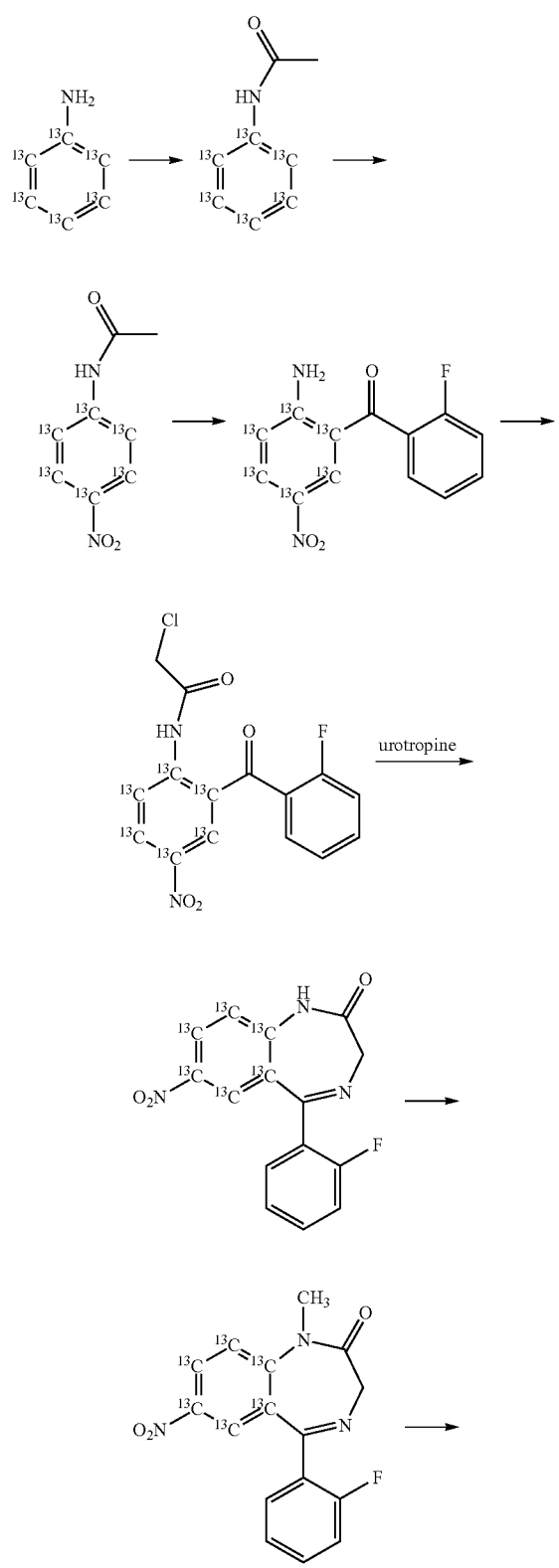

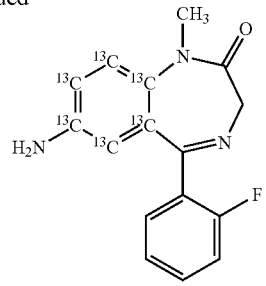

15.1 Synthesis of [$^{13}C_6$]-5-(2-fluorophenyl)-1,3-dihydro-7-nitro-2H-1,4-benzodiazepin-2-one ([$^{13}C_6$]-demethylflunitrazepam)

4-Nitro-[$^{13}C_6$]-acetanilidine (1.86 g, 10.0 mmol) was reacted with 2-fluorobenzoyl chloride as described in Example 13.2, [$^{13}C_6$]-2-amino-5-nitro-2'-chlorobenzophenone was obtained as a brown crystalline solid; yield: 1.78 g (6.7 mmol), 67%. [$^{13}C_6$]-2-Amino-5-nitro-2'-chlorobenzophenone (1.75 g, 6.57 mmol) was reacted with chloroacetyl chloride (2.0 mL) as described in Example 13.3. [$^{13}C_6$]-2-(2-chloroacetamido)-5-nitro-2'-fluorobenzophenone 2.14 g (6.24 mmol) (95% yield) was obtained.

[$^{13}C_6$]-2-(2-chloroacetamido)-5-nitro-2'-fluorobenzophenone 2.0 g (5.83 mmol) was reacted with urotropine as described in Example 13.4 to yield solid [$^3C_6$]-demethylflunitrazepam 0.72 g, 2.33 mmol (40%).

15.2 Synthesis of [$^{13}C_6$]-flunitrazepam

To a solution of [$^{13}C_6$]-demethylflunitrazepam (0.7 g, 2.31 mmol) in methanol (16 mL) was introduced a solution of sodium methoxide prepared from methanol (3 mL) and sodium (85 mg). The methanol was then removed under reduced pressure, DMF (10 mL) was added and the mixture was stirred at 30° C. for 1 hour before it was poured into ice-water (35 mL). The solid precipitate was filtered off, washed with ethanol, recrystallized from acetonitrile and ethanol to yield 0.52 g (1.64 mmol) [$^{13}C_6$]-flunitrazepam (71.1%).

Example 16

Synthesis of [$^{13}C_6$]-7-aminoflunitrazepam

[$^{13}C_6$]-Flunitrazepam (0.45 g, 1.47 mmol) was dissolved in acetic acid (10 mL). The solution was added slowly to a suspension of iron (4.0 g) in acetic acid (30 mL) at 75° C. The reaction mixture was stirred for 60 min, and water was added (100 mL). Excess iron was separated by a magnet and the solution was decanted off. The iron and the water solution were extracted with chloroform (2×40 ml) before the combined organic phases were washed with saturated $NaHCO_3$ solution (50 mL). The organic phase was dried over $MgSO_4$ and the solvent was evaporated on a rotary evaporator. The crude product was purified by flash chromatography over silica with 7% methanol in chloroform containing 1% added ammonia (28% in water). The yield of [$^{13}C_6$]-7-aminoflunitrazepam was 178 mg (44%).

Example 17

Synthesis of [$^{13}C_6$]-desmethyldiazepam

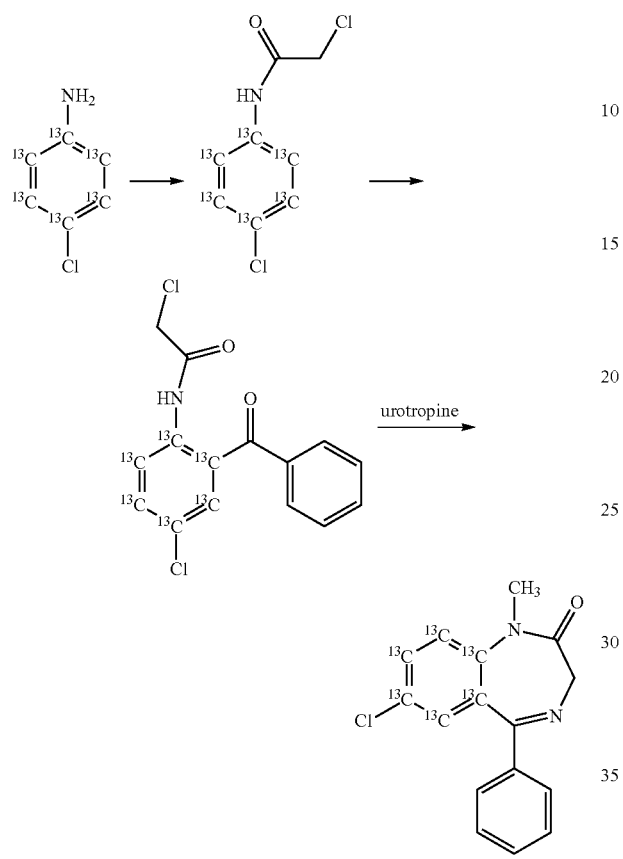

17.1 Synthesis of [$^{13}C_6$]-2-chloro-N-(4-chlorophenyl)acetamide

[$^{13}C_6$]-4-Chloroaniline (2.67 g, 19.5 mmol) was suspended in toluene (100 mL), and chloroacetylchloride (8.80 g, 78 mmol) was added dropwise with stirring. The mixture was heated to reflux for 12 hours, cooled to room temperature and poured into ice-water. The solid product obtained was filtered and dried; yield 3.89 g (95%).

17.2 Synthesis of [$^{13}C_6$]-2-(2-chloroacetamido)-5-chlorobenzophenone

[$^{13}C_6$]-2-Chloro-N-(4-chlorophenyl)acetamide (1.8 g, 8.57 mmol) was dissolved in cyclohexane (50 ml), and benzoyl chloride (1.2 g, 8.57 mmol) was added. Finely powdered, fresh anhydrous aluminum chloride (2.85 g, 21.4 mmol) was added in small portion and the reaction mixture was refluxed for 10 hours, before it was poured into crushed ice and concentrated HCl. The solid product obtained was filtered, washed with aqueous sodium hydroxide solution and water and dried; yield 2.20 g (82%).

17.3 Synthesis of [$^{13}C_6$]-7-chloro-5-phenyl-1,3-dihydro-1H,3H-1,4-benzodiazepin-2-one ([$^{13}C_6$]-desmethyldiazepam)

[$^{13}C_6$]-2-(2-Chloroacetamido)-5-chlorobenzophenone (2.0 g, 6.37 mmol) and urotropine (4.55 g, 32.3 mmol) in ethanol reacted in the same manner as described in Example 13.4 to yield [$^{13}C_6$]-desmethyldiazepam 0.62 g, 2.23 mmol (35%).

Example 18

Synthesis of [$^{13}C_6$]-diazepam

[$^{13}C_6$]-7-Chloro-5-phenyl-1,3-dihydro-1H,3H-1,4-benzodiazepin-2-one ([$^{13}C_6$]-desmethyldiazepam) (0.50 g, 1.82 mmol) was methylated to [$^{13}C_6$]-diazepam in the same method as described in Example 15.2, yielded [$^{13}C_6$]-diazepam (0.37 g, 1.27 mmol) (69.8% yield).

Example 19

Synthesis of [$^{13}C_6$]-alprazolam

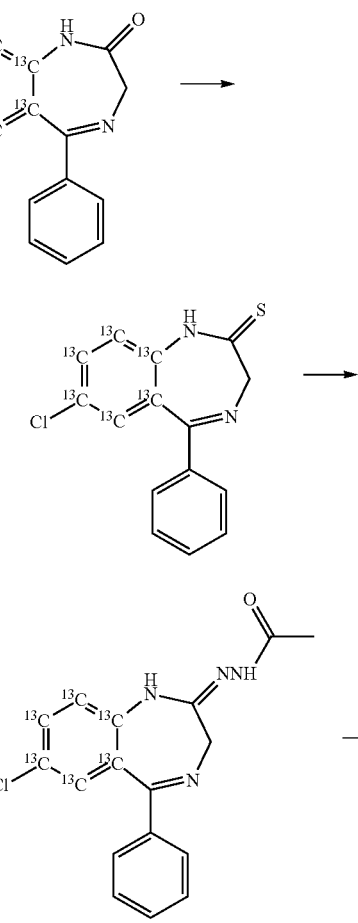

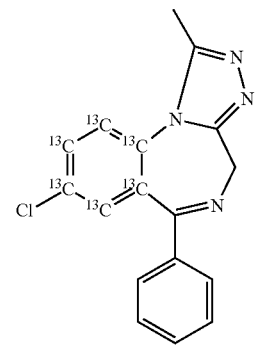

19.1 Synthesis of [$^{13}C_6$]-7-chloro-5-phenyl-1,3-dihydro-1,4-benzodiazepin-2-thione A solution of [$^{13}C_6$]-7-chloro-5-phenyl-1,3-dihydro-1H,3H-1,4-benzodiazepin-2-one (0.7 g, 2.89 mmol) in pyridine (50 mL) was treated with phosphorus pentasulfide (0.64 g, 2.89 mmol) and heated under reflux in an argon atmosphere for 2 hours. The pyridine was removed in vacuo and the residue was poured onto crushed ice. The water phase was extracted with dichloromethane, and the combined organic phases were washed with water and aqueous NaCl solution and dried over sodium sulfate. After removal of the solvent, the crude product was recrystallized with ethanol/water to give 0.69 g pure product (80.4%).

19.2 Synthesis of [$^{13}C_6$]-2-(2-acetylhydrazino)-7-chloro-5-phenyl-1,3-dihydro-1,4-benzodiazepine

[$^{13}C_6$]-7-Chloro-5-phenyl-1,3-dihydro-1,4-benzodiazepin-2-thione (1.0 g, 3.0 mmol) and acethydrazide (0.67 g, 9.0 mmol) in absolute ethanol (40 mL) were refluxed under argon atmosphere for 24 hours. The ethanol was removed in vacuo and the residue was suspended in dichloromethane. The solid was filtered, and the filtrate was concentrated and crystallized from ethyl acetate to give crude product, which was recrystallized from dichloromethane/ethyl acetate; yield 0.6 g (60%).

19.3 Synthesis of [$^{13}C_6$]-8-chloro-1-methyl-6-phenyl-4H-s-triazolo[4,3-a]-1,4-benzodiazepine ([$^{13}C_6$]-alprazolam)

[$^{13}C_6$]-2-(2-acetylhydrazino)-7-chloro-5-phenyl-1,3-dihydro-1,4-benzodiazepine (0.5 g, 15.0 mmol) was heated under argon at 250° C. to melt for 10-15 min, cooled and crystallized from ethyl acetate to give 189 mg (40% yield) of [$^{13}C_6$]-alprazolam.

Example 20

Synthesis of [$^{13}C_6$]-oxazepam

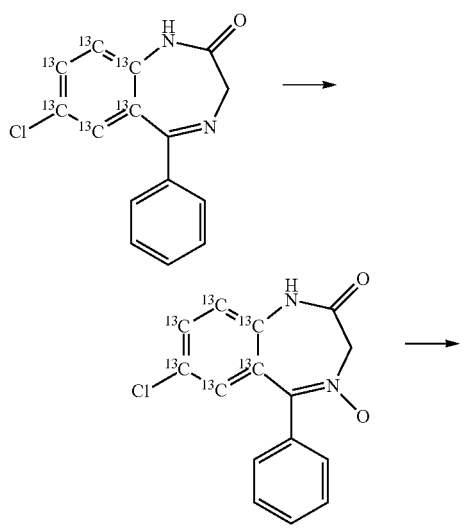

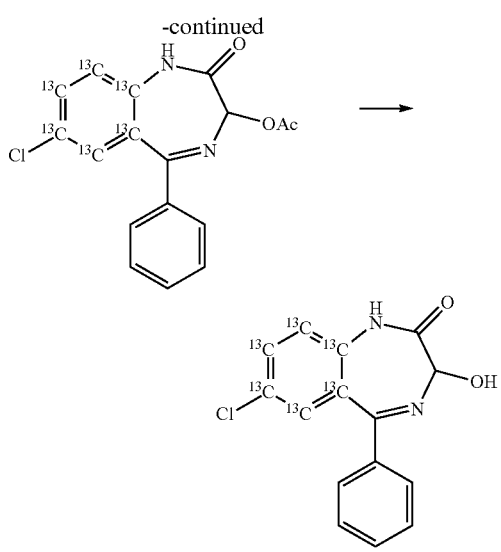

20.1 Synthesis of [$^{13}C_6$]-7-chloro-5-phenyl-1,3-dihydro-1H,3H-1,4-benzodiazepin-2-on-4-oxide

[$^{13}C_6$]-7-Chloro-5-phenyl-1,3-dihydro-1H,3H-1,4-benzodiazepin-2-one (0.57 g, 2.06 mmol) was dissolved in 15 ml of dichloromethane, and 3-chloro-peroxybenzoic acid (1.43, 4.1 mmol) was added. The mixture was stirred at room temperature for 2.5 hours, and then was washed with a 5% NH$_4$OH aqueous solution (20 mL) and a 0.1 N NaOH solution (20 mL). The solvent was removed and the oily residue was dissolved in warm isopropanol and the product was crystallized when cooling down to room temperature. The solid was filtered and washed with isopropanol to yield 0.33 g (54.3%).

20.2 Synthesis of [$^{13}C_6$]-3-acetoxy-7-Chloro-5-phenyl-1,3-dihydro-1H,3H-1,4-benzodiazepin-2-one

[$^{13}C_6$]-7-Chloro-5-phenyl-1,3-dihydro-1H,3H-1,4-benzodiazepin-2-on-4-oxide (0.3 g, 1.0 mmol) was dissolved in 10 ml of THF, and 6 ml of acetic anhydride. The mixture was refluxed for 5 hours, and was then concentrated in vacuo. The crystalline residue was treated with isopropyl ether, filtered and dried under high vacuum. The yield was 0.32 g (95.6%).

20.3 Synthesis of [$^{13}C_6$]-oxazepam

[$^{13}C_5$]-3-Acetoxy-7-chloro-5-phenyl-1,3-dihydro-1H,3H-1,4-benzodiazepin-2-one (0.2 g, 0.6 mmol) was suspended in methanol (5 mL). The slurry was heated to reflux for 20 min. A solution of KOH (40 mg) in methanol (4 mL) was added to the mixture at 65-70° C. so that the pH is maintained at 11-12. After the addition was complete, the resulting solution was clear and yellow. The mixture was stirred for additional 15 minutes at reflux, whereafter acetic acid was added until a pH of 7 was achieved. Water (1 mL) was added to the reaction mixture at 65-70° C., and then the solution was cooled to 15-20° C. and stirred for 2 hours at the same temperature. Water (3 mL) was added to the solution, and the mixture was cooled down to 0-5° C. and stirred for 1 hour. The participated solid was filtered off, washed water and dried. The yield was 0.14 g (79.7%).

Example 21

Synthesis of [$^{13}C_6$]-temazepam

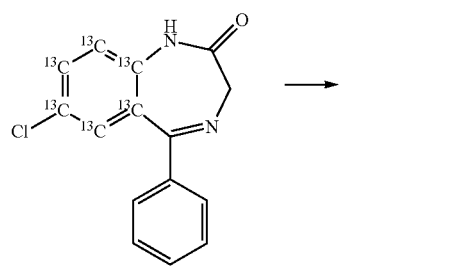

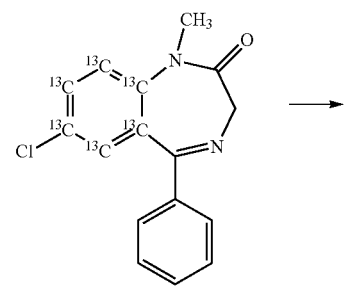

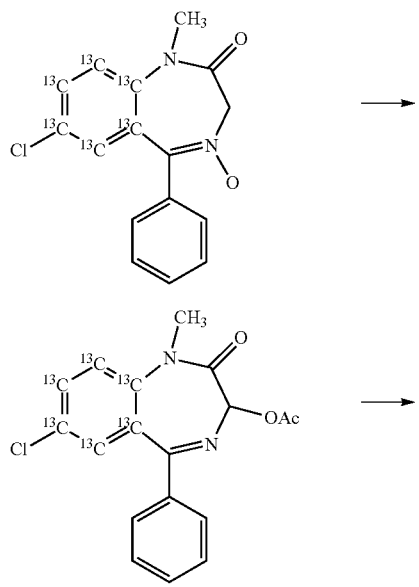

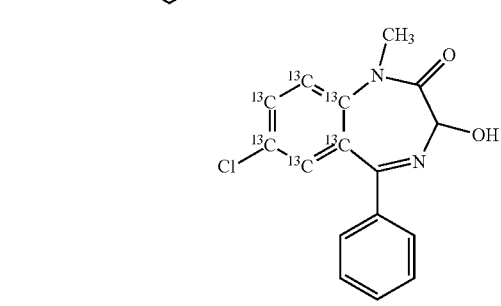

21.1 Synthesis of [$^{13}C_6$]-7-chloro-1-methyl-5-phenyl-1,3-dihydro-1H,3H-1,4-benzodiazepin-2-on-4-oxide

[$^{13}C_6$]-diazepam (0.5 g, 1.81 mmol) in 15 mL of dichloromethane was reacted with 3-chloro-perbenzoic acid (1.25 g, 3.60 mmol) as described in Example 20.1. [$^{13}C_6$]-7-Chloro-1-methyl-5-phenyl-1,3-dihydro-1H,3H-1,4-benzodiazepin-2-on-4-oxide was obtained as a white solid; yield: 0.29 g, 1.01 mmol (56%).

21.2 Synthesis of [$^{13}C_6$]-3-acetoxy-7-chloro-1-methyl-5-phenyl-1,3-dihydro-1H,3H-1,4-benzodiazepin-2-one

[$^{13}C_6$]-7-Chloro-1-methyl-5-phenyl-1,3-dihydro-1H,3H-1,4-benzodiazepin-2-on-4-oxide (0.25 g, 0.86 mmol) and acetic anhydride (6 mL) were reacted in THF (10 mL) as described in Example 20.2 to yield [$^{13}C_6$]-3-acetoxy-7-chloro-1-methyl-5-phenyl-1,3-dihydro-1H,3H-1,4-benzodiazepin-2-one 0.25 g, 0.82 mmol (95.3%).

21.3 Synthesis of [$^{13}C_6$]-temazepam

[$^{13}C_6$]-3-acetoxy-7-chloro-1-methyl-5-phenyl-1,3-dihydro-1H,3H-1,4-benzodiazepin-2-one (0.25 g, 0.82 mmol) was hydrolyzed with KOH in methanol as described in example 20.3, [$^{13}C_6$]-temazepam 0.19 g, 0.61 mmol was obtained; yield 75%.

Example 22

Synthesis of [$^{13}C_6$]-zolpidem

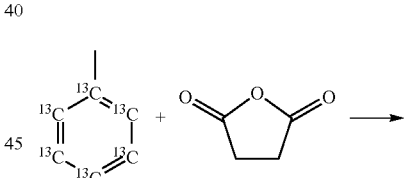

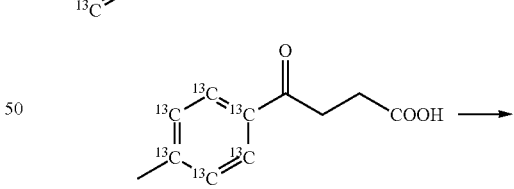

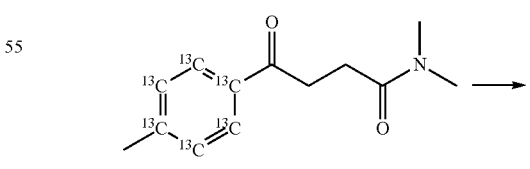

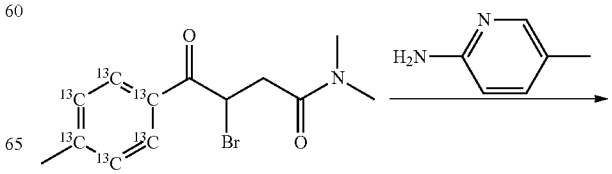

-continued

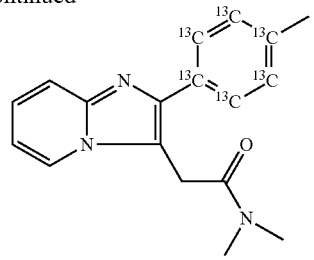

22.1 Synthesis of [$^{13}C_6$]-3-(4-methylbenzoyl) propanoic acid

Succinic anhydride (2.2 g, 16.3 mmol) was added slowly to a mixture of [$^{13}C_6$]-toluene (0.725 g, 7.4 mmol) and AlCl$_3$ (14.7 g, 110 mmol) at 0° C. under argon. The mixture was stirred at 0° C. for 1 hour before it was allowed to warm to room temperature, and then to 95° C. for 2.5 hours. The reaction mixture was cooled down to room temperature before it was poured onto ice-water and hydrochloric acid (5 mL) and extracted with dichloromethane. The combined organic extracts were washed with NaCl aqueous solution and water and dried over sodium sulphate. The solvent was removed in vacuo to yield 1.3 g (88.6%) of the product.

22.2 Synthesis of [$^{13}C_6$]-N,N-dimethyl-3-(ethylbenzoyl)propionamide

[$^{13}C_6$]-3-(4-Methylbenzoyl)propanoic acid (1.3 g, 6.56 mmol) was dissolved in dichloromethane (10 mL) and cooled to 0° C. Triethylamine (1.07 mL, 7.4 mmol) was added, followed by tert-Butylcarbonyl chloride (0.91 ml, 7.4 mmol). The mixture was stirred for 15 min at 0° C., and then diethylamine water solution (33%, 2 mL) was added. The mixture was warmed to room temperature for 30 min. The reaction mixture was washed with water, and sodium carbonate solution. The organic phase was dried over sodium sulphate. After the solvent was removed, the crude solid product was recrystallized with n-hexane/dichloromethane. The yield was 1.45 g (98.1%).

22.3 Synthesis of [$^{13}C_6$]-N,N-dimethyl-2-bromo-3-(4-methylbenzoyl) propionamide A solution of bromine (1.0 g bromine in 7 mL chloroform) was added to a stirred solution of [$^{13}C_6$]-N,N-dimethyl-3-(4-methylbenzoyl)propionamide (1.4 g, 6.21 mmol) in chloroform (20 mL) at 55° C. while keeping the temperature between 55 to 60° C. The resulting solution was stirred for 2 hours at 55° C. and cooled to room temperature. A solution of sodium metabisulphite (35 mg in 2 mL of water) was added. The mixture was then stirred for 10 min, washed with water, 5% sodium carbonate and saturated NaCl aqueous solution and dried over sodium sulphate. The solvent was removed, and the crude product was recrystallized with n-hexane. The yield was 1.75 g (92.7%).

22.3 Synthesis of [$^{13}C_6$]-zolpidem

2-Amino-5-methylpyridine (0.54 g, 5.0 mmol) and [$^{13}C_6$]-N,N-dimethyl-2-bromo-3-(4-methylbenzoyl) propionamide (1.52 g, 5.0 mmol) were dissolved in acetonitrile (20 ml), and the mixture was warned to reflux for 18 hours. The mixture was then cooled down to room temperature, and the precipitated solid was filtered and washed with acetone. The obtained solid was treated with 10% sodium carbonate at pH 6.8-7, filtered and dried. The yield of [$^{13}C_6$]-zolpidem was 0.20 g (12.9%).

Example 23

Synthesis of [$^{13}C_5$]-JWH-073

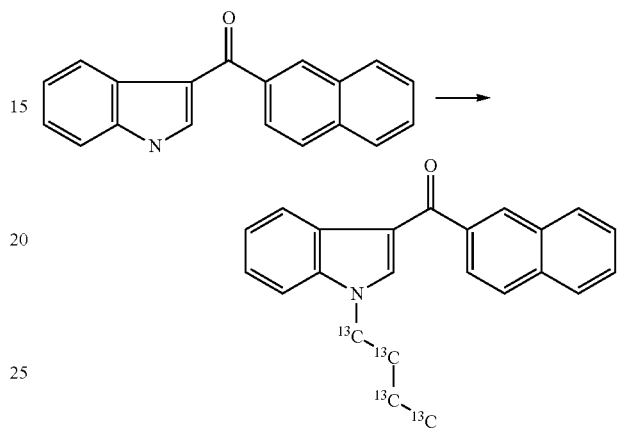

Naphthalen-1-yl[1-[$^{13}C_4$]-butyl-1H-indol-3-yl] methanone. Referred to as [$^{13}C_4$]-JWH-073

Indol-3-yl(naphthalen-1-yl)methanone (0.56 g, 2.1 mmol) was dissolved in DMSO (5 mL). 1,2,3,4-[$^{13}C_4$]-1-Bromobutane (0.48 g, 3.4 mmol) was added, followed by KOH (0.223 g, 3.9 mmol). The reaction mixture was stirred at 80° C. under an argon atmosphere for 3 h. Dichloromethane (10 mL) and water (20 mL) was added, and the organic phase was separated. The aqueous phase was washed with additional dichloromethane (2×20 mL) and combined with the organic phase. The organic extracts were dried over MgSO$_4$ and evaporated under vacuum. The residue was purified by flash chromatography on silica using 17% EtOAc in heptane as eluent. The product was a semisolid that was crystallized from ether and pentane (1:10) in a freezer. The yield of the labeled [$^{13}C_5$]-JWH-073 compound was 577.6 mg (83%).

Example 24

The Synthesis of DL-[$^{13}C_6$]-amphetamine

24.1 The Synthesis of 2-nitro-1-propene-1-yl-[$^{13}C_6$]-benzene

[$^{13}C_6$]-benzaldehyde (1.0 g, 8.92 mmol) was added to nitroethane (5 mL) in a 20 mL round bottom beaker with a magnetic stirrer. Anhydrous ammonium acetate (0.16 g, 2.1 mmol) was added, and the solution was warmed to 80° C. before methylamine (33% in ethanol, 0.1 mL) was added in one portion. The reaction was monitored by thin layer chromatography (TLC) with silica on alumina with toluene as the mobile phase. After 2 hours the reaction was complete as confirmed by GC-MS. The solvent from the reaction mixture was evaporated with reduced pressure on a rotary evaporator. The crude product was recrystallized in the beaker by addition of isopropanol (3 mL) and heating until everything was dissolved in the solvent. After slowly cooling to 4° C. overnight, the crystals were separated on a Buchner funnel and washed with a small amount of cold isopropanol. The light yellow crystals obtained were dried thoroughly to remove all of the alcohol and other traces of volatile matter. They yield of 2-nitro-1-propene-1-yl-[$^{13}C_6$]-benzene was 1.1 g (6.508 mmol) corresponding to 72.9% based on [$^{13}C_6$]-benzaldehyde.

24.2 Synthesis of DL-2-[$^{13}C_6$]-benzeneethaneamine sulfate salt

2-Nitro-1-propene-1-yl-[$^{13}C_6$]-benzene (1.1 g, 6.504 mmol) was dissolved in dry toluene (20 mL). The resulting solution was added dropwise to a mixture of Vitride (Red-Al™ sodium bis(methoxyethoxy)aluminum hydride solution (70% in toluene, 5 mL) and dry toluene (22.5 mL) at 70° C. After all the nitrostyrene solution was added, the resulting reaction mixture was stirred for 2 hours under an inert atmosphere. The reaction mixture was left over night at room temperature for the completion of the reaction. Sodium hydroxide in water (5% by dry weight, 50 mL) was then added carefully, and the toluene layer was separated. The water phase was washed with toluene (2×25 mL), and the organic phases were combined and washed with saturated sodium hydrogen carbonate and brine and dried over anhydrous magnesium sulfate. The solvent was evaporated to yield 930 mg of the free base as a light yellow oil. This oil was distilled on a Kugelrohr apparatus and dissolved in anhydrous diethyl ether (20 mL).

The sulfate salt was made by a slow addition of 10% by weight concentrated sulfuric acid in diethyl ether until the pH was 4.5. The salt was separated from the solvent by filtration with a dry Buchner funnel and the product was washed by addition of chilled diethyl ether (2×10 mL). The salt was dried under reduced pressure to yield 751 mg of the product corresponding to 48% based on the nitrostyrene and with purity above 99% as determined by its trifluoroacetic acid (TFAA) derivative on GC-MS.

Example 25

Synthesis of DL-[$^{13}C_6$]-methamphetamine and its Chloride Salt

Amphetamine free base (100 mg, 0.71 mmol) was dissolved in ethyl formate (10 mL). The solution was heated under pressure in an ACE pressure reactor for 2 hours at 100° C. The reaction mixture was cooled to ambient temperature, and the solvent was evaporated under reduced pressure. The resulting carbamate derivative was dissolved in dried diethyl ether (5 mL). The solution was added dropwise to a suspension of lithium aluminium hydride (40.4 mg, 1.07 mmol) in dry diethyl ether (10 mL). The reaction mixture was refluxed for 5 hours. Thereafter, water was carefully added after the reaction mixture had been cooled down to 0° C. on an ice bath. The lithium salt was filtered over Celite™ diatomaceous earth in a Buchner funnel. The granules obtained were washed thoroughly with excess diethyl ether. The combined ether phases were washed with 5% sodium hydroxide and brine before being dried over magnesium sulfate. The solvent was evaporated to yield 96 mg methamphetamine free base.

The free base was redissolved in diethyl ether. The solution was cooled down to 10° C. before HCl dissolved in isopropanol (1.85 mL) was added in small portions onto the pH reached 4. The resulting chloride salt was filtered off with a Buchner funnel, washed with diethyl ether and dried to yield to 110 mg of the product with a purity >98.8% as determined by TFAA derivatization on GC-MS.

Example 26

Synthesis of DL-[$^{13}C_6$]-3,4-methylenedioxyamphetamine hydrochloride (MDA HCl)

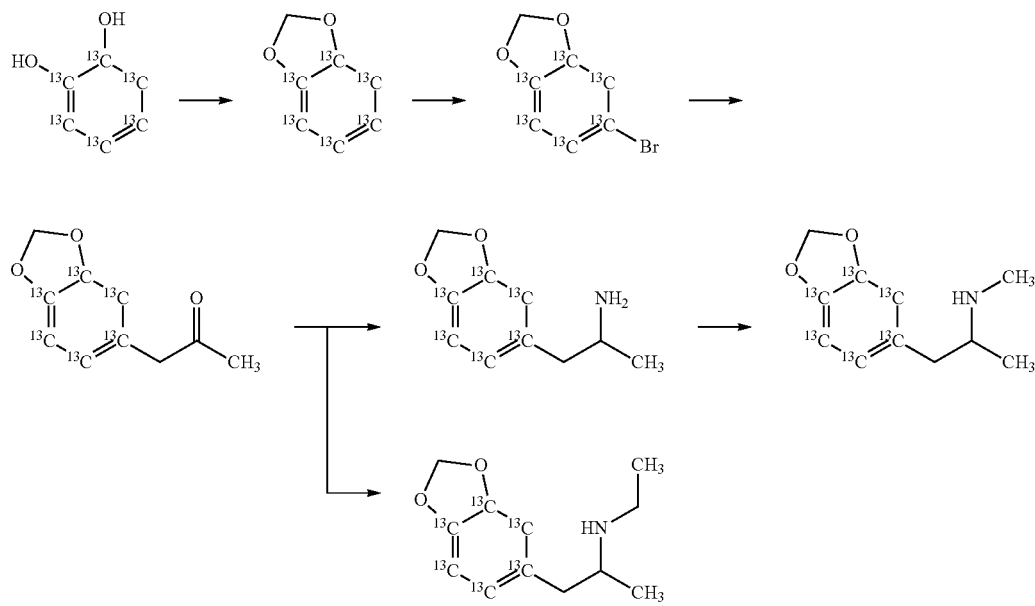

26.1 Synthesis of 3,4-methylenedioxy-[$^{13}C_6$]-benzene

To a stirred solution of 1,2-dihydroxy-[$^{13}C_6$]-benzene (2.76 g, 24 mmol) in DMSO (30 mL), caesium carbonate (15.5 g, 47.6 mmol) was added under an argon atmosphere. The reaction was then stirred at 80° C. for 2 hours. The reaction was quenched by ice water (120 mL) and then the product was steam distilled from the water suspension by two 100 mL water portions. The combined water and product distillate was extracted with ether (3×50 mL). The combined ether extracts were dried over magnesium sulphate. The diethyl ether was evaporated. The yield of 3,4-methylenedioxy-[$^{13}C_6$]-benzene was 3.1 g (99%) based on 1,2-dihydroxy-[$^{13}C_6$]-benzene.

26.2 Synthesis of 3,4-methylenedim-[$^{13}C_6$]-1-bromobenzene 3,4-Methylenedioxy-[$^{13}C_6$]-benzene (3.0 g, 23.8 mmol) was dissolved in chloroform (15 mL). N-bromosuccinimide (4.18 g, 23.5 mmol) was added in small portions with intensive magnetic stirring. The reaction mixture was refluxed for 2 hours. The obtained solids were removed by filtration and washed with two small portions of cold chloroform. The combined organic fractions were evaporated, and ether (150 mL) was added before washing with water (100 mL). The organic phase was purified by dry flash chromatography on a plug of silica in a Buchner funnel using ether as the mobile phase. The yield of 3,4-methylenedioxy-[$^{13}C_6$]-1-bromobenzene was 4.38 g corresponding to 89% based on methylenedioxy-[$^{13}C_6$]-benzene.

26.3 Synthesis of 3,4-methylenedioxy-[$^{13}C_6$]-phenyl-2-propanone 3,4-Methylenedioxy-[$^{13}C_6$]-1-bromobenzene (3.66 g, 17.7 mmol) was dissolved in toluene (30 mL) in a 100 mL reaction flask with a stirring bar and septum. Tri-(o-tolyl) phosphine (322 mg, 1.06 mmol), tributyltinmethoxide (8.51 g, 26.5 mmol) and isopropenyl acetate (2.72 g, 27.2 mmol) was added and Argon was flushed in by the aid of ultrasound degassing and vacuum. Palladium chloride (94 mg, 0.53 mmol) was added rapidly under a blanket of argon. The reaction mixture was then heated to 90° C. for 4 hours. The solvent was then evaporated under vacuum and the crud product is purified by dry flash chromatography on a plug of silica in a Buchner funnel using 15% ethyl acetate in heptane as the mobile phase. The yield of 3,4-Methylenedioxy-[$^{13}C_6$]-phenyl-2-propanone was 2.95 g (90%).

26.4 Synthesis of DL-[$^{13}C_6$]-3,4-methylenedioxyamphetamine hydrochloride (DL-[13C6]-MDA HCl)

3,4-Methylenedioxy-[$^{13}C_6$]-phenyl-2-propanone (313.4 mg, 1.7 mmol) was dissolved in methanol (10 mL). Ammonium acetate was added (1.31 g, 17 mmol), and an argon atmosphere was introduced. Sodium cyanoborohydride was added to this solution in small portions under stirring (113 mg, 1.8 mmol). The reaction was then stirred overnight at room temperature. The solvent was evaporated and 3 M hydrochloric acid was added (30 mL). The aqueous phase was then washed with ether (30 mL) and basified by addition of a concentrated NaOH solution until the pH was 10. The free base product was extracted from the aqueous phase with three portions of ether (30 mL). The combined organic phases were dried over MgSO$_4$. The solvent was evaporated yielding DL-[$^{13}C_6$]-3,4-Methylenedioxyamphetamine as the free base (394 mg). This was dissolved in anhydrous ether (10 mL) and HCl gas was slowly bubbled trough the solution until the pH was 4. The solvent was evaporated, and the product was recrystallized two times from acetonitrile yielding 122.1 mg (32%) [$^{13}C_6$]-MDA hydrochloride as glistening white crystals with a purity greater than 99%.

Example 27

Synthesis of DL-[$^{13}C_6$]-3,4-methylenedioxy-N-methylamphetamine hydrochloride (DL-[$^{13}C_6$]-MDMA HCl)

D,L-[$^{13}C_6$]-MDA as a free base (100 mg, 0.54 mmol) was dissolved in ethylformate (10 mL) and heated under pressure in an ACE pressure reactor for 2 hours at 100° C. The reaction was cooled to room temperature and the solvent was evaporated under reduced pressure. The carbamate derivative was dissolved in dry diethyl ether (5 mL) and added dropwise to a suspension of LiAlH$_4$ (30.75 mg, 0.81 mmol) in diethyl ether (10 mL). The reaction mixture was refluxed for 5 hours. water was added carefully after the temperature had cooled down to 0° C. on an ice bath. The lithium salt was filtered through celite on a Buchner funnel and the granules were washed thoroughly with excess ether. The ether phases were combined and washed with 5% NaOH and brine before drying over MgSO$_4$. The solvent was evaporated to yield the methamphetamine as a free base (96 mg). The crude product was redissolved in diethyl ether and cooled down to 10° C. before HCl dissolved in isopropanol (1.85 M) was added in small portions until the pH was 4. The salt was filtered off on a Buchner funnel, washed with ether and dried to yield D,L-[$^{13}C_6$]-MDMA hydrochloride (110 mg, 86% based on D,L-[$^{13}C_6$]-MDA) with a purity higher than 99% (TFAA derivative, GC/MS analysis).

Example 28

Synthesis of DL-[$^{13}C_6$]-3,4-methylenedioxy-N-ethylamphetamine hydrochloride (DL-[$^{13}C_6$]-MDEA hydrochloride)

3,4-Methylenedioxy-[$^{13}C_6$]-phenyl-2-propanone (338 mg, 1.84 mmol) was dissolved in methanol (10 mL). 15 mol sieves (?) were added together with (752.2 mg, 3.67 mmol) ethylamine in EtOH (22 wt %). The reaction mixture was stirred for 2 hours. NaBH$_4$ (87 mg, 2.3 mmol) was added in small portions and the reaction mixture was stirred over night. 3 M HCl (50 mL) was added, and the reaction mixture was stirred for 1 hour. The water phase was washed with diethyl ether (30 mL) and basified with 50% NaOH solution (pH 11). The product was extracted from the water phase with ether (3×30 mL). The organic phase was washed with brine (30 mL) and dried over MgSO$_4$. The solvent was evaporated yielding DL-[$^{13}C_6$]-3,4-Methylenedioxy-N-ethylamphetamine as the free base. This was dissolved in anhydrous ether (10 mL) and HCl gas was slowly bubbled trough the solution until pH was 4. The solvent was evaporated, and the product was recrystallized two times from isopropanol/ether (15 ml/6 ml) yielding 260.4 mg (58%) [$^{13}C_6$]-MDEA hydrochloride as white crystals with purity greater than 99%.

Example 29

Synthesis of DL-[$^{13}C_6$]-4-methoxy-amphetamine hydrochloride (DL-[$^{13}C_6$]-PMA HCl)

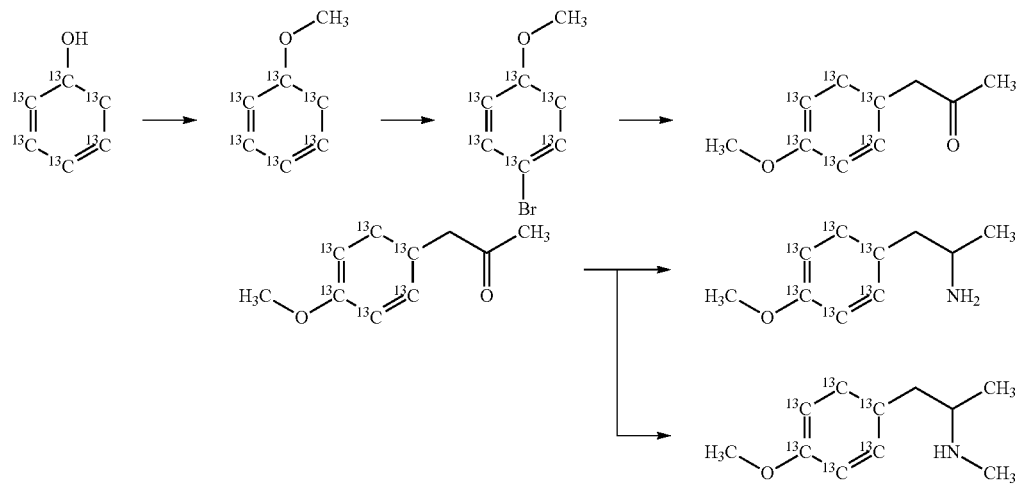

29.1 Synthesis of [$^{13}C_6$]-anisole

[$^{13}C_6$]-Phenol (3.0 g, 30 mmol) was dissolved in water (30 mL). NaOH (1.21 g, 30.3 mmol) was dissolved in water (20 mL) and added to the phenol solution under an argon atmosphere. The reaction mixture was stirred for 30 min and then cooled down to 0° C. on an ice bath. Dimethylsulfate (3.82 g, 30.3 mmol) was added slowly through a cannula and septum. The reaction was gradually warmed to 50° C. and held at that temperature for 1 hour. Then the reaction mixture was extracted with dichloromethane (3×20 mL) and the combined organic phases were washed with 5% NaOH solution (20 mL), brine (20 mL) and dried over MgSO$_4$. The solvent was evaporated to yield 3.9 g [$^{13}C_6$]-anisole (99%).

29.2 Synthesis of 4-brom-[$^{13}C_6$]-anisole

[$^{13}C_6$]-Anisole (3.3 g, 26.6 mmol) was dissolved in chloroform (15 mL) and DMF (2 mL). N-bromosuccinimide (4.73 g, 26.6 mmol) was added in small portions at 70° C. with intensive magnetic stirring. More chloroform was added (50 mL) and the organic phase was washed with water (50 mL). The solvent was evaporated and the crude product was purified by bulb to bulb distillation (70° C., 1.7 mbar). The yield of 4-Bromo-[$^{13}C_6$]-anisole was 4.214 (82%).

29.3 Synthesis of [$^{13}C_6$]-4-ethoxyphenyl-2-propanone

4-Bromo-[$^{13}C_6$]-anisole (1.0 g, 5.2 mmol) was dissolved in toluene (20 mL) in a 100 mL reaction flask with a stirring bar and a septum. Tri-(o-tolyl)phosphine (94 mg, 0.31 mmol), tributyltinmethoxide (2.48 g, 7.72 mmol) and isopropenyl acetate (0.79 g, 27.2 mmol) were added, and Argon was flushed in by the aid of ultrasound degassing and vacuum. Palladium chloride (27.1 mg, 0.15 mmol) was added rapidly under a blanket of argon. The reaction mixture was then heated to 90° C. for 4 hours. The solvent was then evaporated under vacuum and the crude product was purified by dry flash chromatography on a plug of silica in a Buchner funnel using 15% ethyl acetate in heptane as the mobile phase. The yield of [$^{13}C_6$]-4-methoxyphenyl-2-propanone was 972 mg (99%).

29.4 Synthesis of DL-[$^{13}C_6$]-4-methoxyamphetamine hydrochloride (DL-[$^{13}C_6$]-PMA HCl)

4-Methoxy-[$^{13}C_6$]-phenyl-2-propanone (300 mg, 1.76 mmol) was dissolved in methanol (10 mL), and ammonium acetate was added (1.36 g, 17.6 mmol). An argon atmosphere was introduced. Sodium cyanoborohydride was added to the solution in small portions under stirring (113 mg, 1.8 mmol). The reaction mixture was then stirred overnight at room temperature. The solvent was evaporated and 3 M hydrochloric acid was added (30 mL). The waterphase was then washed with ether (30 mL) and basified by addition of a concentrated NaOH solution until the pH was 10. The product freebase was extracted from the aqueous phase with three portions of ether (30 mL). The combined organic phases were dried over MgSO$_4$. The solvent was evaporated yielding DL-[$^{13}C_6$]-4-Methoxyamphetamine as the free base. This was dissolved in anhydrous ether (10 mL) and HCl gas was slowly bubbled trough the solution until pH was 4. The solvent was evaporated, and the product was recrystallized two times from acetonitrile yielding 232.9 mg (66%) [13C6]-PMA hydrochloride as white crystals with purity greater than 99%.

Example 30

Synthesis of DL-[$^{13}C_6$]-4-methoxymethamphetamine hydrochloride (DL-[$^{13}C_6$]-PMMA HCl)

4-Methoxy-[$^{13}C_6$]-phenyl-2-propanone 300 mg, 1.76 mmol) was dissolved in methanol (10 mL). 10 mol sieves were added together with (322 mg, 3.53 mmol) methylamine in EtOH (33 wt %). The reaction mixture was stirred for 2 hours. NaBH$_4$ (84 mg, 2.22 mmol) was added in small portions, and the reaction mixture was stirred over night. 3 M HCl (50 mL) was added and the reaction was stirred for 1 hour. The aqueous phase was washed with diethyl ether (30 mL) and basified with 50% NaOH solution (pH 11). The product was extracted from the water phase with ether (3×30 mL). The organic phase was washed with brine (30 mL) and dried over MgSO$_4$. The solvent was evaporated yielding DL-

[$^{13}C_6$]-4-Methoxymethamphetamine as the free base. This was dissolved in anhydrous ether (10 mL), and HCl gas was slowly bubbled trough the solution until the pH was 4. The solvent was evaporated, and the product was recrystallized two times from iPrOH/ether yielding 292.2 mg (77%) [$^{13}C_6$]-PMMA hydrochloride as white crystals with purity greater than 99%.

The isotopologues described hereinbefore in the Examples 1-30 where excellently suited as internal standards in the quantitative analysis of the corresponding non-labeled drugs by GC-tandem MS and LC-tandem MS. In the GC and LC separation, the isotopologues showed the same retention and elution behavior as the corresponding non-labeled drugs. The internal standards were particularly suitable of minimizing the effects of ion suppression caused by high analyte concentrations. Therefore, the quantitative analysis of the corresponding non-labeled drugs in various biological samples, such as urine, was particularly accurate and reproducible so that the isotopologues were excellent tools in the forensic analysis where particular care is mandatory.

Example 31

The Production of a Type A Test Kit for the Quantitative Determination of Narcotic Drugs The $^{13}C$ labeled isotopologues of the Examples 1-30 and the Comparative Example C1 were diluted or dissolved with methanol or acetonitrile. The solutions were separately transferred in exactly known quantities to septum vials or to flame sealable glass ampoules. The quantities, usually in the order of 0.1 μM were adjusted for each ampoule or septum vial such that each of them was suitable for one analysis of the corresponding narcotic drug. Thereafter, the ampoules and vials were sealed. The thus obtained type A test kit comprising 31 methanol containing sealed vessels and 31 acetonitrile containing sealed vessels was stored for further use.

31 analytical samples were prepared from urine, each sample containing one of the $^{13}C$ labeled isotopologues of the Examples 1-30 and the Comparative Example C1 in known quantities.

Additionally, 15 analytical samples were prepared from urine, each sample containing two of the $^{13}C$ labeled isotopologues of the Examples 1-30 in known quantities.

The ampoules or vials containing the corresponding narcotic drug in methanol were taken from that test kit and homogeneously dispensed in the analytical samples each containing one narcotic drug including one analytical sample containing codeine in a multi-dispenser as internal standards. Thereafter, the narcotic drugs were quantitatively determined in each analytical sample by LC-MS/MS.

The experiments were repeated with the analytical samples each containing two differentially isotopologues of the Examples 1-30.

The results of the experiments revealed that the type A test kits were excellently suited as internal standards for the quantitative determination of the corresponding non-labeled narcotic drugs in biological samples, in particular urine.

Moreover, with the help of the type A test kit, the analytical procedures and the organization in the laboratory could be easily streamlined, standardized and automated. Additionally, it allowed for a comfortable and most accurate calibration of the chosen analytical method.

Contrary to this, the isotopologue C1 was not suited as internal standard because there was a strong overlap of the $^{13}C$-content with the natural $^{13}C$-concentration leading to inaccurate results in the quantitative determination of codeine.

Example 31

The Production of the Type B Test Kits 1-9 and C1 (Comparison) for the Quantitative Determination of Amphetamines and Opiates The isotopologues listed in the Table 1 were mixed and diluted with 5% methanol in water to the concentrations shown. The concentrations in the vessels 1-4 of the standard kits 1-9 and the comparative kit C1 obtained were based on the neat isotopologues, and the isotopologues used were either the bases (modification I) or the hydrochlorides (modification II).

TABLE 1

The Compositions of the Test Kits 1-9 and of the Comparative Kit C1

| Test Kit No. | Isotopologue (Standard) | Vessel 1 Quantity/ μM[a] | Vessel 2 Quantity/ μM[a] | Vessel 3 Quantity/ μM[a] | Vessel 4 Quantity/ μM[a] |
|---|---|---|---|---|---|
| C1 (Comparitive) | [$^{13}C_2$]-Codeine | 0.2 | 1.0 | 5.0 | 20.0 |
| 1 | [$^{13}C_5$]-Heroine | 0.2 | 1.0 | 5.0 | 20.0 |
| 2 | [$^{13}C_3$]-Ethylmorphine | 0.4 | 2.0 | 10.0 | 40.0 |
| 3 | [$^{13}C_6$]-Amphetamine | 0.4 | 2.0 | 10.0 | 40.0 |
| 4 | [$^{13}C_6$]-Methamphetamine | 0.4 | 2.0 | 10.0 | 40.0 |
| 5 | [$^{13}C_6$]-MDA | 0.4 | 2.0 | 10.0 | 40.0 |
| 6 | [$^{13}C_6$]-MDMA | 0.4 | 2.0 | 10.0 | 40.0 |
| 7 | [$^{13}C_6$]-DMEA | 0.4 | 2.0 | 10.0 | 40.0 |
| 8 | [$^{13}C_6$]-PMA | 0.4 | 2.0 | 10.0 | 40.0 |
| 9 | [$^{13}C_6$]-PMMA | 0.4 | 2.0 | 10.0 | 40.0 |

[a]Quantity of the Standard (neat) in the test kit

The test kits 1-9 were excellently suited to provide the internal standards for the quantitative determination of the corresponding non-labeled amphetamines and opiates in biological samples, in particular urine. To this end, the appropriate standard kit containing the corresponding non-labeled drug was selected. Thereafter, the vessel of the said kit containing the most suitable concentration for the chosen and analytical method, as for example, GC-MS, GC-MS/MS, LC-MS, LC-MS/MS, UPLC-MS, UPLC-MS/MS, UPLC-MS/MS, LC-NMR and UPLC-NMR, was selected, and the isotopologue was added as internal standard to the analyte.

Moreover, with the help of the test kits 1-9, the analytical procedures and the organization in the laboratory could be easily streamlined, standardized and automated.

Additionally, the test kits allowed for a comfortable and most accurate calibration of the chosen analytical method.

Contrary to this, the comparative kit C1 was not suited as internal standard because there was a strong overlap of the $^{13}C$-content with a natural $^{13}C$-concentration leading to inaccurate results in the quantitative determination of codeine.

Example 33

The Production of the Type B Test Kits 11-20 for the Quantitative Determination of Benzodiazepines (Test Kits 11-18), the Cocaine Metabolite Benzoylecgonine (Test Kit 19), and Pentazocine (Test Kit 20)

The isotopologues listed in Table 2 were mixed and diluted with 5% methanol in water to the concentrations shown. The concentrations of test kits obtained were based on neat active substances (or metabolites), and the substances used were the bases (modification I) or the hydrochlorides (modification II).

TABLE 2

The Compositions of the Test Kits 10-19

| Test Kit No. | Isotopologue (Standard) | Vessel 1 Quantity/ μM[a] | Vessel 2 Quantity/ μM[a] | Vessel 3 Quantity/ μM[a] | Vessel 4 Quantity/ μM[a] |
|---|---|---|---|---|---|
| 10 | [$^{13}C_6$]-7-Aminonitrazepam | 0.1 | 0.5 | 2.5 | 10.0 |
| 11 | [$^{13}C_6$]-7-Aminoclonazepam | 0.1 | 0.5 | 2.5 | 10.0 |
| 12 | [$^{13}C_6$]-7-Aminoflunitrazepam | 0.1 | 0.5 | 2.5 | 10.0 |
| 13 | [$^{13}C_6$]-Alprazolam | 0.1 | 0.5 | 2.5 | 10.0 |
| 14 | [$^{13}C_6$]-Oxazepam | 0.4 | 2.0 | 10.0 | 40.0 |
| 15 | [$^{13}C_6$]-Temazepam | 0.4 | 2.0 | 10.0 | 40.0 |
| 16 | [$^{13}C_6$]-Desmethyldiazepam | 0.4 | 2.0 | 10.0 | 40.0 |
| 17 | [$^{13}C_6$]-Adinazolam | 0.4 | 2.0 | 10.0 | 40.0 |
| 18 | [$^{13}C_6$]-Benzoylecgonine | 0.4 | 2.0 | 10.0 | 40.0 |
| 19 | [$^{13}C_6$]-Pentazocine | 0.4 | 2.0 | 10.0 | 40.0 |

[a]Quantity of the Standard (neat) in the test kit

Also the test kits 11-20 were excellently suited to provide the internal standards for the quantitative determination of the corresponding non-labeled drugs in biological samples, in particular urine. To this end, the appropriate standard kit containing the corresponding non-labeled drug was selected. Thereafter, the vessel of the said kit containing the most suitable concentration for the chosen and analytical method, as for example, GC-MS, GC-MS/MS, LC-MS, LC-MS/MS, UPLC-MS, UPLC-MS/MS, UPLC-MS/MS, LC-NMR and UPLC-NMR, was selected, and and the isotopologue was added as internal standard to the analyte.

Moreover, with the help of the test kits 11-20, the analytical procedures and the organization in the laboratory could be easily streamlined, standardized and automated.

Additionally, the test kits allowed for a comfortable and most accurate calibration of the chosen analytical method.

Example 34

The Production of the Type B Test Kits 21-23 for the Quantitative Determination of Zoldidem, the Heroine Metabolite 6-MAM, and THC-Acid The isotopologues listed in Table 3 were mixed and diluted with 5% methanol in water to the concentrations shown. The concentrations of test kits 21-23 obtained were based on neat active substances, and the substances used were the bases (modification I) or the hydrochlorides (modification II), except for THC-acid which was used neat.

TABLE 3

The Compositions of the Test Kits 20-22

| Test Kit No. | Isotopologue (Standard) | Vessel 1 Quantity/ μM[a] | Vessel 2 Quantity/ μM[a] | Vessel 3 Quantity/ μM[a] | Vessel 4 Quantity/ μM[a] |
|---|---|---|---|---|---|
| 20 | [$^{13}C_6$]-Zolpidem | 0.1 | 0.5 | 2.5 | 10.0 |
| 21 | [$^{13}C_6$]-6-MAM | 0.4 | 2.0 | 10.0 | 40.0 |
| 22 | [$^{13}C_4$]-THC-Acid | 0.05 | 0.25 | 1.25 | 5.0 |

[a]Quantity of the Standard (neat) in the test kit

The same advantages were obtained as in the previous examples and beneficial effects.

We claim:

1. A test kit for the quantitative determination of narcotic drugs, wherein the test kit comprises
   (A) at least one series of sealed vessels, each vessel containing at least one deuterium free isotopologue of a narcotic drug in exactly defined concentrations and quantities, wherein at least one deuterium free isotopologue differs from vessel to vessel and wherein the quantities of at least one deuterium free isotopologue differ from vessel to vessel or are the same for all vessels; and/or
   (B) at least one series of at least two sealed vessels, each vessel containing in exactly defined concentrations and quantities at least one of the same deuterium free isotopologue in quantities which differ from vessel to vessel;
   the at least one deuterium free isotopologue being selected from
   narcotic drugs;
   prodrugs, salts, solvates, hydrates and polymorphs of narcotic drugs;
   salts, solvates, hydrates and polymorphs of said prodrugs;
   metabolites of narcotic drugs and their prodrugs, salts, solvates, hydrates and polymorphs;
   metabolites of said salts, solvates, hydrates and polymorphs of said prodrugs; and
   salts, solvates, hydrates and polymorphs of said metabolites; and
   containing in the deuterium free isotopologue molecule at least three stable isotopes selected from $^{13}C$, $^{15}N$ and $^{18}O$ with a degree of labeling of at least 95 mol-%.

2. The test kit of claim 1, wherein the test kit comprises a combination of a type (A) test kit and a type (B) test kit.

3. The test kit of claim 1, wherein the test kit comprises a type (A) test kit.

4. The test kit of claim 3, wherein the type (A) test kit comprises at least three sealed vessels.

5. The test kit of claim 1, wherein the test kit comprises a type (B) test kit.

6. The test kit of claim 5, wherein the type (B) test kit comprises at least three sealed vessels.

7. The test kit of claim 1, wherein quantities of at least one isotopologue in each sealed vessel are such that they suffice for at least one analysis of a corresponding narcotic drug in an analytical sample.

8. The test kit of claim 1, wherein the degree of labeling of the isotopologue is at least 99 mol-%.

9. The test kit of claim 1, wherein the deuterium free isotopologue is labeled with at least three $^{13}C$ atoms.

10. The test kit of claim 9, wherein the degree of labeling of the isotopologue is at least 99 mol-%.

11. The test kit of claim 1, wherein the deuterium free isotopologue is in the dissolved state.

12. The test kit of claim 9, wherein the deuterium free isotopologue is in the dissolved state.

13. The test kit of claim 10, wherein the deuterium free isotopologue is in the dissolved state.

14. The test kit of claim 1, wherein a quantity of the deuterium free isotopologue in a sealed vessel ranges from $10^{-7}$ to 1000 μM.

15. The test kit of claim 1, wherein the narcotic drug is selected from
   benzodiazepines, morphines, benzazocines, cocaines, cannabinoids, piperazines, LSD, methadone, naphthoylindoles, naphthylpyrrols and amphetamines;
   prodrugs, salts, solvates, hydrates and polymorphs of said narcotic drugs;
   salts, solvates, hydrates and polymorphs of said prodrugs;

metabolites of said narcotic drugs and their prodrugs, salts, solvates, hydrates and polymorphs;

metabolites of the said salts, solvates, hydrates and polymorphs of said prodrugs; and salts, solvates, hydrates and polymorphs of said metabolites.

16. A method for the quantitative determination of a narcotic drug in chemical analysis and metabolic studies and for calibrating an analytical method used for the quantitative determination of a narcotic drug, wherein the method comprises quantitatively determining a narcotic drug by using the test kit of claim 1.

17. The method of claim 16, wherein the test kit is used for the quantitative determination of a narcotic drug in forensic analysis.

18. A method for the quantitative determination of a narcotic drug in an analytical sample, wherein the method comprises
   (1) identifying the narcotic drug to be quantitatively determined in the analytical sample;
   (2) selecting the sealed vessel or vessels containing the corresponding isotopologue of the narcotic drug from the test kit of claim 1;
   (3) adding the isotopologue to the analytical sample as an internal standard; and
   (4) quantitatively determining the narcotic drug in the analytical sample with an analytical method.

19. The method of claim 18, wherein the analytical sample comprises or consists of a biological sample.

20. The method of claim 19, wherein the biological sample comprises or consist of a body fluid or dispersed solid body material.

* * * * *